(12) United States Patent
Fonquerna Pou et al.

(10) Patent No.: US 7,189,741 B2
(45) Date of Patent: Mar. 13, 2007

(54) INDOLYLPIPERIDINE DERIVATIVES AS ANTIHISTAMINIC AND ANTIALLERGIC AGENTS

(75) Inventors: Silvia Fonquerna Pou, Barcelona (ES); Lluis Pages Santacana, Barcelona (ES); Carles Puig Duran, Barcelona (ES); Lidia Soca Pueyo, Barcelona (ES)

(73) Assignee: Almirall Prodesfarma S.A., Barcelona (ES)

( * ) Notice: Subject to any disclaimer, the term of this patent is extended or adjusted under 35 U.S.C. 154(b) by 453 days.

(21) Appl. No.: 10/415,693

(22) PCT Filed: Oct. 26, 2001

(86) PCT No.: PCT/EP01/12450

§ 371 (c)(1),
(2), (4) Date: Dec. 16, 2003

(87) PCT Pub. No.: WO02/36589

PCT Pub. Date: May 10, 2002

(65) Prior Publication Data

US 2004/0116471 A1 Jun. 17, 2004

(30) Foreign Application Priority Data

Oct. 31, 2000 (ES) .............................. 200002615

(51) Int. Cl.
*A61K 31/445* (2006.01)
*C07D 401/14* (2006.01)
(52) U.S. Cl. ....................... 514/323; 546/201
(58) Field of Classification Search ............... 514/323; 546/201
See application file for complete search history.

(56) References Cited

U.S. PATENT DOCUMENTS

| 4,602,016 | A | 7/1986 | Cross et al. | |
|---|---|---|---|---|
| 4,843,068 | A | 6/1989 | Hamaguchi et al. | |
| 5,650,416 | A | 7/1997 | Carr et al. | 514/321 |
| 5,670,511 | A | 9/1997 | Marz et al. | |
| 6,462,056 | B1 | 10/2002 | Böttcher et al. | |

FOREIGN PATENT DOCUMENTS

| EP | 0 224 919 A2 | 6/1986 |
|---|---|---|
| EP | 0 324 431 | 7/1989 |
| EP | 0 648 759 | 4/1995 |
| EP | 0 722 942 | 7/1996 |
| WO | WO 95/01350 | 1/1995 |
| WO | WO 98/38189 | 9/1998 |
| WO | WO 99/17773 | 4/1999 |
| WO | WO 00/75130 A1 | 12/2000 |
| WO | WO 01/96328 | 12/2001 |

OTHER PUBLICATIONS

Pesenti et al. "Influence of fluorinated molecules . . . " ChemBioChem. v.5, p. 591-613 (2004).*
Wermuth "The practice of medicinal chemistry" Acad. Press, p. 203-206 (1996).*
Seifert et al., Journal of Pharmacology and Experimental Therapeutics, 2003, pp. 1104-1115.*
Garcia-Careaga et al., Nutr. Clin. Pract., 2005, 20(5), abstract.*
Perregaard, J. et al., (1992) "Selective, Centrally Acting Serotonin $5-HT_2$ Antagonists. 1. 2- and 6-Substituted 1-Phenyl-3-(4-piperidinyl)-1*H*-indoles," *J. Med. Chem.* 35:4813-1822.
Shigenaga, S. et al., (1996) "(2E,4E)-N-(4-(1H-Indol-3-yl)poperidin-1-yl)alkyl-5-(substituted phenyl)-2,4-pentadienamides as Antiallergic Agents with Antihistaminic and Anti Slow-Reacting Substance (SRS) Activities," *Arch. Pharm. Pharm. Med. Chem.* 329:3-10.
Chang, R. S. L. et al. (1979). "Heterogeneity of Histamine $H_1$-Receptors: Species Variations in [$^3$H]Mepyramine Binding of Brain Membranes" *Journal of Neurochemistry* 32:1653-1663.
Leysen, J. E. et al. (1991), "Comparative Study of Central and Peripheral Histamine-$H_1$ Receptor Binding In Vitro and Ex Vivo of Non-Sedating Antihistamines and of Noberastine, a New Agent" *Drug Development Research* 22:165-178.

* cited by examiner

*Primary Examiner*—Celia Chang
(74) *Attorney, Agent, or Firm*—Morrison & Foerster LLP

(57) ABSTRACT

The invention relates to indolyl piperidinyl derivatives of formula (I) wherein: $A^1$ represents an alkylene, alkyleneoxy, alkylenethio, alkanoylene or hydroxyalkylene group; $A^2$ represents an alkylene, alkyleneoxy, alkylenethio, alkanoylene or an alkyleneoxyalkylene group; $W^1$ represents a phenylene, furanylene or pyridinylene group which is unsubstituted or substituted by one or more halogen atoms, alkoxy groups and/or alkyl groups; $W^2$ represents a 3–10 membered monocyclic or bicyclic group containing from 1 to 3 heteroatoms said group being unsubstituted or substituted by one or more halogen atoms, alkyl groups, alkoxy groups and/or oxo groups; $R^1$ represents a hydrogen or halogen atom or an alkyl, alkoxy or methylamino group; and $R^2$ represents a carboxyl group; and pharmaceutically acceptable salts thereof; to processes for their preparation; to pharmaceutical compositions containing them; and to their medical use as antihistaminic and antiallergic agents.

14 Claims, No Drawings

INDOLYLPIPERIDINE DERIVATIVES AS ANTIHISTAMINIC AND ANTIALLERGIC AGENTS

The present invention relates to novel indolylpiperidine compounds and pharmacologically acceptable salts thereof which have antihistaminic and antiallergic activity and are useful as medicaments for the treatment of bronchial asthma, allergic rhinitis, conjunctivitis, dermatosis, urticaria and the like.

The present invention also relates to a method for preparing the indolylpiperidine compounds and pharmaceutical compositions useful for the treatment of allergic diseases and bronchial asthma which comprises an effective amount of the indolylpiperidine compound.

Several antihistaminic and antiallergic agents containing the indolylpiperidine core are known. Examples of indolylpiperidine compounds represented by the following formula, where R=H, OH, OR' and n=2–6, are described in *Arch. Pharm.* 1996, 329(1), 3–10.

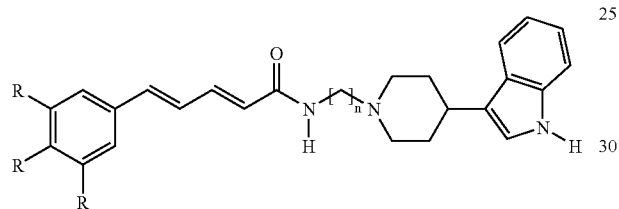

Furthermore, as compounds useful for the treatment of allergic diseases, EP 224919 discloses examples represented by the following formula:

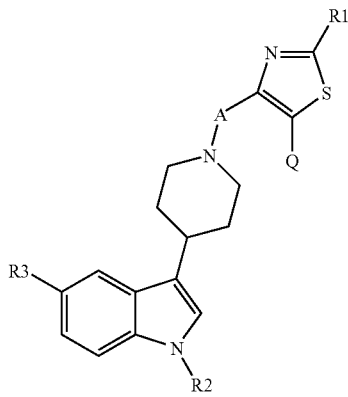

(where $R_1$=opt.subst.amino; $R_2$=H, lower alkyl or aryl; $R_3$=H, $NO_2$, opt.subst.amino, OH or lower alkoxy; A=lower alkylene; Q=H or halogen).

Most of these compounds are characterised as antiallergic agents useful for treating allergic asthma, rhinitis, conjunctivitis and urticaria.

Current antihistamines cannot be considered to be fully satisfactory from a safety point of view and problems remain with respect to adverse reactions such as sleepiness, sedation, hydrodipsia, mydriasis, palpitation and arrhythmia mediated through their undesirable penetration of the central nervous system, antiacetylcholinergic activity, activity against cardiovascular system and the like. Consequently, the clinical need exists for antihistamines and antiallergic agents which are largely devoid of sedative and cardiovascular side-effects.

The present invention provides novel indolylpiperidine compounds having improved antihistamine and antiallergic activity.

The present invention also provides novel indolylpiperidine compounds which due to their lack of lipophilic properties are almost totally unable to penetrate into the brain and hence lack sedative secondary effects. It can also be understood that the compounds of the present invention have reduced cardiovascular side effects.

A further objective of the present invention is to provide a method for preparing said compounds.

Yet another objective is to provide a pharmaceutical composition comprising an effective amount of said compounds.

In accordance with the present invention, indolylpiperidine compounds represented by the formula (I) are provided:

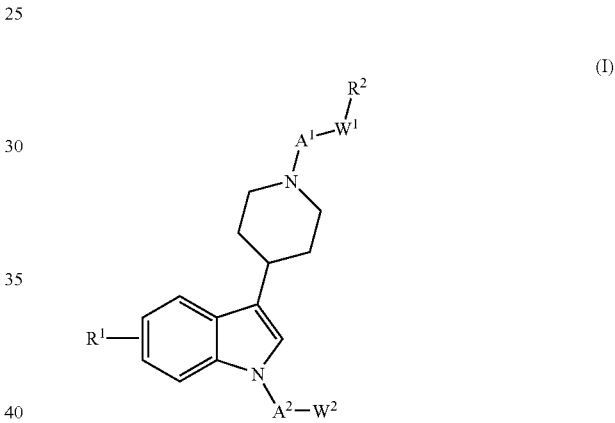

wherein:

$A^1$ represents an alkylene, alkyleneoxy, alkylenethio, alkanoylene or hydroxyalkylene group;

$A^2$ represents an alkylene, alkyleneoxy, alkylenethio, alkanoylene or alkyleneoxyalkylene group;

$W^1$ represents a phenylene, furanylene or pyridinylene group which is unsubstituted or substituted by one or more halogen atoms, alkoxy groups and/or alkyl groups;

$W^2$ represents a 3–10 membered monocyclic or bicyclic group containing from 1 to 3 heteroatoms said group being unsubstituted or substituted by one or more halogen atoms, alkyl groups, alkoxy groups and/or oxo groups;

$R^1$ represents a hydrogen or halogen atom or an alkyl, alkoxy or methylamino group; and $R^2$ represents a carboxyl group;

and pharmaceutically acceptable salts thereof.

In the above formula (I), the alkyl, alkylene, alkyleneoxy, alkylenethio, alkanoylene, hydroxyalkylene and alkoxy groups mentioned in relation to the groups $A^1$, $A^2$, $W^1$, $W^2$ and $R^1$ in the compounds of the invention, may be branched or straight and preferably contain up to 7 and particularly up to 5 carbon atoms.

In the above formula (I), the 3–10 membered monocyclic or bicyclic group containing from 1 to 3 heteroatoms mentioned in relation to the group $W^2$ may be saturated or unsaturated including aromatic. In the monocyclic or bicyclic groups mentioned in relation to the group $W^2$, it will be understood that the 1, 2 or 3 heteroatoms are contained within the cyclic structure. In preferred groups $W^2$ the 1, 2 or 3 heteroatoms are selected from the group consisting of oxygen, sulphur and nitrogen. In the more preferred groups $W^2$ the monocyclic or bicyclic group has from 5 to 9 members in particular the monocyclic or bicyclic group is a monocyclic group having 5 or 6 members or a bicyclic group having 9 members.

In the above formula (I), the expression "one or more" defining the number of optional substituents present in the groups $W^1$ and $W^2$ means from one to the number of substitutable positions on the chemical moiety being substituted. Preferably, in compounds of the invention wherein the $W^1$ and/or $W^2$ groups contain substituents, the groups have from 1–3 substituents. In the compounds of the invention it is to be understood that the substituents mentioned in relation to the groups $W^1$ and $W^2$ may be at any substitutable position or combination of substitutable positions on the chemical moiety being substituted. It will be understood that the phenylene, furanylene or pyridinylene group $W^1$ may be substituted by $A^1$ and $R^2$ at any combination of substitutable ring positions relative to each other, for example 1,2; 1,3; or 1,4. In compounds of the invention wherein the phenylene, furanylene or pyridinylene group $W^1$ is further substituted, the further substituents may be attached at any of the remaining ring positions.

In the above formula (I) it will be understood that the substituent $R^1$ may be attached at the 4, 5, 6 or 7 position of the indolyl nucleus. In preferred compounds of the invention $R^1$ is attached to the 5 or 6 position of the indolyl nucleus.

Further features and advantages of the present invention will become apparent from the description of the preferred compounds which follows, when read in the light of the attached Examples.

In preferred compounds of the invention $A^1$ represents an alkylene or an alkyleneoxy group more preferably a $C_{1-3}$ alkylene such as a methylene, ethylene or propylene group or a $C_{1-5}$ alkyleneoxy group such as a methyleneoxy, ethyleneoxy, propyleneoxy, butyleneoxy or pentyleneoxy group.

In preferred compounds of the invention $A^2$ represents a $C_{1-5}$ alkylene, $C_{1-5}$ alkanoylene, $C_{2-5}$ alkyleneoxy, $C_{2-5}$ alkylenethio or $C_{2-5}$ alkyleneoxy-$C_{1-5}$ alkylene group. In more preferred compounds of the invention $A^2$ represents a methylene, ethylene, propylene, butylene, ethanoylene, propanoylene, butanoylene, ethyleneoxy, propyleneoxy, butyleneoxy, ethylenethio, propylenethio, buytylenethio, ethyleneoxyethylene or ethyleneoxymethylene group.

In preferred compounds of the invention $W^1$ represents a phenylene, furanylene or pyridinylene group which is unsubstituted or substituted by one or more, preferably one or two, substituents selected from fluorine, chlorine or bromine atoms and methyl and methoxy groups. More preferably $W^1$ represents an unsubstituted phenylene, furanylene or pyridinylene group or a phenylene group substituted with a fluorine atom, bromine atom or methoxy group. Most preferably $W^1$ represents an unsubstituted phenylene or a phenylene group substituted with a methoxy group.

In the preferred compounds of the invention the optionally substituted 3–10 membered monocyclic or bicyclic group containing from 1 to 3 heteroatoms specified in the definition $W^2$ is a dioxolanyl, dioxanyl, pyrazolidinyl, isoindolinyl, benzodioxolanyl, tetrahydropyranyl, tetrahydrofuranyl, oxetanyl, furanyl, thienyl, pyrrolyl, pyridinyl, imidazolyl, dihydrothiazolyl, benzothiazolyl, pyrrolidinyl, benzooxazolyl, benzothienyl, pyranyl, benzofuranyl, isobenzylfuranyl, chromenyl, pyrazolyl, oxazolyl, isooxazolyl, furazanyl, isochromanyl, chromanyl, pyrrolinyl, imidazolidinyl, imidazolinyl, pyrazolinyl, piperidyl, piperazinyl, indolinyl, morpholinyl, pyrazinyl, pyrimidinyl, pyridazinyl, indolizinyl, isoindolyl, indolyl, indazolyl, quinazolinyl, isoquinazolinyl, quinolyl, phthalazinyl, naphthyridinyl, quinoxalinyl, quinazolinyl or cinnolinyl group. More preferably the optionally substituted 3–10 membered monocyclic or bicyclic group containing from 1 to 3 heteroatoms is a dioxolanyl, dioxanyl, pyrazolidinyl, isoindolinyl, benzodioxolanyl, tetrahydropyranyl, tetrahydrofuranyl, oxetanyl, furanyl, thienyl, pyrrolyl, pyridinyl, imidazolyl, dihydrothiazolyl, benzothiazolyl, pyrrolidinyl or a benzooxazolyl group. More preferably the optionally substituted 3–10 membered monocyclic or bicyclic group containing from 1 to 3 heteroatoms is a dioxolanyl, dioxanyl, pyrazolidinyl, benzodioxolanyl, tetrahydropyranyl, tetrahydrofuranyl, oxetanyl, furanyl, thienyl, pyrrolyl, pyridinyl, pyrrolidinyl or a benzooxazolyl group.

In compounds of the invention wherein the 3–10 membered monocyclic or bicyclic group containing from 1 to 3 heteroatoms specified in the definition $W^2$ is substituted, the one or more substituents are preferably independently selected from fluorine atoms, chlorine atoms, bromine atoms, $C_{1-7}$ alkyl groups, $C_{1-7}$ alkoxy groups and oxo groups. Most preferably the substituents are selected from chlorine atoms, $C_{1-4}$ alkyl groups, methoxy groups and oxo groups.

In particularly preferred compounds of the invention the optionally substituted 3–10 membered monocyclic or bicyclic group containing from 1 to 3 heteroatoms specified in the definition $W^2$ is a 5 membered ring containing 1 or 2 heteroatoms and the ring is either unsubstituted or substituted by a $C_{1-7}$ alkyl group or a chlorine atom.

In preferred compounds of the invention $R^1$ represents a hydrogen, fluorine, chlorine or bromine atom or a methyl, methoxy or methylamino group. Most preferably $R^1$ represents a hydrogen, a fluorine atom or a methoxy group.

More preferred compounds of formula (I) are those in which $A^1$ represents a methylene, ethylene or ethyleneoxy group; $A^2$ represents a methylene, ethylene, propylene, butylene, ethyleneoxy, propyleneoxy, ethyleneoxyethylene, ethyleneoxymethylene, ethanoylene, butanoylene or a propylenethio(propylsulfanylene) group; $W^1$ represents an unsubstituted phenylene, furanylene or pyridinylene group or a phenylene group substituted with one or more fluorine, bromine or methoxy groups; $W^2$ represents a (1,3)-dioxolanyl, (1,3)-dioxanyl, 2,5,5-trimethyl-[1,3]-dioxan-2-yl, isoindolyl, 1,3-dioxo-1,3-dihydroisoindolinyl, (1,3)-benzodioxolanyl, tetrahydropyranyl, tetrahydrofuranyl, oxetanyl, furanyl, thienyl, 5-chlorothienyl, pyrrolyl, pyridinyl, imidazolyl, methylimidazolyl, dihydrothiazolyl, benzothiazolyl, pyrrolidinyl, pyrrolidinonyl, benzoxazolonyl, phthalimidoyl, benzooxazolyl, 2-oxobenzooxazolyl or 5-methyl-2-oxobenzooxazolyl group; $R^1$ represents a hydrogen, a fluorine atom or a methoxy group, for example a hydrogen atom or a fluorine atom, and $R^2$ represents a carboxyl group.

More preferred compounds of formula (I) are those in which A¹ represents a methylene, ethylene or ethyleneoxy group; A² represents a methylene, ethylene, propylene, butylene or a ethyleneoxy group; W¹ represents an unsubstituted phenylene, furanylene or pyridinylene group or a phenylene group substituted with one or more fluorine, bromine or methoxy groups; W² represents a (1,3)-dioxolanyl, (1,3)-dioxanyl, tetrahydropyranyl, tetrahydrofuranyl, oxetanyl, furanyl, thienyl, 5-chlorothienyl, pyrrolyl or a pyridinyl group; R¹ represents an hydrogen, a fluorine atom or a methoxy group and R² represents a carboxyl group.

The pharmacologically acceptable salts of the compounds of the present invention represented by formula (I) may be acid addition salts or alkali addition salts. Examples of the acid addition salts include mineral acid addition salts such as, for example, hydrochloride, hydrobromide, hydroiodide, sulfate, nitrate, phosphate, and organic acid addition salts such as, for example, acetate, maleate, fumarate, citrate, oxalate, succinate, tartrate, malate, mandelate, methanesulfonate, and p-toluenesulfonate. Examples of the alkali addition salts include inorganic salts such as, for example sodium, potassium, calcium and ammonium salts and organic alkali salts such as, for example, ethylenediamine, ethanolamine, N,N-dialkylenethanolamine, triethanolamine and basic amino acid salts.

The compounds of the present invention represented by the above-described formula (I) may include enantiomers depending on their asymmetry or diastereoisomers. The single isomers and mixtures of the isomers fall within the scope of the present invention.

The preferred indolylpiperidine compounds of the present invention include the following compounds:

1. 2-{2-[4-(1-[1,3]dioxolan-2-ylmethyl-1H-indol-3-yl)-piperidin-1-yl]-ethoxy}-benzoic acid
2. 2-(2-{4-[1-(tetrahydro-pyran-2-ylmethyl)-1H-indol-3-yl]-piperidin-1-yl}-ethoxy)-benzoic acid
3. 2-{2-[4-(1-pyridin-4-ylmethyl-1H-indol-3-yl)-piperidin-1-yl]-ethoxy}-benzoic acid
4. 2-(2-{4-[1-(3-pyrrol-1-yl-propyl)-1H-indol-3-yl]-piperidin-1-yl}-ethoxy)-benzoic acid
5. 2-(2-{4-[1-(3-thiophen-2-yl-propyl)-1H-indol-3-yl]-piperidin-1-yl}-ethoxy)-benzoic acid
6. 2-[2-(4-{1-[3-(1-methyl-1H-imidazol-2-ylsulfanyl)-propyl]-1H-indol-3-yl}-piperidin-1-yl)-ethoxy]-benzoic acid
7. 2-[2-(4-{1-[2-(2,5,5-trimethyl-[1,3]dioxan-2-yl)-ethyl]-1H-indol-3-yl}-piperidin-1-yl)-ethoxy]-benzoic acid
8. 2-{2-[4-(1-thiophen-2-ylmethyl-1H-indol-3-yl)-piperidin-1-yl]ethoxy}-benzoic acid
9. 2-{2-[4-(1-furan-2-ylmethyl-1H-indol-3-yl)-piperidin-1-yl]-ethoxy}-benzoic acid
10. 2-(2-{4-[1-(2-oxo-2-pyrrolidin-1-yl-ethyl)-1H-indol-3-yl]-piperidin-1-yl}-ethoxy)-benzoic acid
11. 2-{2-[4-(1-thiophen-3-ylmethyl-1H-indol-3-yl)-piperidin-1-yl]-ethoxy}-benzoic acid
12. 2-(2-{4-[1-(2-thiophen-2-yl-ethyl)-1H-indol-3-yl]-piperidin-1-yl}-ethoxy)-benzoic acid
13. 2-(2-{4-[1-(2-thiophen-3-yl-ethyl)-1H-indol-3-yl]-piperidin-1-yl}-ethoxy)-benzoic acid
14. 2-[2-(4-{1-[3-(tetrahydro-furan-2-yl)-propyl]-1H-indol-3-yl}-piperidin-1-yl)-ethoxy]-benzoic acid
15. 2-(2-{4-[1-(4-[1,3]dioxolan-2-yl-butyl)-1H-indol-3-yl]-piperidin-1-yl}-ethoxy)-benzoic acid
16. 2-[2-(4-{1-[3-(benzo[1,3]dioxol-5-yloxy)propyl]-1H-indol-3-yl}piperidin-1-yl)ethoxy]benzoic acid
17. 2-[2-(4-{1-[3-(1,3-dioxo-1,3-dihydro-isoindol-2-yl)-propyl]-1H-indol-3-yl}-piperidin-1-yl)-ethoxy]-benzoic acid
18. 2-{2-[4-(1-benzo[1,3]dioxol-5-ylmethyl-1H-indol-3-yl)-piperidin-1-yl]-ethoxy}-benzoic acid
19. 2-(2-{4-[1-(5-chloro-thiophen-2-ylmethyl)-1H-indol-3-yl]-piperidin-1-yl}-ethoxy)-benzoic acid
20. 2-[2-(4-{1-[4-(5-methyl-2-oxo-benzooxazol-3-yl)-butyl]-1H-indol-3-yl}-piperidin-1-yl)-ethoxy]-benzoic acid
21. 2-(2-{4-[1-(3-[1,3]dioxolan-2-yl-propyl)-1H-indol-3-yl]-piperidin-1-yl}-ethoxy)-benzoic acid
22. 2-{2-[4-(6-fluoro-1-furan-2-ylmethyl-1H-indol-3-yl)-piperidin-1-yl]-ethoxy}-benzoic acid
23. 2-(2-{4-[1-(2-[1,3]dioxolan-2-yl-ethyl)-1H-indol-3-yl]-piperidin-1-yl}-ethoxy)-benzoic acid
24. 2-(2-{4-[1-(2-[1,3]dioxolan-2-yl-ethyl)-6-fluoro-1H-indol-3-yl]-piperidin-1-yl}-ethoxy)-benzoic acid
25. 3-[4-(1-thiophen-2-ylmethyl-1H-indol-3-yl)-piperidin-1-ylmethyl]-benzoic acid
26. 3-[4-(1-pyridin-3-ylmethyl-1H-indol-3-yl)-piperidin-1-ylmethyl]-benzoic acid
27. 3-{4-[1-(5-chloro-thiophen-2-ylmethyl)-1H-indol-3-yl]-piperidin-1-ylmethyl}-benzoic acid
28. 3-{4-[1-(2-[1,3]dioxolan-2-yl-ethyl)-1H-indol-3-yl]-piperidin-1-ylmethyl}-benzoic acid
29. 3-{4-[1-(3-[1,3]dioxolan-2-yl-propyl)-1H-indol-3-yl]-piperidin-1-ylmethyl}-benzoic acid
30. 3-[4-(1-pyridin-4-ylmethyl-1H-indol-3-yl)-piperidin-1-ylmethyl]-benzoic acid
31. 3-(4-{1-[3-(benzo[1,3]dioxol-5-yloxy)-propyl]-1H-indol-3-yl}-piperidin-1-ylmethyl)-benzoic acid
32. 3-[4-(1-[1,3]dioxolan-2-ylmethyl-1H-indol-3-yl)-piperidin-1-ylmethyl]-benzoic acid
33. 3-[4-(1-pyridin-2-ylmethyl-1H-indol-3-yl)-piperidin-1-ylmethyl]-benzoic acid
34. 2-methoxy-5-[4-(1-pyridin-3-ylmethyl-1H-indol-3-yl)-piperidin-1-ylmethyl]-benzoic acid
35. 5-{4-[1-(2-[1,3]dioxolan-2-yl-ethyl)-1H-indol-3-yl]-piperidin-1-ylmethyl}-2-methoxy-benzoic acid
36. 5-{4-[1-(3-[1,3]dioxolan-2-yl-propyl)-1H-indol-3-yl]-piperidin-1-ylmethyl}-2-methoxy-benzoic acid
37. 2-methoxy-5-[4-(1-thiophen-2-ylmethyl-1H-indol-3-yl)-piperidin-1-ylmethyl]-benzoic acid
38. 2-methoxy-5-[4-(1-pyridin-4-ylmethyl-1H-indol-3-yl)-piperidin-1-ylmethyl]-benzoic acid
39. 4-bromo-3-[4-(1-[1,3]dioxolan-2-ylmethyl-1H-indol-3-yl)-piperidin-1-ylmethyl]-benzoic acid
40. 4-bromo-3-[4-(1-pyridin-3-ylmethyl-1H-indol-3-yl)-piperidin-1-ylmethyl]-benzoic acid
41. 4-bromo-3-{4-[1-(2-[1,3]dioxolan-2-yl-ethyl)-1H-indol-3-yl]-piperidin-1-ylmethyl}-benzoic acid
42. 4-bromo-3-{4-[1-(3-[1,3]dioxolan-2-yl-propyl)-1H-indol-3-yl]-piperidin-1-ylmethyl}-benzoic acid
43. 4-bromo-3-[4-(1-thiophen-2-ylmethyl-1H-indol-3-yl)-piperidin-1-ylmethyl]-benzoic acid
44. 2-{4-[5-methoxy-1-(2-thiophen-3-yl-ethyl)-1H-indol-3-yl]-piperidin-1-ylmethyl}-benzoic acid
45. 3-(4-{1-[3-(benzo[1,3]dioxol-5-yloxy)-propyl]-1H-indol-3-yl}-piperidin-1-ylmethyl)-4-bromo-benzoic acid
46. 2-fluoro-5-[4-(1-pyridin-3-ylmethyl-1H-indol-3-yl)-piperidin-1-ylmethyl]-benzoic acid 47. 5-{4-[1-(2-[1,3]dioxolan-2-yl-ethyl)-1H-indol-3-yl]-piperidin-1-ylmethyl}-2-fluoro-benzoic acid
48. 5-{4-[1-(3-[1,3]dioxolan-2-yl-propyl)-1H-indol-3-yl]-piperidin-1-ylmethyl}-2-fluoro-benzoic acid
49. 2-fluoro-5-[4-(1-pyridin-4-ylmethyl-1H-indol-3-yl)-piperidin-1-ylmethyl]-benzoic acid
50. 5-(4-{1-[3-(benzo[1,3]dioxol-5-yloxy)-propyl]-1H-indol-3-yl}-piperidin-1-ylmethyl)-2-fluoro-benzoic acid
51. 5-[4-(1-[1,3]dioxolan-2-ylmethyl-1H-indol-3-yl)-piperidin-1-ylmethyl]-2-fluoro-benzoic acid
52. 2-fluoro-5-[4-(1-pyridin-2-ylmethyl-1H-indol-3-yl)-piperidin-1-ylmethyl]-benzoic acid
53. 2-(2-{4-[1-(tetrahydro-furan-3-ylmethyl)-1H-indol-3-yl]-piperidin-1-yl}-ethoxy)-benzoic acid
54. 2-(2-{4-[1-(2-morpholin-4-yl-ethyl)-1H-indol-3-yl]-piperidin-1-yl}-ethoxy)-benzoic acid
55. 2-(2-{4-[1-(3-methyl-oxetan-3-ylmethyl)-1H-indol-3-yl]-piperidin-1-yl}-ethoxy)-benzoic acid
56. 2-{2-[4-(1-furan-3-ylmethyl-1H-indol-3-yl)-piperidin-1-yl]-ethoxy}-benzoic acid
57. 2-(2-{4-[1-(2-pyridin-2-yl-ethyl)-1H-indol-3-yl]-piperidin-1-yl}-ethoxy)-benzoic acid
58. 3-{4-[1-(tetrahydro-furan-3-ylmethyl)-1H-indol-3-yl]-piperidin-1-ylmethyl}-benzoic acid
59. 3-{4-[1-(3-methyl-oxetan-3-ylmethyl)-1H-indol-3-yl]-piperidin-1-ylmethyl}-benzoic acid
60. 3-{4-[1-(2-thiophen-3-yl-ethyl)-1H-indol-3-yl]-piperidin-1-ylmethyl}-benzoic acid
61. 3-[4-(1-furan-3-ylmethyl-1H-indol-3-yl)-piperidin-1-ylmethyl]-benzoic acid
62. 2-[4-(1-pyridin-3-ylmethyl-1H-indol-3-yl)-piperidin-1-ylmethyl]-nicotinic acid
63. 2-{4-[1-(2-morpholin-4-yl-ethyl)-1H-indol-3-yl]-piperidin-1-ylmethyl}-nicotinic acid
64. 2-[4-(1-thiophen-2-ylmethyl-1H-indol-3-yl)-piperidin-1-ylmethyl]-nicotinic acid
65. 3-{4-[1-(5-chloro-thiophen-2-ylmethyl)-6-fluoro-1H-indol-3-yl]-piperidin-1-ylmethyl}-benzoic acid
66. 3-{4-[6-fluoro-1-(2-thiophen-3-yl-ethyl)-1H-indol-3-yl]-piperidin-1-ylmethyl}-benzoic acid
67. 3-{4-[6-fluoro-1-(2-thiophen-2-yl-ethyl)-1H-indol-3-yl]-piperidin-1-ylmethyl}-benzoic acid
68. 2-methoxy-5-{4-[1-(2-thiophen-2-yl-ethyl)-1H-indol-3-yl]piperidin-1-ylmethyl}-benzoic acid
69. 5-{4-[6-fluoro-1-(2-thiophen-2-yl-ethyl)-1H-indol-3-yl]-piperidin-1-ylmethyl}-2-methoxy-benzoic acid
70. 5-{4-[6-fluoro-1-(2-morpholin-4-yl-ethyl)-1H-indol-3-yl]-piperidin-1-ylmethyl}-2-methoxy-benzoic acid
71. 5-{4-[1-(2-[1,4]dioxan-2-yl-ethyl)-1H-indol-3-yl]-piperidin-1-ylmethyl}-2-methoxy-benzoic acid
72. 3-{4-[1-(2-[1,4]dioxan-2-yl-ethyl)-1H-indol-3-yl]-piperidin-1-ylmethyl}-benzoic acid
73. 2-methoxy-5-[4-(1-thiophen-2-ylmethyl-1H-indol-3-yl)-piperidin-1-ylmethyl]-benzoic acid
74. 4-bromo-3-[4-(1-pyridin-4-ylmethyl-1H-indol-3-yl)-piperidin-1-ylmethyl]-benzoic acid
75. 2-methoxy-5-{4-[1-(2-thiophen-3-yl-ethyl)-1H-indol-3-yl]-piperidin-1-ylmethyl}-benzoic acid
76. 3-{4-[1-(2-morpholin-4-yl-ethyl)-1H-indol-3-yl]-piperidin-1-ylmethyl}-benzoic acid
77. 2-[2-(4-{1-[2-(benzo[1,3]dioxol-5-yloxy)-ethyl]-1H-indol-3-yl}-piperidin-1-yl)-ethoxy]-benzoic acid
78. 5-{4-[6-fluoro-1-(2-thiophen-3-yl-ethyl)-1H-indol-3-yl]-piperidin-1-ylmethyl}-2-methoxy-benzoic acid
79. 5-{4-[1-(5-chloro-thiophen-2-ylmethyl)-6-fluoro-1H-indol-3-yl]-piperidin-1-ylmethyl}-2-methoxy-benzoic acid
80. 5-[4-(6-fluoro-1-furan-3-ylmethyl-1H-indol-3-yl)-piperidin-1-ylmethyl]-2-methoxy-benzoic acid
81. 3-{4-[1-(2-pyridin-2-yl-ethyl)-1H-indol-3-yl]-piperidin-1-ylmethyl}-benzoic acid
82. 5-[4-(6-fluoro-1-thiophen-2-ylmethyl-1H-indol-3-yl)-piperidin-1-ylmethyl]-2-methoxy-benzoic acid
83. 3-[4-(1-furan-2-ylmethyl-1H-indol-3-yl)-piperidin-1-ylmethyl]-benzoic acid
84. 2-(2-{4-[1-(2-[1,4]dioxan-2-yl-ethyl)-1H-indol-3-yl]-piperidin-1-yl}-ethoxy)-benzoic acid
85. 5-[4-(1-furan-2-ylmethyl-1H-indol-3-yl)-piperidin-1-ylmethyl]-2-methoxy-benzoic acid
86. 5-[4-(1-furan-3-ylmethyl-1H-indol-3-yl)-piperidin-1-ylmethyl]-2-methoxy-benzoic acid
87. 3-{4-[5-methoxy-1-(2-thiophen-3-yl-ethyl)-1H-indol-3-yl]-piperidin-1-ylmethyl}-benzoic acid
88. 2-(2-{4-[5-methoxy-1-(2-thiophen-3-yl-ethyl)-1H-indol-3-yl]-piperidin-1-yl}-ethoxy)-benzoic acid
89. 2-{2-[4-(5-methoxy-1-thiophen-2-ylmethyl-1H-indol-3-yl)-piperidin-1-yl]-ethoxy}-benzoic acid
90. 3-[4-(5-methoxy-1-thiophen-2-ylmethyl-1H-indol-3-yl)-piperidin-1-ylmethyl]-benzoic acid
91. 2-methoxy-5-{4-[5-methoxy-1-(2-thiophen-3-yl-ethyl)-1H-indol-3-yl]-piperidin-1-ylmethyl}-benzoic acid
92. 2-{2-[4-(1-furan-3-ylmethyl-5-methoxy-1H-indol-3-yl)-piperidin-1-yl]-ethoxy}-benzoic acid
93. 3-[4-(1-furan-3-ylmethyl-5-methoxy-1H-indol-3-yl)-piperidin-1-ylmethyl]-benzoic acid
94. 2-[4-(1-furan-2-ylmethyl-1H-indol-3-yl)-piperidin-1-ylmethyl]-benzoic acid
95. 2-[4-(6-fluoro-1-furan-2-ylmethyl-1H-indol-3-yl)-piperidin-1-ylmethyl]-benzoic acid
96. 3-[4-(6-fluoro-1-furan-2-ylmethyl-1H-indol-3-yl)-piperidin-1-ylmethyl]-benzoic acid
97. 5-[4-(6-fluoro-1-furan-2-ylmethyl-1H-indol-3-yl)-piperidin-1-ylmethyl]-2-methoxy-benzoic acid
98. 4-methoxy-2-[4-(5-methoxy-1-thiophen-2-ylmethyl-1H-indol-3-yl)-piperidin-1-ylmethyl]-benzoic acid
99. 2-[4-(5-methoxy-1-thiophen-2-ylmethyl-1H-indol-3-yl)-piperidin-1-ylmethyl]-benzoic acid
100. 2-methoxy-5-[4-(5-methoxy-1-thiophen-2-ylmethyl-1H-indol-3-yl)-piperidin-1-ylmethyl]-benzoic acid
101. 2-[4-(1-furan-2-ylmethyl-5-methoxy-1H-indol-3-yl)-piperidin-1-ylmethyl]-4-methoxy-benzoic acid
102. 3-[4-(1-furan-2-ylmethyl-5-methoxy-1H-indol-3-yl)-piperidin-1-ylmethyl]-benzoic acid
103. 2-[4-(1-furan-2-ylmethyl-5-methoxy-1H-indol-3-yl)-piperidin-1-ylmethyl]-benzoic acid
104. 5-[4-(1-furan-2-ylmethyl-5-methoxy-1H-indol-3-yl)-piperidin-1-ylmethyl]-2-methoxy-benzoic acid
105. 2-{2-[4-(1-furan-2-ylmethyl-5-methoxy-1H-indol-3-yl)-piperidin-1-yl]-ethoxy}-benzoic acid
106. 4-methoxy-2-{4-[5-methoxy-1-(2-thiophen-3-yl-ethyl)-1H-indol-3-yl]-piperidin-1-ylmethyl}-benzoic acid
107. 2-{2-[4-(6-fluoro-1-thiophen-2-ylmethyl-1H-indol-3-yl)-piperidin-1-yl]-ethoxy}-benzoic acid
108. 5-[4-(6-fluoro-1-thiophen-3-ylmethyl-1H-indol-3-yl)-piperidin-1-ylmethyl]-2-methoxy-benzoic acid 109. 2-{2-[4-(6-fluoro-1-thiophen-3-ylmethyl-1H-indol-3-yl)-piperidin-1-yl]-ethoxy}-benzoic acid
110. 2-(2-{4-[6-fluoro-1-(2-thiophen-3-yl-ethyl)-1H-indol-3-yl]-piperidin-1-yl}-ethoxy)-benzoic acid
111. 2-(2-{4-[1-(5-chloro-thiophen-2-ylmethyl)-6-fluoro-1H-indol-3-yl]-piperidin-1-yl}-ethoxy)-benzoic acid
112. 2-{2-[4-(6-fluoro-1-furan-3-ylmethyl-1H-indol-3-yl)-piperidin-1-yl]-ethoxy}-benzoic acid
113. 2-{2-[4-(5-methoxy-1-thiophen-3-ylmethyl-1H-indol-3-yl)-piperidin-1-yl]-ethoxy}-benzoic acid
114. 3-[4-(5-methoxy-1-thiophen-3-ylmethyl-1H-indol-3-yl)-piperidin-1-ylmethyl]-benzoic acid
115. 2-(2-{4-[1-(5-chloro-thiophen-2-ylmethyl)-5-methoxy-1H-indol-3-yl]-piperidin-1-yl}-ethoxy)-benzoic acid
116. 3-{4-[1-(5-chloro-thiophen-2-ylmethyl)-5-methoxy-1H-indol-3-yl]-piperidin-1-ylmethyl}-benzoic acid
117. 2-methoxy-5-[4-(1-thiophen-3-ylmethyl-1H-indol-3-yl)-piperidin-1-ylmethyl]-benzoic acid
118. 3-[4-(1-thiophen-3-ylmethyl-1H-indol-3-yl)-piperidin-1-ylmethyl]-benzoic acid
119. 5-{4-[1-(5-chloro-thiophen-2-ylmethyl)-5-methoxy-1H-indol-3-yl]-piperidin-1-ylmethyl}-2-methoxy-benzoic acid
120. 3-{4-[5-methoxy-1-(2-thiophen-2-yl-ethyl)-1H-indol-3-yl]-piperidin-1-ylmethyl}-benzoic acid
121. 2-methoxy-5-{4-[5-methoxy-1-(2-thiophen-2-yl-ethyl)-1H-indol-3-yl]-piperidin-1-ylmethyl}-benzoic acid In accordance with another embodiment of the present invention, it provides a process for preparing a compound represented by formula (I), comprising the hydrolysis of a compound of formula (VI)

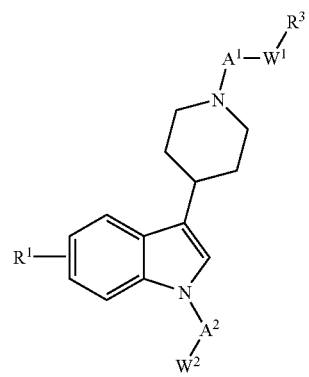

wherein $A^1$, $A^2$, $W^1$, $W^2$ and $R^1$ are as defined above and $R^3$ is a —COOR$^4$ group wherein $R^4$ represents a $C_1$–$C_4$ alkyl group.

The novel indolylpiperidine compounds of the present invention represented by formula (I) can and preferably are prepared according to Scheme 1.

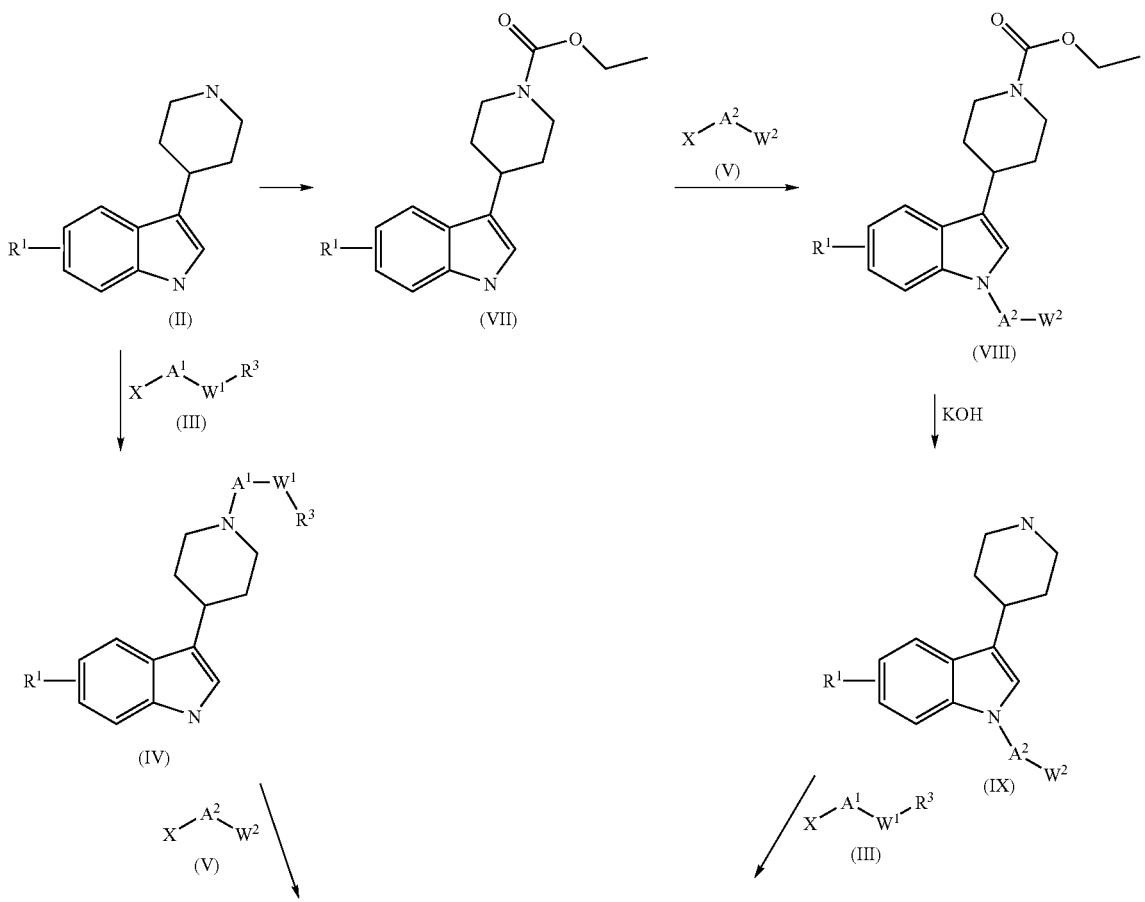

-continued

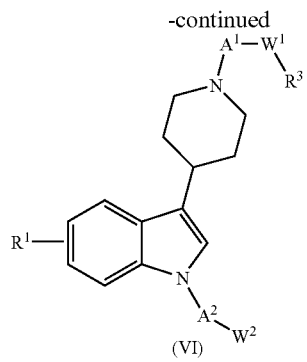

(VI)

↓ NaOH

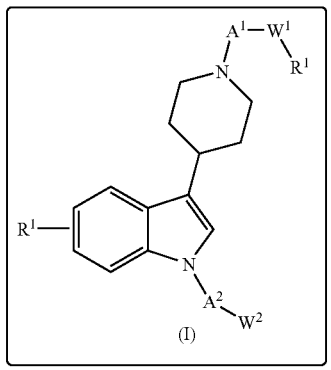

(I)

The piperidine derivative of general structure (II) wherein $R^1$ is as defined above, is alkylated with a reactive intermediate of general formula (III):

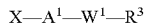 (III)

wherein $A^1$ and $W^1$ are as defined above, $R^3$ is a —COOR$^4$ group where $R^4$ is a $C_1$–$C_4$ alkyl group and X is a leaving group such as a chlorine or bromine atom, or a methane sulfonate, p-toluene sulfonate or benzene sulfonate group.

The reaction is preferably carried out in an inert organic solvent such as toluene, dioxane or methyl isobutyl ketone, at a temperature between 80° C. and 140° C. and in the presence of an inorganic base such as an alkali metal carbonate or bicarbonate.

In the reaction, the corresponding alkylation product of general formula (IV) is formed:

(IV)

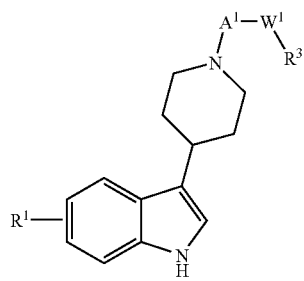

Compound (IV) is alkylated on the indole nitrogen with a reactive intermediate of general formula (V):

 (V)

wherein X is a leaving group such as a chlorine or bromine atom, or a methane sulfonate, p-toluene sulfonate or benzene sulfonate group and $A^2$ and $W^2$ are as defined above.

The reaction is preferably carried out in an inert organic solvent such as dimethylformamide, tetrahydrofuran or ethyl ether, at a temperature between 0° C. and 80° C. in the presence of an inorganic base such as sodium hydride or sodium amide. In the reaction, the corresponding alkylation product of general formula (VI) is formed wherein $R^1$, $R^3$, $W^2$, $A^1$ and $A^2$ are as defined above.

(VI)

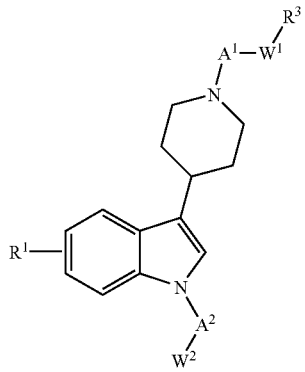

Usually, an excess of the reagents is employed in both alkylations to ensure complete reaction. In such cases, a polymer, such as methyl isocyanate polystyrene or/and 3-(3-mercaptophenyl)-propanamidomethyl polystyrene may be conveniently added to react with the excess reagent. Isolation of the products from reactions where a polymer bound reagent has been used is greatly simplified, requiring only filtration under reduced pressure. The product from these reactions may be purified by solid phase extraction, using a suitable sorbent, such as Varian SCX, or Varian C18.

Following a different pathway (see Scheme 1), the piperidine of compound (II) is protected at its reactive piperidine nitrogen atom by a suitable protecting group such as by forming a carbamate moiety (the ethylcarbamate is shown by way of example) to give compounds of general structure (VII) wherein $R^1$ is as defined above. This reaction is preferably carried out in methylenechloride or chloroform as a solvent in the presence of triethylamine and ethyl chloroformate at a temperature between −20° C. and 30° C.

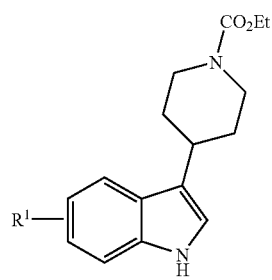

(VII)

Compound (VII) is alkylated on the indole with a reactive intermediate of general formula (V):

wherein X is a leaving group such as a chlorine or bromine atom, or a methane sulfonate, p-toluene sulfonate or benzene sulfonate group and $A^1$ and $W^2$ are as defined above.

This reaction is preferably carried out in an inert organic solvent such as dimethylformamide, tetrahydrofuran or ethyl ether, at a temperature between 0° C. and 80° C. in the presence of an inorganic base such as sodium hydride or sodium amide. In the reaction, the corresponding alkylation product of general formula (VIII) is formed wherein $R^1$, $W^2$ and $A^2$ are as defined above.

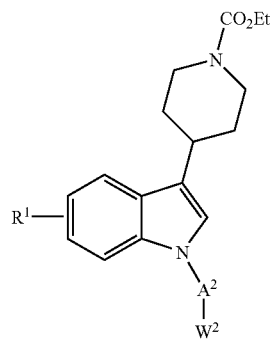

(VIII)

Compound (VIII) is deprotected in the appropriate manner for the protecting group selected in the previous step. For the exemplified carbamate group this can be by boiling in the presence of an excess of sodium or potassium hydroxide in an alcoholic solvent such as ethanol, isopropanol or n-butanol at a temperature between 80° C. and 180° C. Further neutralisation with an inorganic acid such as hydrochloric or sulfuric acid, leads to a compound of general structure (IX) wherein $R^1$, $A^2$ and $W^2$ are as defined above.

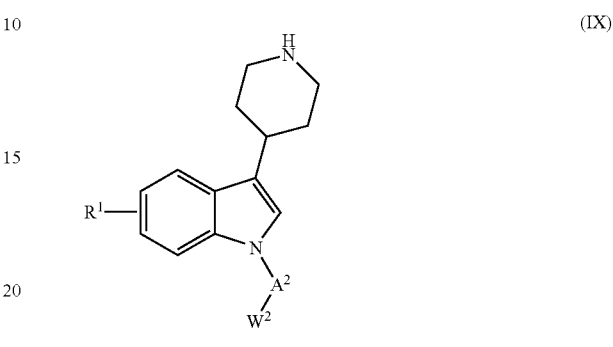

(IX)

Further alkylation of compound (IX) with a reactive intermediate of general formula (III) gives a compound of general structure (VI)

(III)

wherein $R^1$, $A^1$, $A^2$, $W^1$ and $W^2$ are as defined above, $R^3$ a —COOR$^4$ group where $R^4$ is a $C_1$–$C_4$ alkyl group and X is a leaving group such as a chlorine or bromine atom, or a methane sulfonate, p-toluene sulfonate or benzene sulfonate group. The reaction is preferably carried out in an inert organic solvent such as toluene, dioxane or methyl isobutyl ketone, at a temperature between 80° C. and 140° C. in the presence of an inorganic base such as an alkali metal carbonate or bicarbonate.

Compounds of general formula (VI) where $R^1$ represents an alkyl ester are treated with sodium or potassium hydroxide and further neutralisation with an inorganic acid such as hydrochloric or sulfuric acid provides the corresponding indole derivative of formula (I) where $R^2$ is a carboxylic acid. The reaction is preferably carried out in a solvent such as methanol, ethanol, tetrahydrofuran or an aqueous mixture of one of the above mentioned solvents at its boiling point.

Occasionally, the compounds of the present invention are purified by preparative HPLC-MS. In these cases, a Gilson-Termoquest HPLC-MS is used with C-18 preparative columns (5 μm, 1×5 cm, Waters) and using water/formic acid 0.1% as mobile phase.

The piperidine derivatives of formula (II) can be prepared from the 4-piperidone as disclosed in the literature (J. Med. Chem. 1992, 35, 4813–4822). The reactive intermediates of general formula (III) are either commercially available or they can be prepared as disclosed in the literature or their preparation is included in the present invention.

Also included within the scope of the present invention are pharmaceutical compositions which comprise, as the active ingredient, at least one indolylpiperidine derivative of general formula (I), or a pharmacologically-acceptable salt thereof, in association with a pharmaceutically-acceptable carrier or diluent. Preferably the composition is made up in a form suitable for oral, or parenteral administration.

The pharmaceutically-acceptable carriers or diluents which are mixed with the active compound or compounds, or salts thereof, to form the composition of this invention are well-known "per se" and the actual excipients used depend "inter alia" on the intended method of administration of the compositions. Compositions of this invention are preferably adapted for oral administration. In this case, the composition for oral administration may take the form of tablets, capsules or effervescent granules or liquid preparations such as elixirs, syrups or suspensions, all containing one or more compounds of the invention; such preparations may be made by methods well known in the art.

The diluents which may be used in the preparations of the compositions include those liquid and solid diluents which the active ingredient is mixed together with colouring or flavouring agents, if desired. Tablets or capsules may conveniently contain between 0.2 and 500 mg, preferably from 0.5 to 100 mg, of active ingredient or the equivalent amount of a pharmacologically-acceptable salt thereof. The compounds may be incorporated into pellets coated with an appropriate natural or synthetic polymers known in the art to produce sustained release characteristics or incorporated with polymers into tablet form to produce the same characteristics.

The liquid composition adapted for oral use may be in the form of solution or suspension. The solution may be an aqueous solution of an acid addition salt of the indolylpiperidine derivative in association with, for example, sucrose or sorbitol to form a syrup. The suspension may comprise an insoluble or micro encapsulated form of an active compound of the invention in association with water of other pharmaceutically-acceptable liquid medium together with a suspending agent or flavouring agent.

Composition for parenteral injection may be prepared from soluble salts of the indolylpiperidine derivative, which may or may not be freeze-dried and which may be dissolved in water or an appropriate parenteral injectable fluid.

In human therapy, the doses of the compound of general formula (I) depend on the desired effect and duration of treatment; adult doses are generally between 0.2 mg and 500 mg per day and preferably between 0.5 mg and 100 mg per day. In general, the physician will decide the dosing regime taking into account the age and weight of the patient being treated.

Pharmacological Action

The following examples demonstrate the excellent pharmacological activities of the compounds of the present invention. The results of (1) Histamine-$H_1$ receptor binding assay, (2) Histamine-induced skin vascular permeability in rats with the monitoring of antiallergic activity, (3) $H_1$ ex vivo binding studies in mice with the monitoring of degree of penetration into brain and (4) measurement of blood pressure and heart rate in conscious unrestrained hypertensive rats with the monitoring of cardiovascular effects, were obtained as described below.

(1) Histamine-$H_1$ Receptor Binding Assay

Binding to the histamine-$H_1$ receptors was performed in guinea pig cerebellum membranes as described previously (Chang et al., 1979). Briefly, the membrane suspensions (160 µg/ml) were incubated at 30° C. with 0.7 nM [$^3$H]-mepyramine and different concentrations of the test compounds in a final volume of 250 µl. Binding reactions were terminated by filtration after 30 min of incubation and the bound radioactivity was determined. The specific binding was measured in the presence of 10 µM of promethazine. The affinity of each test compound to the receptor was determined by using at least six different concentrations run in duplicate. $IC_{50}$ values were obtained by non-linear regression by use of SAS on a DEC AXP computer.

TABLE 1

Histamine-$H_1$ receptor binding assay

| Compound | Binding to receptor $H_1$ ($IC_{50}$, nM) |
|---|---|
| Cetirizine | 226 |
| Fexofenadine | 214 |
| 1 | 200 |
| 3 | 267 |
| 6 | 463 |
| 9 | 98 |
| 11 | 400 |
| 12 | 43 |
| 13 | 59 |
| 16 | 78 |
| 19 | 120 |
| 21 | 295 |
| 22 | 37 |
| 23 | 354 |
| 24 | 51 |
| 25 | 90 |
| 28 | 205 |
| 50 | 155 |
| 69 | 135 |
| 73 | 125 |
| 75 | 52 |
| 77 | 116 |
| 78 | 65 |
| 79 | 150 |
| 80 | 96 |
| 82 | 91 |
| 85 | 101 |
| 86 | 155 |
| 88 | 51 |
| 96 | 107 |
| 110 | 23 |
| 112 | 31 |

Our results show that the compounds of the present invention have affinities for the $H_1$ receptors very similar to the reference compounds.

(2) Histamine-Induced Skin Vascular Permeability in Rats

Male Wistar rats (180–210 g) were treated orally with the test compound or vehicle. 1, 4, 8 and 24 hours later, the rats were lightly anaesthetized with ether. The cutaneous reaction was induced by two intradermal injections of 50 µl of histamine (100 µg/ml) onto the back, followed by a intravenous injection of 3 ml/kg of Evan's Blue (5 mg/ml), both dissolved in saline. Sixty min later, the rats were killed by cervical dislocation and the back skin dissected free. The diameter (in millimeters) of the papule was measured in two directions and the area was calculated. Results are given as the % of inhibition at a given dose compared with the vehicle treated group.

The compounds disclosed in examples 22, 23, 24, 73, 75, 78, 79, 80, 82, 85 and 86 show an inhibition>50% of the histamine induced skin vascular permeablity at the dose of 1 mg/Kg 4 hours after administration. In the same experimental conditions, cetirizine shows an inhibition of 7% whereas fexofenadine shows a negligible inhibition.

(3) $H_1$ Ex Vivo Binding Studies in Mice

The assay was performed essentially as described by Laysen et al., with the following modifications. Overnight starved male Swiss albino mice (21±2 g) were treated orally with different doses of the test compounds (10 ml/kg, p.o.) and 90 minutes later were killed. The whole brain was dissected out and homogenized in 10 ml of ice-cold 0.05 M $Na^+/K^+$ phosphate buffer (pH 7.4). A 1 ml aliquot of the homogenate was incubated, in triplicate, with 0.1 ml [$^3$H]-mepyramine (2 nM final concentration, 27 Ci/mmol, Amersham) during 40 minutes at 30° C. The [$^3$H]-mepyramine bound to the membranes was determined by immediate filtration of the homogenates under vacuum onto the glass fibre filters (Whatman GF/B) followed by three rapid rinses with 5 ml of cold buffer containing 10 μM cold mepyramine. The radioactivity bound in the filters was determined by liquid scintillation spectrometry. The non-specific binding was determined by treating the animals with 30 mg/kg p.o. D-chlorpheniramine maleate. Mice treated with vehicle (methylcellulose 0.5% and tween 0.1%) were used to determine the total binding. Results are expressed as the % of specific binding at a given dose of the test compound.

The compounds of the present invention display little or no penetration through the blood brain barrier.

(4) Measurement of Blood Pressure and Heart Rate in Conscious Unrestrained Hypertensive Rats Adult male spontaneously hypertensive rats (SHR) were operated upon in order to implant blood pressure sensors in the abdominal aorta just above the iliac bifurcation. After recovery from anaesthesia, rats were housed individually in cages placed on radio-frequency receivers. Amoxycillin (15 mg/kg, i.m., after surgery) was administered to prevent infection. The rats were allowed to recover for at least 2 weeks after transmitter implantation. Arterial blood pressure and heart rate were recorded and analysed by Dataquest V system (Data Science, St. Paul, Minn.). The animals were kept on a 12:12 hours light-dark cycle during the entire recording period. After 18 hours of fasting with water "ad libitum", the animals received drugs orally and were then given food. Hemodynamic recordings were taken every 15 minutes, starting 4 hours before drug administration and continuing up to 24 hours after. Each recording lasted 10 seconds, and the hemodynamic values of all cycles within this period were averaged. All the animals received all the treatments, between administrations in the same rat, there was a seven day wash-out period, and a complete recovery to base-line values was ascertained. The effects of treatments on mean arterial blood pressure and heart rate were determined with one-way analysis of variance (ANOVA). A P value<0.05 was considered statistically significant.

The compounds of the present invention have little or no effects on blood pressure and heart rate at doses from 3 to 30 mg/kg.

From the above described results it will be understood that that the compounds of the present invention have excellent antihistamine and antiallergic activities. Compounds of the present invention have reduced cardiovascular and central nervous system side effects and are thus useful for the treatment of various allergic disorders, for instance, bronchial asthma, rhinitis, conjunctivitis, dermatitis and urticaria. The invention thus provides a method for treating an allergic disorder for instance, bronchial asthma, rhinitis, conjunctivitis, dermatitis and urticaria comprising the step of administering to a human or animal patient in need of such treatment an effective amount of a compound of formula (I). The invention also provides the use of the compounds of formula (I) in the manufacture of a medicament for the treatment of an allergic disorder for instance, bronchial asthma, rhinitis, conjunctivitis, dermatitis and urticaria.

The present invention will be further illustrated by the following Examples. These Examples are given by way of illustration only and are not to be construed as limiting.

TABLE 2

List of Examples

| Example | $R^{1a}$ | $R^{1b}$ | $R^5$ | $R^6$ | Mol. Weight |
|---------|----------|----------|-------|-------|-------------|
| 1 | H | H | (1,3-dioxolan-2-ylmethyl) | (2-(2-hydroxyethoxy)benzoyl) | 450,532 |
| 2 | H | H | (tetrahydropyran-2-ylmethyl) | (2-(2-hydroxyethoxy)benzoyl) | 462,586 |

TABLE 2-continued

List of Examples

| Example | R¹ᵃ | R¹ᵇ | R⁵ | R⁶ | Mol. Weight |
|---------|-----|-----|-----|-----|-------------|
| 3 | H | H | pyridin-4-yl-ethyl | 2-(carboxyphenoxy)ethyl | 455,555 |
| 4 | H | H | 4-(pyrrol-1-yl)butyl | 2-(carboxyphenoxy)ethyl | 471,597 |
| 5 | H | H | 4-(thiophen-2-yl)butyl | 2-(carboxyphenoxy)ethyl | 488,648 |
| 6 | H | H | 3-((1-methylimidazol-2-yl)thio)propyl | 2-(carboxyphenoxy)ethyl | 518,678 |
| 7 | H | H | 2-(2,5,5-trimethyl-1,3-dioxan-2-yl)ethyl | 2-(carboxyphenoxy)ethyl | 520,670 |
| 8 | H | H | thiophen-2-yl-methyl | 2-(carboxyphenoxy)ethyl | 460,60 |
| 9 | H | H | furan-2-yl-methyl | 2-(carboxyphenoxy)ethyl | 444,530 |

TABLE 2-continued

List of Examples

| Example | R¹ᵃ | R¹ᵇ | R⁵ | R⁶ | Mol. Weight |
|---|---|---|---|---|---|
| 10 | H | H | pyrrolidine-N-C(O)-CH₂-* | 2-(HOOC)-C₆H₄-O-CH₂CH₂-* | 475.585 |
| 11 | H | H | (thiophen-3-yl)-CH₂-* | 2-(HOOC)-C₆H₄-O-CH₂CH₂-* | 460.595 |
| 12 | H | H | (thiophen-2-yl)-CH₂CH₂-* | 2-(HOOC)-C₆H₄-O-CH₂CH₂-* | 474.622 |
| 13 | H | H | (thiophen-3-yl)-CH₂CH₂-* | 2-(HOOC)-C₆H₄-O-CH₂CH₂-* | 474.622 |
| 14 | H | H | (tetrahydrofuran-2-yl)-CH₂CH₂CH₂-* | 2-(HOOC)-C₆H₄-O-CH₂CH₂-* | 476.613 |
| 15 | H | H | (1,3-dioxolan-2-yl)-CH₂CH₂CH₂CH₂-* | 2-(HOOC)-C₆H₄-O-CH₂CH₂-* | 492.612 |
| 16 | H | H | (benzo[1,3]dioxol-5-yl)-O-CH₂CH₂CH₂-* | 2-(HOOC)-C₆H₄-O-CH₂CH₂-* | 542.628 |

TABLE 2-continued
List of Examples
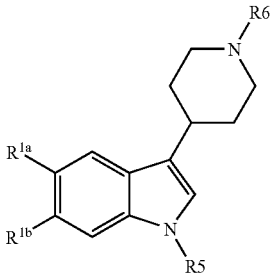
| Example | $R^{1a}$ | $R^{1b}$ | $R^5$ | $R^6$ | Mol. Weight |
|---------|----------|----------|-------|-------|-------------|
| 17 | H | H |  | 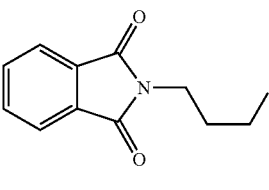 | 551,639 |
| 18 | H | H | 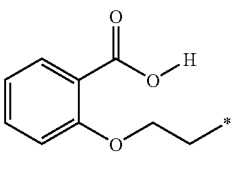 | 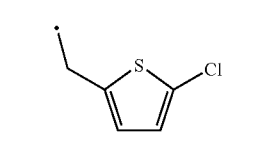 | 498,576 |
| 19 | H | H | 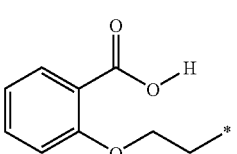 | 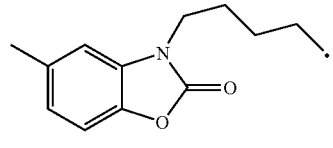 | 495,040 |
| 20 | H | H | 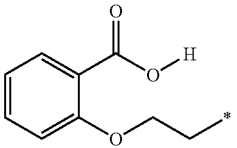 | 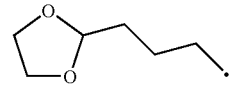 | 567,682 |
| 21 | H | H | 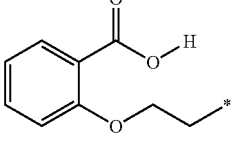 | 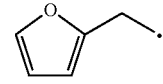 | 478,590 |
| 22 | H | F | 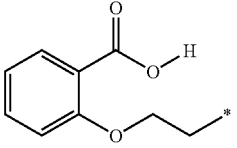 | 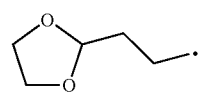 | 462,520 |
| 23 | H | H | 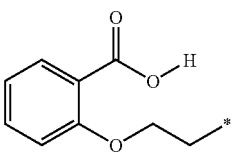 | | 464,560 |

TABLE 2-continued

List of Examples

| Example | R¹ᵃ | R¹ᵇ | R⁵ | R⁶ | Mol. Weight |
|---|---|---|---|---|---|
| 24 | H | F | 2-(1,3-dioxolan-2-yl)ethyl | 2-(carboxyphenoxy)propyl | 482,550 |
| 25 | H | H | thiophen-2-ylmethyl | 3-carboxybenzyl | 430,569 |
| 26 | H | H | pyridin-3-ylmethyl | 3-carboxybenzyl | 425,529 |
| 27 | H | H | 5-chlorothiophen-2-ylmethyl | 3-carboxybenzyl | 465,015 |
| 28 | H | H | 2-(1,3-dioxolan-2-yl)ethyl | 3-carboxybenzyl | 434,533 |
| 29 | H | H | 3-(1,3-dioxolan-2-yl)propyl | 3-carboxybenzyl | 448,560 |
| 30 | H | H | pyridin-4-ylmethyl | 3-carboxybenzyl | 425,529 |

TABLE 2-continued
List of Examples
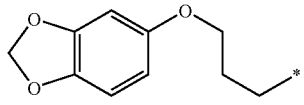
| Example | R¹ᵃ | R¹ᵇ | R⁵ | R⁶ | Mol. Weight |
|---|---|---|---|---|---|
| 31 | H | H | 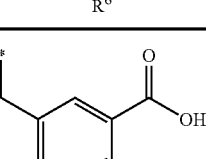 | 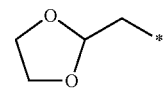 | 512,603 |
| 32 | H | H | 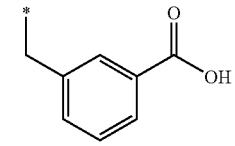 | 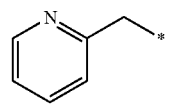 | 420,506 |
| 33 | H | H | 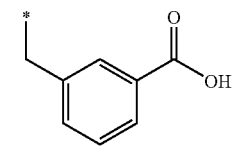 | 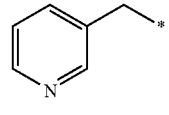 | 425,529 |
| 34 | H | H | 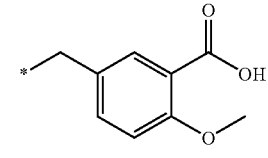 | 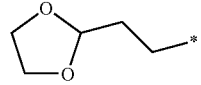 | 455,555 |
| 35 | H | H | 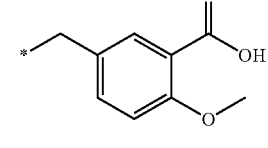 | 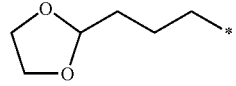 | 464,559 |
| 36 | H | H | 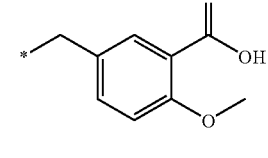 | 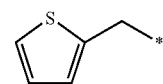 | 478,586 |
| 37 | H | H | 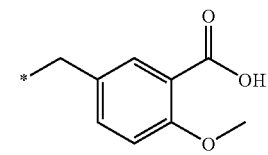 | | 460,595 |

TABLE 2-continued
List of Examples
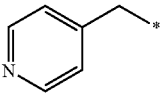
| Example | R¹ᵃ | R¹ᵇ | R⁵ | R⁶ | Mol. Weight |
|---|---|---|---|---|---|
| 38 | H | H | 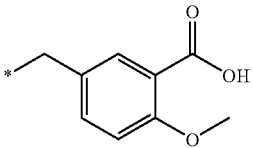 | 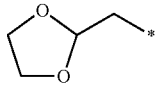 | 455,555 |
| 39 | H | H | 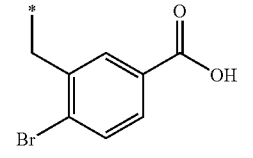 | 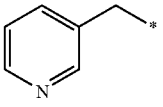 | 499,402 |
| 40 | H | H | 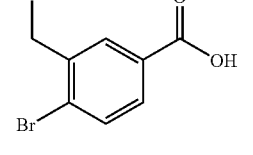 | 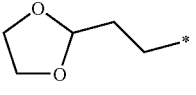 | 504,425 |
| 41 | H | H | 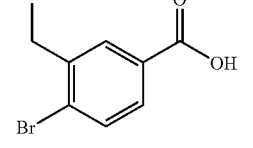 | 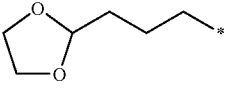 | 513,429 |
| 42 | H | H | 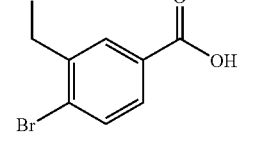 | 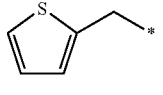 | 527,456 |
| 43 | H | H | 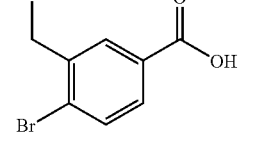 | 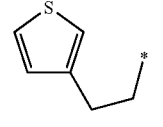 | 509,466 |
| 44 | OMe | H | 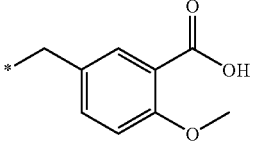 | | 474,624 |

TABLE 2-continued
List of Examples
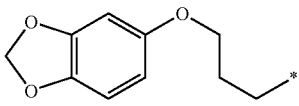
| Example | R¹ᵃ | R¹ᵇ | R⁵ | R⁶ | Mol. Weight |
|---|---|---|---|---|---|
| 45 | H | H | 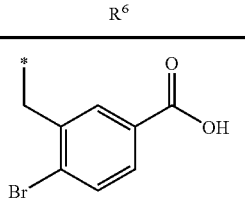 | 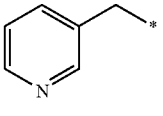 | 591,499 |
| 46 | H | H | 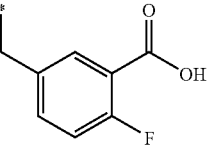 | 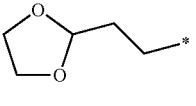 | 443,519 |
| 47 | H | H | 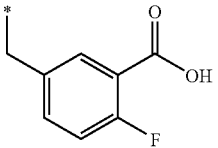 | 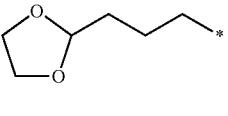 | 452,523 |
| 48 | H | H | 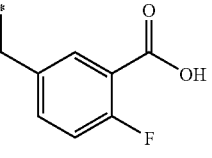 | 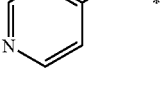 | 466,550 |
| 49 | H | H | 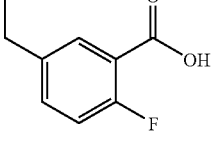 | 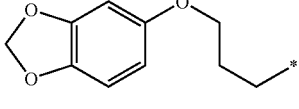 | 443,519 |
| 50 | H | H | 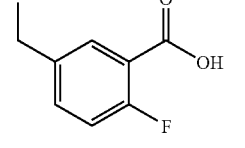 | 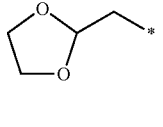 | 530,593 |
| 51 | H | H | 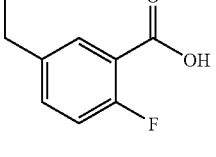 | | 438,496 |

TABLE 2-continued
List of Examples
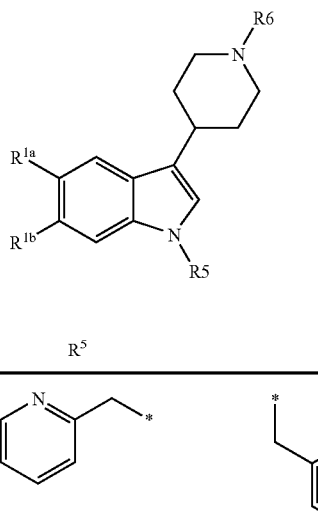
| Example | R$^{1a}$ | R$^{1b}$ | R$^5$ | R$^6$ | Mol. Weight |
|---|---|---|---|---|---|
| 52 | H | H |  | 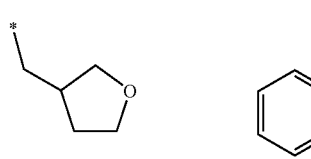 | 443,519 |
| 53 | H | H | 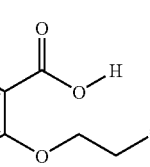 | 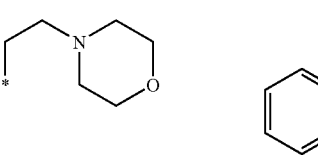 | 448,560 |
| 54 | H | H | 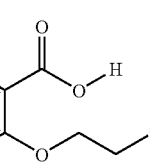 | 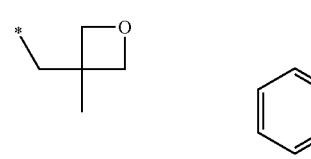 | 477,601 |
| 55 | H | H | 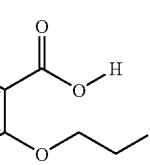 | 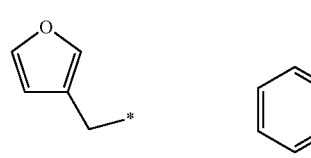 | 448,560 |
| 56 | H | H | 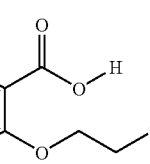 | 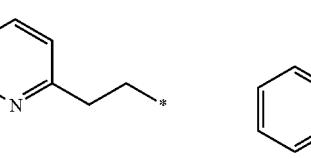 | 444,528 |
| 57 | H | H | 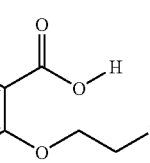 | 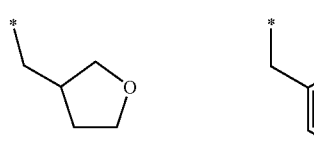 | 469,582 |
| 58 | H | H | 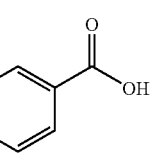 |  | 418,534 |

TABLE 2-continued

List of Examples

| Example | R¹ᵃ | R¹ᵇ | R⁵ | R⁶ | Mol. Weight |
|---|---|---|---|---|---|
| 59 | H | H | 3-methyl-3-oxetanyl-methyl | 3-carboxybenzyl | 418.534 |
| 60 | H | H | 2-(thiophen-3-yl)ethyl | 3-carboxybenzyl | 444.596 |
| 61 | H | H | furan-3-ylmethyl | 3-carboxybenzyl | 414.502 |
| 62 | H | H | pyridin-3-ylmethyl | 2-(3-carboxypyridyl)methyl | 426.517 |
| 63 | H | H | 2-morpholinoethyl | 2-(3-carboxypyridyl)methyl | 448.564 |
| 64 | H | H | thiophen-2-ylmethyl | 2-(3-carboxypyridyl)methyl | 431.558 |
| 65 | H | F | (5-chlorothiophen-2-yl)methyl | 3-carboxybenzyl | 483.005 |

TABLE 2-continued

List of Examples

| Example | R¹ᵃ | R¹ᵇ | R⁵ | R⁶ | Mol. Weight |
|---------|-----|-----|----|----|-------------|
| 66 | H | F | 3-thienyl-CH₂CH₂-* | *-CH₂-(3-carboxyphenyl) | 462.586 |
| 67 | H | F | 2-thienyl-CH₂CH₂-* | *-CH₂-(3-carboxyphenyl) | 462.586 |
| 68 | H | H | 2-thienyl-CH₂CH₂-* | *-CH₂-(3-carboxy-4-methoxyphenyl) | 474.622 |
| 69 | H | F | 2-thienyl-CH₂CH₂-* | *-CH₂-(3-carboxy-4-methoxyphenyl) | 492.612 |
| 70 | H | F | *-CH₂CH₂-morpholinyl | *-CH₂-(3-carboxy-4-methoxyphenyl) | 495.592 |
| 71 | H | H | 1,3-dioxanyl-CH₂CH₂-* | *-CH₂-(3-carboxy-4-methoxyphenyl) | 478.586 |
| 72 | H | H | 1,3-dioxanyl-CH₂CH₂-* | *-CH₂-(3-carboxyphenyl) | 448.560 |

TABLE 2-continued
List of Examples
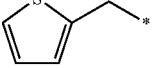
| Example | R¹ᵃ | R¹ᵇ | R⁵ | R⁶ | Mol. Weight |
|---|---|---|---|---|---|
| 73 | H | H | 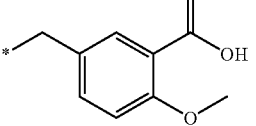 | 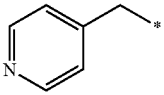 | 460,595 |
| 74 | H | H | 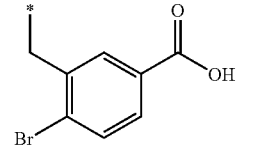 | 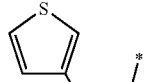 | 504,425 |
| 75 | H | H | 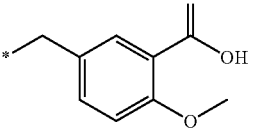 | 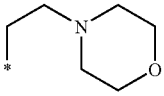 | 474,622 |
| 76 | H | H | 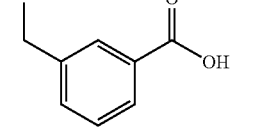 | 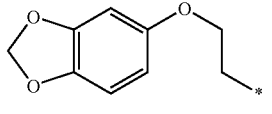 | 447,576 |
| 77 | H | H | 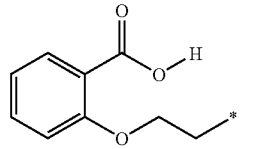 | 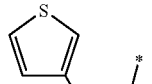 | 528,602 |
| 78 | H | F | 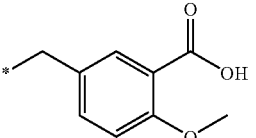 | 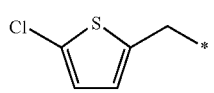 | 492,612 |
| 79 | H | F | 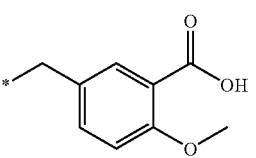 | | 513,030 |

TABLE 2-continued
List of Examples
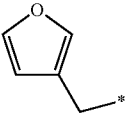
| Example | R¹ᵃ | R¹ᵇ | R⁵ | R⁶ | Mol. Weight |
|---|---|---|---|---|---|
| 80 | H | F | 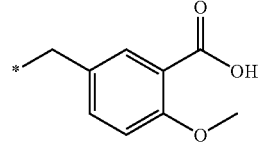 | 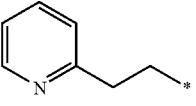 | 462,518 |
| 81 | H | H | 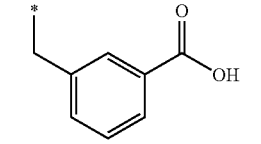 | 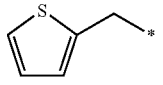 | 439,556 |
| 82 | H | F | 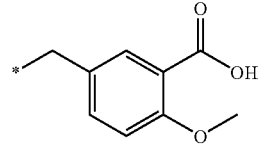 | 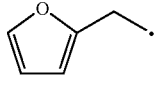 | 478,585 |
| 83 | H | H | 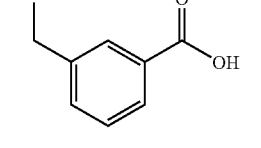 | 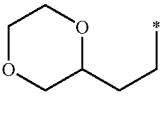 | 414,502 |
| 84 | H | H | 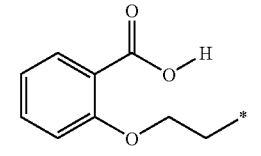 | 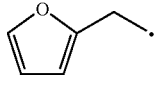 | 478,586 |
| 85 | H | H | 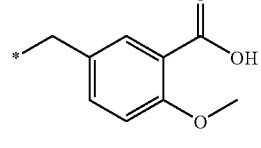 | 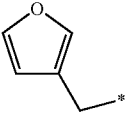 | 444,528 |
| 86 | H | H | 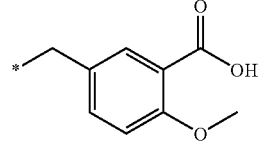 | | 444,528 |

TABLE 2-continued

List of Examples

| Example | R¹ᵃ | R¹ᵇ | R⁵ | R⁶ | Mol. Weight |
|---------|-----|-----|----|----|-------------|
| 87 | OMe | H | thiophen-3-yl-ethyl | 3-(carboxy)benzyl | 474.622 |
| 88 | OMe | H | thiophen-3-yl-ethyl | 2-(2-carboxyphenoxy)ethyl | 504.648 |
| 89 | OMe | H | thiophen-2-yl-methyl | 2-(2-carboxyphenoxy)ethyl | 490.621 |
| 90 | OMe | H | thiophen-2-yl-methyl | 3-(carboxy)benzyl | 460.595 |
| 91 | OMe | H | thiophen-3-yl-ethyl | 3-carboxy-4-methoxybenzyl | 504.648 |
| 92 | OMe | H | furan-3-yl-methyl | 2-(2-carboxyphenoxy)ethyl | 474.554 |
| 93 | OMe | H | furan-3-yl-methyl | 3-(carboxy)benzyl | 444.528 |

TABLE 2-continued
List of Examples
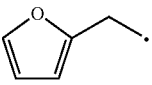
| Example | R¹ᵃ | R¹ᵇ | R⁵ | R⁶ | Mol. Weight |
|---------|-----|-----|----|----|-------------|
| 94 | H | H | 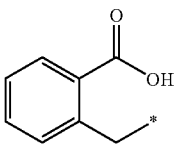 | 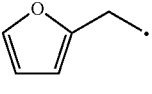 | 414.502 |
| 95 | H | F | 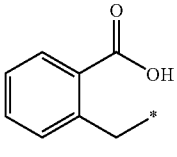 | 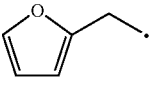 | 432.493 |
| 96 | H | F | 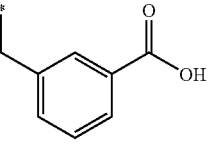 | 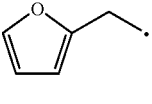 | 432.493 |
| 97 | H | F | 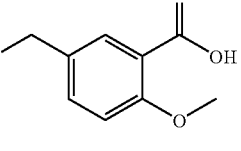 | 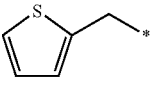 | 462.518 |
| 98 | OMe | H | 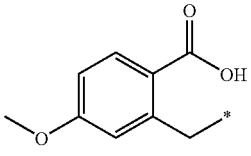 | 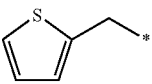 | 490.621 |
| 99 | OMe | H | 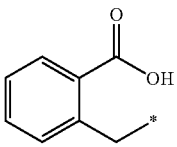 | 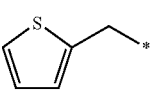 | 460.595 |
| 100 | OMe | H | 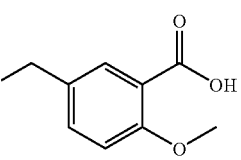 | | 490.621 |

TABLE 2-continued
List of Examples
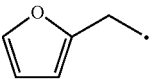
| Example | R¹ᵃ | R¹ᵇ | R⁵ | R⁶ | Mol. Weight |
|---|---|---|---|---|---|
| 101 | OMe | H | 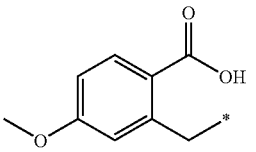 | 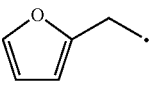 | 474,554 |
| 102 | OMe | H | 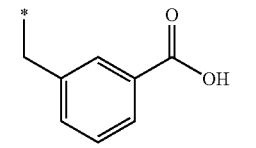 | 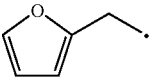 | 444,528 |
| 103 | OMe | H | 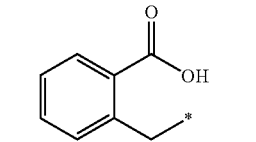 | 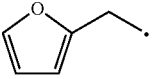 | 444,528 |
| 104 | OMe | H | 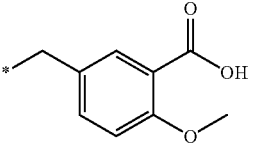 | 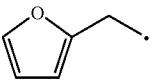 | 474,554 |
| 105 | OMe | H | 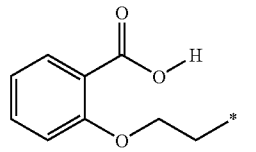 | 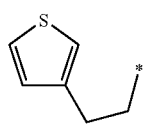 | 474,554 |
| 106 | OMe | H | 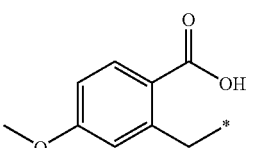 | 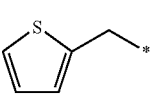 | 504,648 |
| 107 | H | F | 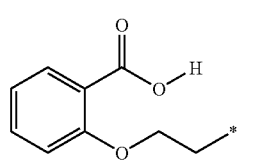 | | 478,585 |

TABLE 2-continued

List of Examples

| Example | R¹ᵃ | R¹ᵇ | R⁵ | R⁶ | Mol. Weight |
|---------|-----|-----|----|----|-------------|
| 108 | H | F | thiophen-3-ylmethyl | 3-(methylene)-6-methoxybenzoic acid (2-methoxy-5-methylenebenzoic acid) | 478.585 |
| 109 | H | F | thiophen-3-ylmethyl | 2-(2-aminoethoxy)benzoic acid amide linker | 478.585 |
| 110 | H | F | 2-(thiophen-3-yl)ethyl | 2-(2-aminoethoxy)benzoic acid amide linker | 492.612 |
| 111 | H | F | (5-chlorothiophen-2-yl)methyl | 2-(2-aminoethoxy)benzoic acid amide linker | 513.030 |
| 112 | H | F | furan-3-ylmethyl | 2-(2-aminoethoxy)benzoic acid amide linker | 462.518 |
| 113 | OMe | H | thiophen-3-ylmethyl | 2-(2-aminoethoxy)benzoic acid amide linker | 490.621 |
| 114 | OMe | H | thiophen-3-ylmethyl | 3-(methylene)benzoic acid | 460.595 |

TABLE 2-continued
List of Examples
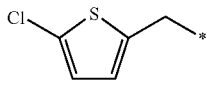
| Example | R¹ᵃ | R¹ᵇ | R⁵ | R⁶ | Mol. Weight |
|---|---|---|---|---|---|
| 115 | OMe | H | 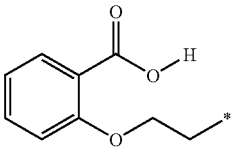 | 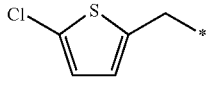 | 525,066 |
| 116 | OMe | H | 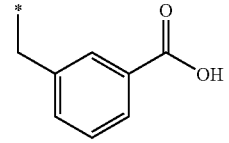 | 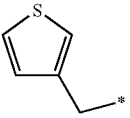 | 495,040 |
| 117 | H | H | 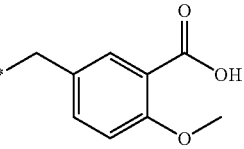 | 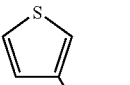 | 460,595 |
| 118 | H | H | 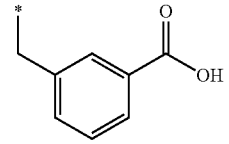 | 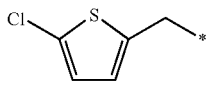 | 430,569 |
| 119 | OMe | H | 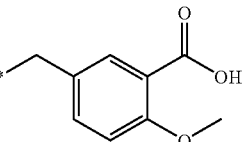 | 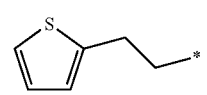 | 525,066 |
| 120 | OMe | H | 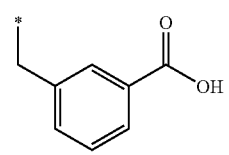 | 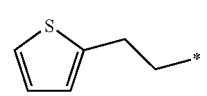 | 474,622 |
| 121 | OMe | H | 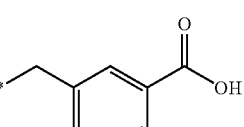 | | 504,647 |
The sign (*) in the structure shows only the binding point but it does not symbolise a carbon atom.

EXAMPLE 1

Preparation of 2-{2-[4-(1-[1,3]dioxolan-2-ylmethyl-1H-indol-3-yl)-piperidin-1-yl]-ethoxy}-benzoic acid A. Preparation of 3-(1,2,3,6-tetrahydro-pyridin-4-yl)-1H-indole 30 g (0.26 mol) of indole was dissolved in a solution of potassium hydroxide (77.6 g, 1.38 mol) in methanol (692 ml). 4-piperidone monohydrate hydrochloride (102.3 g, 0.66 mol) was added in one portion and the mixture was heated to reflux for 5 h. Potassium chloride precipitated upon cooling at room temperature and it was filtered off. The liquid phase was concentrated until only one third of the liquid remained in the round-bottom flask. The solid formed during the concentration of the liquid phase was filtered and washed thoroughly with ethanol and, finally, with ethyl ether. 31.9 g (63% of yield) of the final product were obtained.

Melting point=183–185° C.

B. Preparation of 3-piperidin-4-yl-1H-indole 19.03 g (0.096 mol) of 3-(1,2,3,6-tetrahydro-pyridin-4-yl)-1H-indole were hydrogenated in a Parr apparatus during 18 h at 40 psi with 2.2 g of Pd/C 10% in 600 ml of methanol. After standard work-up, 16.76 g (87% of yield) of the desired product were obtained.

Melting point=210–212° C.

C. Preparation of 2-(2-chloro-ethoxy)-benzoic acid methyl ester 34 g (0.25 mol) of potassium carbonate were added to a solution of 25 g (0.16 mol) of methyl salicylate in 250 ml of methyl ethyl ketone. This mixture was refluxed for 1 h, then 27.3 ml (0.35 mol) of 1-bromo-2-chloro-ethane were added and the mixture was taken to reflux again. Four hours later, 34 g (0.25 mol) more of potassium carbonate and 16.3 ml (0.2 mol) more of 1-bromo-2-chloro-ethane were added. This operation was repeated until the reaction was completed. The inorganic salts were filtered off and the liquid phase was diluted with the same volume of hexane. This organic phase was washed twice with water and worked-up as usual. The yield in this step was quantitative and the product was pure enough for the next synthetic step.

NMR (300 MHz, $CDCl_3$) $\delta$=3.86–3.90 (m, 5H), 4.28–4.33 (t, 2H), 6.96–7.09 (m, 2H), 7.43–7.51 (m, 1H), 7.78–7.83 (m, 1H).

D. Preparation of 2-{2-[4-(1H-indol-3-yl)-piperidin-1-yl]-ethoxy}-benzoic acid methyl ester 0.14 g (0.65 mmol) of 2-(2-chloro-ethoxy)-benzoic acid methyl ester were added to a mixture of 0.1 g (0.5 mmol) of 3-piperidin-4-yl-1H-indole, 0.10 g (0.75 mmol) of potassium carbonate and 0.06 g (0.37 mmol) of potassium iodide in 1.5 mL of isobutyl methyl ketone under nitrogen atmosphere and the reaction mixture was refluxed for 18 hours. After cooling at room temperature, 1.5 mL of dichloromethane and 0.08 g (0.1 mmol) of polystyrene methyl isocyanate were added and the mixture was stirred at this temperature for 3 hours. After filtering, the solution was placed directly onto a 500 mg Varian SCX ion exchange column. The columns were washed with 5 mL of methanol and the product was eluted with 5 mL of methanol/ammonia 20:1 affording, after removal of the solvent at reduced pressure, 0.113 g (60% yield) of 2-{2-[4-(1H-indol-3-yl)-piperidin-1-yl]-ethoxy}-benzoic acid methyl ester as a yellow oil.

ESI/MS m/e=379 [$(M+1)^+$, C23 H26 N2 O3]

E. Preparation 2-{2-[4-(1-[1,3]dioxolan-2-ylmethyl-1H-indol-3-yl)-piperidin-1-yl]-ethoxy}-benzoic acid 0.02 g (0.42 mmol) of a dispersion of 60% NaH in mineral oil were added to a solution of 0.06 g (0.16 mmol) of 2-{2-[4-(1H-indol-3-yl)-piperidin-1-yl]-ethoxy}-benzoic acid methyl ester prepared in step D in 1 mL of anhydrous DMF under an inert atmosphere. After stirring 30 minutes at room temperature, 0.04 mg (0.24 mmol) of 2-bromomethyl-[1,3]dioxolane were added and the mixture was stirred for 18 hours. The solvent was removed under reduced pressure and the crude mixture was dissolved in 1 mL of ethanol. 0.1 mL of 2N NaOH were added and the mixture was stirred at 60° C. for 3 hours. 0.1 mL of 2N HCl were added and the reaction mixture was stirred at room temperature for 1 hour. The solvent was removed under reduced pressure and the crude mixture was purified using a 500 mg Varian C18 chromatography column, affording 0.040 g (56% yield) of 2-{2-[4-(1-[1,3]dioxolan-2-ylmethyl-1H-indol-3-yl)-piperidin-1-yl]-ethoxy}-benzoic acid.

Melting point 139–141° C.

NMR (300 MHz, DMSO) $\delta$=1.90–2.10 (m, 4H), 2.58–2.72 (m, 2H), 2.90–2.98 (m, 3H), 3.20–3.24 (m, 2H), 3.76–3.80 (m, 4H), 4.25–4.27 (m, 2H), 4.41–4.45 (m, 2H), 5.09–5.13 (m, 1H), 7.00–7.12 (m, 2H), 7.12 (s, 2H), 7.38–7.54 (m, 4H), 7.63–7.65 (d, 1H).

EXAMPLES 2–10, 17 AND 20

These examples were prepared following the procedure described in Example 1 (parts D and E). The ESI/MS data and yields are summarised in table 3.

TABLE 3

Examples 2–10, 17 and 20

| Example | ESI/MS m/e [$(M + 1)^+$] | Yield % (mg obtained) | Purity % |
|---|---|---|---|
| 2 | 463 | 48 (36 mg) | 92 |
| 3 | 456 | 19 (14 mg) | 71 |
| 4 | 472 | 25 (19 mg) | 96 |
| 5 | 489 | 10 (7 mg) | 99 |
| 6 | 519 | 22 (18 mg) | 92 |
| 7 | 521 | 21 (32 mg) | 72 |
| 8 | 461 | 17 (21 mg) | 77 |
| 9 | 445 | 42 (50 mg) | 96 |
| 10 | 476 | 32 (30 mg) | 87 |
| 17 | 552 | 13 (14 mg) | 76 |
| 20 | 568 | 52 (59 mg) | 32 |

EXAMPLE 13

Preparation of 2-(2-{4-[1-(2-thiophen-3-yl-ethyl)-1H-indol-3-yl]-piperidin-1-yl}-ethoxy)-benzoic acid A. Preparation of 4-(1H-indol-3-yl)-piperidine-1-carboxylic acid ethyl ester To a suspension of 30 g (0.15 mol) of 3-piperidin-4-yl-1H-indole and 28 mL (0.2 mol) in 185 mL of anhydrous dichloromethane, 17 mL (0.18 mol) of ethyl chloroformate was added dropwise keeping the temperature of the reaction below 20° C. After 2 h at room temperature, the crude mixture was poured into 100 mL of water. The organic layer was separated and dried with sodium sulfate. After filtration, the solvent was removed under reduced pressure affording 39 g (95% of yield) of the expected product.

ESI/MS m/e=272 [(M+1)⁺, C16 H20 N2 O2]

NMR (300 MHz, DMSO) δ=1.16–1.23 (t, 2H), 1.41–1.65 (m, 2H), 1.92–1.99 (m, 2H), 2.90–23.10 (m, 3H), 3.99–4.10 (m, 4H), 6.95–7.10 (m, 3H), 7.31–7.34 (d, 1H), 7.53–7.57 (d, 1H), 10.81 (s, 1H).

B. Preparation of 4-[1-(2-thiophen-3-yl-ethyl)-1H-indol-3-yl]-piperidine-1-carboxylic acid ethyl ester Under inert atmosphere, a solution of 6.9 g (0.025 mol) of 4-(1H-indol-3-yl)-piperidine-1-carboxylic acid ethyl ester in 25 mL of anhydrous DMF was added dropwise to a suspension containing 1.2 g (0.030 mol) of sodium hydride (60% in mineral oil) in 70 mL of anhydrous DMF. After stirring at room temperature for 1 hour, a solution of 6.2 g (0.03 mol) of 2-thiophen-3-yl-ethyl methansulfonate in 15 mL of anhydrous DMF was added. The reaction mixture was stirred at room temperature for 30 minutes and then heated at 60° for 3 hours. The crude mixture was poured into water and extracted with dichloromethane. After drying, the solvent was removed under reduced pressure and 10.3 g of a crude oil were obtained. The crude mixture was purified by flash chromatography over silica gel affording 8.3 g (86% of yield) of the expected product.

C. Preparation of 3-piperidin-4-yl-1-(2-thiophen-3-yl-ethyl)-1H-indole

To a solution of 12.7 g (0.033 mol) of 4-[1-(2-thiophen-3-yl-ethyl)-1H-indol-3-yl]-piperidine-1-carboxylic acid ethyl ester in 10 mL of iso-propanol, a solution of 22 g of potassium hydroxide in 220 mL of iso-propanol was added. The crude mixture was refluxed for 16 hours. After cooling at room temperature, the solvent was removed at reduced pressure and the crude mixture was extracted between toluene and water. The organic layer was dried with sodium sulfate and after filtration, the solvent was removed under reduced pressure affording 9.3 g (90% of yield) of an oil which corresponds to the expected product.

D. Preparation of 2-(2-{4-[1-(2-thiophen-3-yl-ethyl)-1H-indol-3-yl]-piperidin-1-yl}-ethoxy)-benzoic acid A solution of 1.5 g (0.007 mol) of 2-(2-chloro-ethoxy)-benzoic acid methyl ester (prepared in Example 1, part C) in 5 mL of methyl-iso-butylketone was added to a suspension of 2 g (0.065 mol) of 3-piperidin-4-yl-1-(2-thiophen-3-yl-ethyl)-1H-indole and 1.8 g (0.013 mol) of potassium carbonate in 45 mL of methyl-iso-butylketone. The reaction mixture was refluxed for 18 h. The crude mixture was filtered to remove inorganic salts and the solvent was removed under reduced pressure affording 3.3 g of a crude oil. The crude mixture was purified by flash chromatography over silica gel affording 1.5 g (48% of yield) of 2-(2-{4-[1-(2-thiophen-3-yl-ethyl)-1H-indol-3-yl]-piperidin-1-yl}-ethoxy)-benzoic acid methyl ester. This ester was dissolved in a mixture of 25 mL of methanol/THF 3:2 and hydrolysed with 2N NaOH at room temperature for 16 hours. The crude mixture was neutralised with 2N HCl aqueous solution and the solvent was removed under reduced pressure. The crude residue was precipitated with dichloromethane and then recrystallised with methanol affording 1.3 g of the expected acid.

Melting point 165–167° C.

NMR (300 MHz, DMSO) δ=1.75–2.07 (m, 4H), 2.54–2.65 (m, 2H), 2.77–3.00 (m, 3H), 3.00–3.13 (t, 2H), 3.14–3.30 (m, 2H), 4.25–4.39 (t, 2H), 4.39–4.55 (m, 2H), 5.20–5.40 (m, 1H), 6.93–7.29 (m, 7H), 7.33–7.59 (m, 4H), 7.59–7.67 (d, 1H).

EXAMPLES 11, 12, 14, 15, AND 18

These examples were prepared following the procedure described in Example 13 using the suitable methansulfonate or bromide in part B. The ESI/MS data and yields are summarised in table 4.

TABLE 4

Examples 11, 12, 14, 15, and 18

| Example | ESI/MS m/e [(M + 1)⁺] | Yield % (mg obtained) | Purity % |
|---|---|---|---|
| 11 | 461 | 11 (9 mg) | 88 |
| 12 | 475 | 10 (2 mg) | 92 |
| 14 | 477 | 33 (29 mg) | 33 |
| 15 | 493 | 10 (9 mg) | 95 |
| 18 | 499 | 10 (9 mg) | 77 |

EXAMPLE 16

Preparation of 2-[2-(4-{1-[3-(benzo[1,3]dioxol-5-yloxy)propyl]-1H-indol-3-yl}piperidin-1-yl)ethoxy]benzoic acid A. Preparation of 4-{1-[3-(benzo[1,3]dioxol-5-yloxy)-propyl]-1H-indol-3-yl}-piperidine-1-carboxylic acid ethyl ester This compound was prepared following the procedure described in example 13 (part B) at room temperature for 15 hours, starting with 2.2 g (8.1 mmol) of 4-(1H-indol-3-yl)-piperidine-1-carboxylic acid ethyl ester and 2.68 g (10 mmol) of 5-(3-bromo-propoxy)-benzo[1,3]dioxole. After standard work-up, 3.8 g (100% of yield) of the expected product was obtained.

B. Preparation of 1-[3-(benzo[1,3]dioxol-5-yloxy)-propyl]-3-piperidin-4-yl-1H-indole This compound was prepared following the procedure described in example 13 (part C) starting with 2.68 g (8.1 mmol) of 4-{1-[3-(benzo[1,3]dioxol-5-yloxy)-propyl]-1H-indol-3-yl}-piperidine-1-carboxylic acid ethyl ester.

C. Preparation of 2-[2-(4-{1-[3-(benzo[1,3]dioxol-5-yloxy)propyl]-1H-indol-3-yl}piperidin-1-yl)ethoxy]benzoic acid This compound was prepared following the procedure described in example 13 (part D), starting with 8.1 mmol of 1-[3-(benzo[1,3]dioxol-5-yloxy)-propyl]-3-piperidin-4-yl-1H-indole and 2.3 g (11 mmol) of of 2-(2-chloro-ethoxy)-benzoic acid methyl ester. After the standard work-up, 2.68 g of the corresponding acid was obtained. The crude mixture was purified by flash chromatography over silica gel affording 1.15 g (26% of yield) of the expected acid.

Melting point 147–152° C.

NMR (300 MHz, DMSO) δ=1.70–2.00 (m, 4H), 2.07–2.16 (m, 2H), 2.60–2.68 (m, 2H), 2.81–2.97 (m, 3H), 3.16–3.24 (m, 2H), 3.76–3.82 (m, 2H), 4.25–4.30 (t, 2H), 4.31–4.35 (m, 2H), 4.30–4.70 (m, 1H), 5.94 (s, 2H), 6.32–6.36 (dd, 1H), 6.62–6.63 (m, 1H), 6.78–6.80 (d, 1H), 6.96–7.13 (m, 4H), 7.21–7.24 (m, 1H), 7.36–7.40 (m, 2H), 7.51–7.54 (m, 1H), 7.63–7.66 (d, 1H).

EXAMPLE 19

Preparation of 2-(2-{4-[1-(5-chloro-thiophen-2-ylmethyl)-1H-indol-3-yl]-piperidin-1-yl}-ethoxy)-benzoic acid A. Preparation of 4-[1-(5-chloro-thiophen-2-ylmethyl)-1H-indol-3-yl]-piperidine-1-carboxylic acid ethyl ester This compound was prepared following the procedure described in example 13 (part B) at room temperature for 15 hours, starting with 3.5 g (13 mmol) of 4-(1H-indol-3-yl)-piperidine-1-carboxylic acid ethyl ester and 1.9 mL (16 mmol) of 2-chloro-5-chloromethyl-thiophene. After standard work-up, 5.2 g (99% of yield) of the expected product was obtained.

B. Preparation of 1-(5-chloro-thiophen-2-ylmethyl)-3-piperidin-4-yl-1H-indole

This compound was prepared following the procedure described in example 13 (part C) starting with 5.21 g (13 mmol) of 4-[1-(5-chloro-thiophen-2-ylmethyl)-1H-indol-3-yl]-piperidine-1-carboxylic acid ethyl ester. After standard work-up 4.19 g (97% of yield) of the expected product were obtained.

C. Preparation of 2-(2-{4-[1-(5-chloro-thiophen-2-ylmethyl)-1H-indol-3-yl]-piperidin-1-yl}-ethoxy)-benzoic acid This compound was prepared following the procedure described in example 13 (part D), starting with 4.21 mmol (13 mmol) of 1-(5-chloro-thiophen-2-ylmethyl)-3-piperidin-4-yl-1H-indole and 3.6 g (17 mmol) of of 2-(2-chloro-ethoxy)-benzoic acid methyl ester. After the standard work-up, 2.47 g of the corresponding acid was obtained. The crude mixture was purified by flash chromatography over silica gel affording 1.2 g (17% of yield) of the pure acid.

Melting point 178–179° C.

NMR (300 MHz, DMSO) δ=1.86–2.05 (m, 4H), 2.58–2.69 (m, 2H), 2.87–2.98 (m, 3H), 3.17–3.23 (m, 2H), 4.41–4.45 (m, 2H), 5.50 (s, 2H), 5.40–5.80 (m, 1H), 6.95–7.05 (m, 4H), 7.10–7.16 (m, 1H), 7.21–7.24 (m, 2H), 7.36–7.41 (m, 1H), 7.47–7.55 (m, 2H), 7.64–7.68 (d, 1H).

EXAMPLE 21

Preparation of 2-(2-{4-[1-(3-[1,3]dioxolan-2-yl-propyl)-1H-indol-3-yl]-piperidin-1-yl}-ethoxy)-benzoic acid A solution of 2.75 g (7 mmol) of 2-{2-[4-(1H-indol-3-yl)-piperidin-1-yl]-ethoxy}-benzoic acid methyl ester (prepared as in Example 1, part D) in 10 mL of anhydrous DMF was added to a suspension of 0.36 g (9.1 mmol) of a NaH (60% dispersion in mineral oil) in 5 mL of anhydrous DMF under an inert atmosphere. After stirring for 30 minutes at room temperature, a solution of 1.1 mL (8.4 mmol) of 2-(3-chloro-propyl)-[1,3]dioxolane in 3 mL of DMF was added. The crude mixture was stirred at room temperature for 16 hours and the solvent was removed under reduced pressure. The residue obtained was dissolved with 150 mL of ethanol and 6 mL of a 2N NaOH aqueous solution were added. After 12 h at room temperature, the solvent was removed under reduced pressure. The crude mixture was dissolved with 50 mL of water and neutralised with a 2N HCl aqueous solution. The crude mixture was purified by flash chromatography over silica gel affording 0.83 g (29% of yield) of the expected product.

Melting point 147–149° C.

NMR (300 MHz, DMSO) δ=1.50–1.56 (m, 2H), 1.75–1.86 (m, 2H), 1.89–1.97 (m, 4H), 2.61–2.69 (m, 2H), 2.79–2.99 (m, 3H), 3.21–3.24 (d, 2H), 3.70–3.75 (m, 2H), 3.82–3.87 (m, 2H), 4.13–4.17 (m, 2H), 4.42–4.46 (m, 2H), 4.76–4.80 (m, 1H), 5.00–5.40 (bs, 1H), 6.99–7.02 (m, 2H), 7.10–7.24 (m, 3H), 7.37–7.43 (m, 2H), 7.52–7.54 (d, 1H), 7.64–7.66 (d, 1H).

EXAMPLE 22

Preparation of 2-{2-[4-(6-fluoro-1-furan-2-ylmethyl-1H-indol-3-yl)-piperidin-1-yl]-ethoxy}-benzoic acid A. Preparation of 6-fluoro-3-piperidin-4-yl-1H-indole This compound was prepared following the procedure described in example 1 (parts A and B) starting with 1 g (7.4 mmol) of 6-fluoroindol and 2.84 g (18.5 mmol) of 4-piperidone monohydrate hydrochloride. In this case, the hydrogenation step took place for 1 hour at 30 psi and the catalyst used was platinum (IV) oxide. 0.640 g (51% yield) of 6-fluoro-3-piperidin-4-yl-1H-indole were obtained.

ESI/MS m/e=219 [(M+1)$^+$, C13 H15 F N2]

B. Preparation of 4-(6-fluoro-1H-indol-3-yl)-piperidine-1-carboxylic acid ethyl ester This compound was prepared following the procedure described in example 13 (part A) starting with 4.4 g (20 mmol) of 6-fluoro-3-piperidin-4-yl-1H-indole. After standard work-up, 5.2 g (90% of yield) of 4-(6-fluoro-1H-indol-3-yl)-piperidine-1-carboxylic acid ethyl ester were obtained.

C. Preparation of 4-(6-fluoro-1-furan-2-ylmethyl-1H-indol-3-yl)-piperidine-1-carboxylic acid ethyl ester This compound was obtained following procedure described in example 13 (part B) at room temperature for 5 hours, starting with 5 g (17.2 mmol) of 4-(6-fluoro-1H-indol-3-yl)-piperidine-1-carboxylic acid ethyl ester were and 3.2 g (20 mmol) of 2-bromomethyl-furan. After standard work-up, 6.4 g (99% of yield) of 4-(6-fluoro-1-furan-2-ylmethyl-1H-indol-3-yl)-piperidine-1-carboxylic acid ethyl ester were obtained.

D. Preparation of 6-fluoro-1-furan-2-ylmethyl-3-piperidin-4-yl-1H-indole

This compound was prepared following the procedure described in example 13 (part C) starting with 6.4 g (17.2 mmol) of 4-(6-fluoro-1-furan-2-ylmethyl-1H-indol-3-yl)-piperidine-1-carboxylic acid ethyl ester. After standard work-up, 4.4 g (86% of yield) of 6-fluoro-1-furan-2-ylmethyl-3-piperidin-4-yl-1H-indole were obtained.

E. Preparation of 2-{2-[4-(6-fluoro-1-furan-2-ylmethyl-1H-indol-3-yl)-piperidin-1-yl]-ethoxy}-benzoic acid This compound was prepared following the procedure described in example 13 (part E) starting with 2 g (6.5 mmol) of 6-fluoro-1-furan-2-ylmethyl-3-piperidin-4-yl-1H-indole and 1.5 g (7.1 mmol) of 2-(2-chloro-ethoxy)-benzoic acid methyl ester. After standard work-up and purification by flash chromatography over silica gel, 0.9 g (30% of yield) of the expected acid were obtained.

Melting point 174–175° C.

NMR (300 MHz, DMSO) δ=1.83–1.95 (m, 4H), 2.58–2.66 (m, 2H), 2.79–2.94 (m, 3H), 3.16–3.22 (d, 2H), 4.00–4.40 (bs, 1H), 4.33–4.39 (m, 2H), 5.35 (s, 2H), 6.40 (s, 1H), 6.45–6.47 (m, 1H), 6.97–7.66 (m, 10H).

EXAMPLE 23

Preparation of 2-(2-{4-[1-(2-[1,3]dioxolan-2-yl-ethyl)-1H-indol-3-yl]-piperidin-1-yl}-ethoxy)-benzoic acid A. Preparation of 4-[1-(2-[1,3]dioxolan-2-yl-ethyl)-1H-indol-3-yl]-piperidine-1-carboxylic acid ethyl ester This compound was prepared following the procedure described in example 13 (part B) at room temperature for 15 hours, starting with 4 g (0.015 mol) of 4-(1H-indol-3-yl)-piperidine-1-carboxylic acid ethyl ester and 2.07 mL (0.018 mol) of 2-(2-bromo-ethyl)-[1,3]dioxolane. After standard work-up, 5.3 g of 4-[1-(2-[1,3]dioxolan-2-yl-ethyl)-1H-indol-3-yl]-piperidine-1-carboxylic acid ethyl ester were obtained.

ESI/MS m/e=373 [(M+1)$^+$, C21 H28 N2 O4]

NMR (300 MHz, CDCl$_3$) δ=1.25–1.28 (t, 3H), 1.64–1.70 (m, 4H), 2.01–2.17 (m, 4H), 2.88–3.00 (m, 3H), 3.82–4.05 (m, 4H), 4.18–4.27 (m, 4H), 4.81–4.86 (t, 1H), 6.86 (s, 1H), 7.05–7.26 (m, 2H), 7.34–7.38 (d, 1H), 7.59–7.63 (d, 1H).

B. Preparation of 1-(2-[1,3]dioxolan-2-yl-ethyl)-3-piperidin-4-yl-1H-indole

This compound was obtained following the procedure described in example 13 (part C) starting with 5.3 g (0.018 mol) of 4-[1-(2-[1,3]dioxolan-2-yl-ethyl)-1H-indol-3-yl]-piperidine-1-carboxylic acid ethyl ester. After standard work-up, 4 g (89% of yield) of 1-(2-[1,3]dioxolan-2-yl-ethyl)-3-piperidin-4-yl-1H-indole were obtained.

ESI/MS m/e=301 [(M+1)$^+$, C18 H24 N2 O2]

NMR (300 MHz, CDCl$_3$) δ=1.61–1.76 (m, 2H), 2.01–2.21 (m, 5H), 2.74–3.02 (m, 3H), 3.16–3.22 (m, 2H), 3.82–4.04 (m, 4H), 4.20–4.4.27 (t, 2H), 4.81–4.86 (t, 1H), 6.87 (s, 1H), 7.07–7.25 (m, 2H), 7.32–7.36 (d, 1H), 7.61–7.65 (d, 1H).

C. Preparation of 2-(2-{4-[1-(2-[1,3]dioxolan-2-yl-ethyl)-1H-indol-3-yl]-piperidin-1-yl}-ethoxy)-benzoic acid This compound was prepared following the procedure described in example 13 (part D) starting with 3 g (0.01 mol) of 1-(2-[1,3]dioxolan-2-yl-ethyl)-3-piperidin-4-yl-1H-indole and 2.8 g (0.013 mol) of 2-(2-chloro-ethoxy)-benzoic acid methyl ester. The crude mixture was purified by flash chromatography over silica gel affording 1.86 g (40% of yield) of 2-(2-{4-[1-(2-[1,3]dioxolan-2-yl-ethyl-1H-indol-3-yl]-piperidin-1-yl}-ethoxy)-benzoic acid.

Melting point 118–120° C.

NMR (300 MHz, CDCl$_3$) δ=2.18–2.28 (m, 4H), 2.47–2.56 (m, 2H), 3.00–3.15 (m, 3H), 2.52–3.56 (m, 2H), 3.77–3.90 (m, 4H), 4.00–4.05 (m, 2H), 4.20–4.22 (t, 2H), 4.64–4.68 (m, 2H), 4.85–4.89 (m, 1H), 7.01–7.12 (m, 4H), 7.20–7.25 (t, 1H), 7.36–7.39 (d, 1H), 7.49–7.54 (t, 1H), 7.61–7.63 (d, 1H), 7.90–7.93 (d, 1H).

EXAMPLE 24

Preparation of 2-(2-{4-[1-(2-[1,3]dioxolan-2-yl-ethyl)-6-fluoro-1H-indol-3-yl]-piperidin-1-yl}-ethoxy)-benzoic acid A. Preparation of 4-(6-fluoro-1H-indol-3-yl)-piperidine-1-carboxylic acid ethyl ester This compound was prepared following the procedure described in example 13 (part A) starting with 0.4 g (1.83 mmol) of 6-fluoro-3-piperidin-4-yl-1H-indole, 0.2 mL (2.13 mmol) of ethyl chloroformiate and 0.32 mL (2.13 mmol) of triethylamine. 0.32 g (60% yield) of 4-(6-fluoro-1H-indol-3-yl)-piperidine-1-carboxylic acid ethyl ester were obtained.

B. Preparation of 4-[1-(2-[1,3]dioxolan-2-yl-ethyl)-6-fluoro-1H-indol-3-yl]-piperidine-1-carboxylic acid ethyl ester This compound was prepared following the procedure described in example 13 (part B) at room temperature for 15 hours, starting with 0.1 g (0.37 mmol) of 4-(6-fluoro-1H-indol-3-yl)-piperidine-1-carboxylic acid ethyl ester and 0.081 g (0.45 mmol) of 2-(2-bromo-ethyl)-[1,3]dioxolane. 0.170 g (quantitative yield) of 4-[1-(2-[1,3]dioxolan-2-yl-ethyl)-6-fluoro-1H-indol-3-yl]-piperidine-1-carboxylic acid ethyl ester were obtained.

ESI/MS m/e=391 [(M+1)$^+$, C21 H27 F N2 O4]

C. Preparation of 1-(2-[1,3]dioxolan-2-yl-ethyl)-6-fluoro-3-piperidin-4-yl-1H-indole This compound was prepared following the procedure described in Example 13 (part C) starting with 170 g (0.448 mmol) of 4-[1-(2-[1,3]dioxolan-2-yl-ethyl)-6-fluoro-1H-indol-3-yl]-piperidine-1-carboxylic acid ethyl ester. 0.04 g (28% yield) of 1-(2-[1,3]dioxolan-2-yl-ethyl)-6-fluoro-3-piperidin-4-yl-1H-indole were obtained.

ESI/MS m/e=319 [(M+1)$^+$, C18 H23 F N2 O2]

NMR (300 MHz, CDCl$_3$) δ=1.60–1.74 (m, 2H), 1.99–2.18 (m, 5H), 2.73–2.95 (m, 3H), 3.16–3.22 (m, 2H), 3.82–4.04 (m, 4H), 4.12–4.20 (t, 2H), 4.80–4.85 (t, 1H), 6.86 (s, 1H), 6.99–7.05 (dd, 1H), 7.15–7.25 (m, 1H), 7.48–7.55 (dd, 1H).

D. Preparation of 2-(2-{4-[1-(2-[1,3]dioxolan-2-yl-ethyl)-6-fluoro-1H-indol-3-yl]-piperidin-1-yl}-ethoxy)-benzoic acid This compound was prepared following the procedure described in Example 13 (part D) starting with 0.04 g (0.11 mmol) of 1-(2-[1,3]dioxolan-2-yl-ethyl)-6-fluoro-3-piperidin-4-yl-1H-indole and 0.03 g (0.15 mmol) of of 2-(2-chloro-ethoxy)-benzoic acid methyl ester. After purification over a Varian C18 column, 0.012 g (22% yield) were obtained.

Melting point 150–151° C.

NMR (300 MHz, CDCl$_3$) δ=1.94–2.04 (m, 6H), 2.61–2.64 (m, 2H), 2.89–2.98 (m, 3H), 3.20–3.23 (d, 2H), 3.78–3.95 (m, 4H), 4.15–4.19 (t, 2H), 4.41–4.44 (m, 2H), 4.77–4.80 (t, 1H), 5.47 (bs, 1H), 6.82–6.88 (t, 1H), 6.99–7.04 (t, 1H), 7.16–7.27 (m, 3H), 7.36–7.41 (t, 1H), 7.52–7.55 (d, 1H), 7.64–7.69 (t, 1H).

EXAMPLE 25

Preparation of 3-[4-(1-thiophen-2-ylmethyl-1H-indol-3-yl)-piperidin-1-ylmethyl]-benzoic acid A. Preparation of 4-(1-thiophen-2-ylmethyl-1H-indol-3-yl)-piperidine-1-carboxylic acid ethyl ester This compound was prepared following the procedure described in example 13 (part B) at room temperature for 15 hours, starting with 4 g (15 mmol) of 4-(1H-indol-3-yl)-piperidine-1-carboxylic acid ethyl ester and 30 mL of a freshly prepared 2-bromomethyl-thiophene 0.61M solution in anhydrous ethyl ether. After standard work-up, 5.6 g (100% of yield) of the expected product was obtained.

B. Preparation of 3-piperidin-4-yl-1-thiophen-2-ylmethyl-1H-indole

This compound was prepared following the procedure described in example 13 (part C) starting with 5.6 g (15 mmol) of 4-(1-thiophen-2-ylmethyl-1H-indol-3-yl)-piperidine-1-carboxylic acid ethyl ester. After standard work-up 4.35 g (98% of yield) of the expected product were obtained.

C. Preparation of 3-[4-(1-thiophen-2-ylmethyl-1H-indol-3-yl)-piperidin-1-ylmethyl]-benzoic acid This compound was prepared following the procedure described in example 13 (part D), starting with 4.35 mmol (15 mmol) of 3-piperidin-4-yl-1-thiophen-2-ylmethyl-1H-indole and 4.58 g (20 mmol) of 3-bromomethyl-benzoic acid methyl ester. After the standard work-up, 3.3 g of the corresponding acid was obtained. The crude mixture was purified by flash chromatography over silica gel affording 0.64 g (10% of yield) of the pure acid.

Melting point 228–229° C.

NMR (300 MHz, DMSO) δ=1.55–1.79 (m, 2H), 1.87–1.97 (m, 2H), 2.10–2.22 (t, 2H), 2.73–2.81 (t, 1H), 2.90–2.94 (m, 2H), 3.59 (s, 2H), 5.52 (s, 2H), 6.92–7.01 (m, 2H), 7.07–7.13 (m, 2H), 7.24 (s, 1H), 7.36–7.57 (m, 5H), 7.83–7.86 (d, 1H), 7.92–7.94 (m, 1H).

EXAMPLE 26

Preparation of 3-[4-(1-pyridin-3-ylmethyl-1H-indol-3-yl)-piperidin-1-ylmethyl]-benzoic acid A. Preparation of 4-(1-pyridin-3-ylmethyl-1H-indol-3-yl)-piperidine-1-carboxylic acid ethyl ester This compound was prepared following the procedure described in example 13 (part B) at room temperature for 16 hours, starting with 11 g (40 mmol) of 4-(1H-indol-3-yl)-piperidine-1-carboxylic acid ethyl ester and 7.2 g (44 mmol) of 3-chloromethyl-pyridine hydrochloride. After standard work-up, 13 g of a crude oil was obtained. This crude was precipitated with ethyl ether affording 10.8 g (90% of yield) of a white solid.

B. Preparation of 3-piperidin-4-yl-1-pyridin-3-ylmethyl-1H-indole

This compound was prepared following the procedure described in example 13 (part C) starting with 10.8 g (30 mmol) of 4-(1-pyridin-3-ylmethyl-1H-indol-3-yl)-piperidine-1-carboxylic acid ethyl ester. After standard work-up 9.3 g of a crude oil were obtained. The corresponding fumarate derivative was prepared in ethanol affording 9.8 g of a white solid. After treatment with aqueous NaOH and extraction with ethyl acetate, 5.3 g (62% of yield) of pure 3-piperidin-4-yl-1-pyridin-3-ylmethyl-1H-indole were obtained.

C. 3-[4-(1-pyridin-3-ylmethyl-1H-indol-3-yl)-piperidin-1-ylmethyl]-benzoic acid

A solution containing 1.2 g (52 mmol) of 3-bromomethyl-benzoic acid methyl ester in 10 mL of anhydrous dichloromethane was added dropwise over a solution of 1.5 g (5 mmol) 3-piperidin-4-yl-1-pyridin-3-ylmethyl-1H-indole and 0.8 mL (55 mmol) of triethylamine in 35 of anhydrous dichloromethane. After stirring at room temperature for 5 hours, the crude mixture was washed with water, saturated solution of sodium hydrogencarbonate and water. The organic phase was dried and the solvent was removed under reduced pressure. The crude mixture was purified by flash chromatography over silica gel affording 0.95 g (43% of yield) of 3-[4-(1-pyridin-3-ylmethyl-1H-indol-3-yl)-piperidin-1-ylmethyl]-benzoic acid methyl ester. This ester was dissolved in 15 mL of methanol and hydrolised with NaOH 1N at room temperature for 12 hours. The crude mixture was neutralised with HCl 1N and then the solvent was removed under reduced pressure. The solid residue was washed with water and dichloromethane and the corresponding acid (0.6 g, 77% of yield) was isolated by filtration.

Melting point 190–192° C.

NMR (300 MHz, DMSO) δ=1.92–2.21 (m, 4H), 2.98–3.20 (m, 2H), 3.32–3.43 (m, 3H), 4.38 (s, 2H), 5.42 (s, 2H), 6.98–7.03 (t, 1H), 7.08–7.14 (t, 1H), 7.29–7.37 (m, 2H), 7.46–7.49 (d, 1H), 7.56–7.64 (m, 2H), 7.68–7.72 (d, 1H), 7.94–7.97 (d, 1H), 8.00–8.03 (d, 1H), 8.20 (s, 1H), 8.43–8.47 (d, 1H), 8.50 (s, 1H).

EXAMPLE 27

Preparation of 3-{4-[1-(5-chloro-thiophen-2-ylmethyl)-1H-indol-3-yl]-piperidin-1-ylmethyl}-benzoic acid This compound was prepared following the procedure described in example 19 (part C) starting with 1.48 mmol (4.48 mmol) of 1-(5-chloro-thiophen-2-ylmethyl)-3-piperidin-4-yl-1H-indole and 1.0 g (8.8 mmol) of 3-bromomethyl-benzoic acid methyl ester. The crude mixture was purified by flash chromatography over silica gel affording 0.29 g (14% of yield) of the pure acid.

Melting point 232–234° C.

NMR (300 MHz, DMSO) δ=1.91–2.09 (m, 4H), 2.88–3.20 (m, 2H), 3.22–3.36 (m, 3H), 4.34 (m, 2H), 5.48 (s, 2H), 6.93–7.03 (m, 3H), 7.09–7.12 (m, 1H), 7.25 (s, 1H), 7.50–7.66 (m, 3H), 7.84–7.86 (m, 1H), 7.99–8.01 (d, 1H), 8.15 (s, 1H).

EXAMPLE 28

Preparation of 3-{4-[1-(2-[1,3]dioxolan-2-yl-ethyl)-1H-indol-3-yl]-piperidin-1-ylmethyl}-benzoic acid A. Preparation of 3-[4-(1H-indol-3-yl)-piperidin-1-ylmethyl]-benzoic acid methyl ester This compound was prepared following the procedure described in example 1 (part D) starting with 0.2 g (1 mmol) of 3-piperidin-4-yl-1H-indole and 0.29 g (1.3 mmol) of 3-bromomethyl-benzoic acid methyl ester. After ionic exchange purification, 0.276 g (79% of yield) of 3-[4-(1H-indol-3-yl)-piperidin-1-ylmethyl]-benzoic acid methyl ester were obtained.

B. Preparation of 3-{4-[1-(2-[1,3]dioxolan-2-yl-ethyl)-1H-indol-3-yl]-piperidin-1-ylmethyl}-benzoic acid This compound was prepared following the procedure described in example 1 (part E) starting with 0.046 g (0.13 mmol) of 3-[4-(1H-indol-3-yl)-piperidin-1-ylmethyl]-benzoic acid methyl ester and 0.019 mL (0.16 mmol) of 2-(2-bromo-ethyl)-[1,3]dioxolane. After the described purification, 0.023 g (40% of yield) of the expected acid was obtained.

NMR (300 MHz, DMSO) δ=1.64–1.75 (m, 2H), 1.90–1.95 (m, 2H), 1.99–2.06 (m, 2H), 2.12–2.19 (m, 2H), 2.72–2.80 (m, 1H), 2.90–2.94 (m, 2H), 3.59 (s, 2H), 3.72–3.80 (m, 2H), 3.87–3.93 (m, 2H), 4.11–4.21 (t, 2H), 4.75–4.78 (t, 2H), 6.99–7.00 (t, 1H), 7.08–7.14 (m, 2H), 7.35–7.46 (m, 2H), 7.54–7.56 (m, 2H), 7.83–7.85 (m, 2H), 7.93 (s, 2H).

EXAMPLES 29–33

These compounds were prepared following the procedure described in example 28. The ESI/MS data, yields and purity are summarised in table 5.

TABLE 5

Examples 29–33

| Example | ESI/MS m/e [(M + 1)⁺] | Yield % (mg obtained) | Purity % |
|---|---|---|---|
| 29 | 449 | 30 (18 mg) | 92 |
| 30 | 426 | 21 (12 mg) | 94 |
| 31 | 513 | 4 (3 mg) | 78 |
| 32 | 421 | 65 (50 mg) | 67 |
| 33 | 426 | 73 (50 mg) | 65 |

EXAMPLE 34

Preparation of 2-methoxy-5-[4-(1-pyridin-3-ylmethyl-1H-indol-3-yl)-piperidin-1-ylmethyl]-benzoic acid A. Preparation of 5-[4-(1H-indol-3-yl)-piperidin-1-ylmethyl]-2-methoxy-benzoic acid ethyl ester This compound was prepared following the procedure described in example 1 (part D) starting with 0.2 g (1 mmol) of 3-piperidin-4-yl-1H-indole and 0.34 g (1.3 mmol) 5-bromomethyl-2-methoxy-benzoic acid ethyl ester. After ionic exchange purification, 0.273 g (70% of yield) of 5-[4-(1H-indol-3-yl)-piperidin-1-ylmethyl]-2-methoxy-benzoic acid ethyl ester were obtained.

B. Preparation of 2-methoxy-5-[4-(1-pyridin-3-ylmethyl-1H-indol-3-yl)-piperidin-1-ylmethyl]-benzoic acid This compound was prepared following the procedure described in example 1 (part E) starting with 0.054 g (0.13 mmol) of 5-[4-(1H-indol-3-yl)-piperidin-1-ylmethyl]-2-methoxy-benzoic acid methyl ester and 0.029 mg (0.16 mmol) of 3-chloromethyl-pyridine hydrochloride. After the described purification, 0.007 g (11% of yield) of the expected acid was obtained.

NMR (300 MHz, DMSO) δ=1.61–1.72 (m, 2H), 1.87–1.95 (m, 2H), 2.04–2.11 (m, 2H), 2.70–2.78 (m, 1H), 2.88–2.92 (d, 2H), 3-71 (s, 3H), 5.39 (s, 2H), 6.86–6.89 (d, 1H), 6.96–7.33 (m, 6H), 7.43–7.46 (d, 1H), 7.55–7.58 (d, 1H), 8.43–8.45 (d, 1H), 8.51 (s, 1H).

EXAMPLES 35–39

These compounds were prepared following the procedure described in example 34. The ESI/MS data yields and purity are summarised in table 6.

TABLE 6

Example 35–38

| Example | ESI/MS m/e [(M + 1)⁺] | Yield % (mg obtained) | Purity % |
|---|---|---|---|
| 35 | 465 | 13 (7 mg) | 90 |
| 36 | 479 | 12 (7 mg) | 87 |
| 37 | 461 | 6 (4 mg) | 84 |
| 38 | 456 | 46 (24 mg) | 53 |

EXAMPLE 39

Preparation of 4-bromo-3-[4-(1-[1,3]dioxolan-2-ylmethyl-1H-indol-3-yl)-piperidin-1-ylmethyl]-benzoic acid A. Preparation of 4-bromo-3-[4-(1H-indol-3-yl)-piperidin-1-ylmethyl]-benzoic acid methyl ester This compound was prepared following the procedure described in example 1 (part D) starting with 0.2 g (1 mmol) of 3-piperidin-4-yl-1H-indole and 0.39 g (1.3 mmol) 4-bromo-3-bromomethyl-benzoic acid methyl ester. After ionic exchange purification, 0.196 g (46% of yield) of 4-bromo-3-[4-(1H-indol-3-yl)-piperidin-1-ylmethyl]-benzoic acid methyl ester were obtained.

B. Preparation of 4-bromo-3-[4-(1-[1,3]dioxolan-2-ylmethyl-1H-indol-3-yl)-piperidin-1-ylmethyl]-benzoic acid This compound was prepared following the procedure described in example 1 (part E) starting with 0.055 g (0.13 mmol) 4-bromo-3-[4-(1H-indol-3-yl)-piperidin-1-ylmethyl]-benzoic acid methyl ester and 0.034 mg (0.16 mmol) 2-bromomethyl-[1,3]dioxolane. After the described purification, 0.021 g (32% of yield) of the expected acid was obtained.

NMR (300 MHz, DMSO) δ=1.62–1.74 (m, 2H), 1.90–1.95 (m, 2H), 2.19–2.23 (m, 2H), 2.74–2.82 (m, 1H), 2.93–3.00 (m, 2H), 3.58 (s, 2H), 4.23–4.25 (m, 2H), 5.08–5.12 (t, 1H), 6.95–7.00 (t, 1H), 7.07–7.15 (m, 2H), 7.41–7.69 (m, 4H), 7.98–8.00 (m, 1H).

EXAMPLES 40–45

These compounds were prepared following the procedure described in example 39. The ESI/MS data, yields and purity are summarised in table 7.

TABLE 7

Examples 40–45

| Example | ESI/MS m/e [(M + 1)⁺] | Yield % (mg obtained) | Purity % |
|---|---|---|---|
| 40 | 505 | 54 (46 mg) | 99 |
| 41 | 514 | 46 (19 mg) | 96 |
| 42 | 528 | 52 (22 mg) | 97 |
| 43 | 510 | 72 (29 mg) | 95 |
| 44 | 475 | 35 (14 mg) | 66 |
| 45 | 592 | 65 (30 mg) | 93 |

EXAMPLE 46

Preparation of 2-fluoro-5-[4-(1-pyridin-3-ylmethyl-1H-indol-3-yl)-piperidin-1-ylmethyl]-benzoic acid A. Preparation of 2-fluoro-5-[4-(1H-indol-3-yl)-piperidin-1-ylmethyl]-benzoic acid ethyl ester This compound was prepared following the procedure described in example 1 (part D) starting with 0.2 g (1 mmol) of 3-piperidin-4-yl-1H-indole and 0.33 g (1.3 mmol 5-bromomethyl-2-fluoro-benzoic acid ethyl ester. After ionic exchange purfication, 0.30 g (79% of yield) of 2-fluoro-5-[4-(1H-indol-3-yl)-piperidin-1-ylmethyl]-benzoic acid ethyl ester were obtained.

B. Preparation of 2-fluoro-5-[4-(1-pyridin-3-ylmethyl-1H-indol-3-yl)-piperidin-1-ylmethyl]-benzoic acid This compound was prepared following the procedure described in example 1 (part E) starting with 0.063 g (0.17 mmol) of 2-fluoro-5-[4-(1H-indol-3-yl)-piperidin-1-ylmethyl]-benzoic acid ethyl ester and 0.035 mg (0.21 mmol) of 3-chloromethyl-pyridine hydrochloride. After the described purification, 0.053 g (71% of yield) of the expected acid was obtained.

NMR (300 MHz, DMSO) δ=1.67–1.77 (m, 2H), 1.90–1.95 (m, 2H), 2.09–2.17 (t, 2H), 2.73–2.81 (m, 1H), 2.88–2.93 (d, 2H), 3.49 (s, 2H), 5.38 (s, 2H), 6.95–7.10 (m, 3H), 7.24–7.35 (m, 2H), 7.43–7.46 (d, 1H), 7.54–7.61 (m, 4H), 8.42–8.45 (dd, 1H), 8.50–8.52 (m, 1H).

EXAMPLES 47–52

These compounds were prepared following the procedure described in example 46. The ESI/MS data, yields and purity are summarised in table 8.

TABLE 8

Examples 47–52

| Example | ESI/MS m/e [(M + 1)+] | Yield % (mg obtained) | Purity % |
|---|---|---|---|
| 47 | 453 | 21 (12 mg) | 57 |
| 48 | 467 | 19 (12 mg) | 65 |
| 49 | 444 | 51 (30 mg) | 69 |
| 50 | 531 | 15 (10 mg) | 72 |
| 51 | 439 | 42 (22 mg) | 74 |
| 52 | 444 | 74 (58 mg) | 60 |

EXAMPLE 53

Preparation of 2-(2-{4-[1-(tetrahydro-furan-3-ylmethyl)-1H-indol-3-yl]-piperidin-1-yl}-ethoxy)-benzoic acid This compound was prepared following the procedure described in example 1 (part E) starting with 0.1 g (0.26 mmol) of 2-{2-[4-(1H-indol-3-yl)-piperidin-1-yl]-ethoxy}-benzoic acid methyl ester and 0.067 g (0.37 mmol) of freshly prepared tetrahydro-furan-3-ylmethyl methanesulfonate. After standard purification, 0.045 g (39% of yield) of the expected acid were obtained.

NMR (300 MHz, DMSO) δ=1.82–1.98 (m, 4H), 2.44–2.56 (m, 5H), 2.67–2.78 (m, 1H), 2.81–2.93 (m, 2H), 3.15–3.20 (m, 2H), 3.57–3.66 (m, 2H), 3.78–3.86 (m, 2H), 4.08–4.11 (m, 2H), 4.29–4.33 (m, 2H), 6.89–7.02 (m, 2H), 7.09–7.18 (m, 3H), 7.27–7.49 (m, 3H), 7.62–7.64 (d, 1H).

EXAMPLES 54–57

These compounds were prepared following the procedure described in example 53 starting with the suitable methansulfonate or halide. The ESI/MS data, yields and purity are summarised in table 9.

TABLE 9

Examples 54–57

| Example | ESI/MS m/e [(M + 1)+] | Yield % (mg obtained) | Purity % |
|---|---|---|---|
| 54 | 478 | 10 (8 mg) | 82 |
| 55 | 449 | 50 (58 mg) | 80 |
| 56 | 445 | 23 (26 mg) | 82 |
| 57 | 470 | 11 (14 mg) | 64 |

EXAMPLE 58

Preparation of 3-{4-[1-(tetrahydro-furan-3-ylmethyl)-1H-indol-3-yl]-piperidin-1-ylmethyl}-benzoic acid This compound was prepared following the procedure described in example 1 (part E) starting with 0.1 g (0.28 mmol) of 3-[4-(1H-indol-3-yl)-piperidin-1-ylmethyl]-benzoic acid methyl ester (example 28, part A) and 0.72 g (0.4 mmol) of (tetrahydro-furan-3-yl)-methansulfonate. After standard purification, 0.04 g (34% of yield) of the expected acid were obtained.

NMR (300 MHz, DMSO) δ=1.53–1.94 (m, 5H), 2.07–2.14 (t, 2H), 2.61–2.79 (m, 2H), 2.89–2.94 (m, 3H), 3.40–3.71 (m, 4H), 3.77–3.85 (m, 2H), 4.05–4.09 (d, 2H), 6.95–7.00 (t, 1H), 7.07–7.13 (m, 1H), 7.25–7.34 (m, 3H), 7.42–7.45 (d, 1H), 7.53–7.56 (d, 1H), 7.74–7.77 (d, 1H), 7.83–7.87 (m, 1H).

EXAMPLES 59–51

These compounds were prepared following the procedure described in example 58 starting with the suitable methansulfonate or halide. The ESI/MS data, yields and purity are summarised in table 10.

TABLE 10

Examples 59–61

| Example | ESI/MS m/e [(M + 1)+] | Yield % (mg obtained) | Purity % |
|---|---|---|---|
| 59 | 419 | 39 (46 mg) | 85 |
| 60 | 445 | 17 (24 mg) | 81 |
| 61 | 415 | 10 (9 mg) | 63 |

EXAMPLE 62

Preparation of 2-[4-(1-pyridin-3-ylmethyl-1H-indol-3-yl)-piperidin-1-ylmethyl]-nicotinic acid A. Preparation of 2-[4-(1H-indol-3-yl)-piperidin-1-ylmethyl]-nicotinic acid ethyl ester This compound was prepared following the procedure described in example 1 (part D) starting with 0.5 g (2.5 mmol) of 3-piperidin-4-yl-1H-indole and 0.65 g (3.25 mmol) of 2-bromomethyl-nicotinic acid ethyl ester. After the standard purification, 0.84 g (92% of yield) of 2-[4-(1H-indol-3-yl)-piperidin-1-ylmethyl]-nicotinic acid ethyl ester were obtained.

B. Preparation of 2-[4-(1-pyridin-3-ylmethyl-1H-indol-3-yl)-piperidin-1-ylmethyl]-nicotinic acid This compound was prepared following the procedure described in example 1 (part E) starting with 0.76 g (0.21 mmol) of 2-[4-(1H-indol-3-yl)-piperidin-1-ylmethyl]-nicotinic acid ethyl ester and 0.04 g (0.25 mmol) of 3-chloromethyl-pyridine hydrochloride. After standard purification, 0.040 g (45% of yield) of the expected acid were obtained.

NMR (300 MHz, DMSO) δ=1.65–1.79 (m, 2H), 1.99–2.10 (m, 2H), 2.55–2.76 (m, 2H), 2.89–2.96 (t, 1H), 3.08–3.12 (d, 2H), 4.24 (s, 2H), 5.40 (s, 2H), 6.98–7.12 (dt,

2H), 7.29–7.39 (m, 3H), 7.44–7.47 (d, 1H), 7.55–7.61 (m, 2H), 8.06–8.08 (d, 1H), 8.43–8.45 (m, 1H), 8.49–8.51 (m, 1H).

EXAMPLES 63–64

These compounds were prepared following the procedure described in example 62 starting with the suitable methansulfonate or halide. The ESI/MS data, yields and purity are summarised in table 11.

TABLE 11

Examples 63–64

| Example | ESI/MS m/e [(M + 1)$^+$] | Yield % (mg obtained) | Purity % |
|---|---|---|---|
| 63 | 449 | 54 (50 mg) | 51 |
| 64 | 432 | 21 (19 mg) | 87 |

EXAMPLE 65

Preparation of 3-{4-[1-(5-chloro-thiophen-2-ylmethyl)-6-fluoro-1H-indol-3-yl]-piperidin-1-ylmethyl}-benzoic acid A. Preparation of 3-[4-(6-fluoro-1H-indol-3-yl)-piperidin-1-ylmethyl]-benzoic acid methyl ester This compound was prepared following the procedure described in example 1 (part D) starting with 0.5 g (2.3 mmol) of 6-fluoro-3-piperidin-4-yl-1H-indole and 0.7 g (3 mmol) of 3-bromomethyl-benzoic acid. After the standard purification, 0.842 g (93% of yield) of 3-[4-(6-fluoro-1H-indol-3-yl)-piperidin-1-ylmethyl]-benzoic acid methyl ester were obtained.

B. Preparation of 3-{4-[1-(5-chloro-thiophen-2-ylmethyl)-6-fluoro-1H-indol-3-yl]-piperidin-1-ylmethyl}-benzoic acid This compound was prepared following the procedure described in example 1 (part E) starting with 0.07 g (0.19 mmol) of 3-[4-(6-fluoro-1H-indol-3-yl)-piperidin-1-ylmethyl]-benzoic acid methyl ester and 0.05 g (0.29 mmol) of 2-chloro-5-chloromethyl-thiophene. After standard purification, 0.01 g (10% of the yield) of the expected acid were obtained.

NMR (300 MHz, DMSO) δ=2.14–2.29 (m, 4H), 2.76–2.85 (m, 2H), 2.94–3.01 (m, 1H), 3.47–3.54 (m, 2H), 4.17 (s, 2H), 5.25 (s, 2H), 6.71–6.79 (m, 2H), 6.83–6.90 (dt, 1H), 6.97–7.03 (m, 2H), 7.48–7.56 (m, 2H), 7.75–7.78 (d, 1H), 8.09–8.12 (m, 2H), 8.15–8.19 (m, 1H).

EXAMPLES 66–67

Compounds 66 and 67 were prepared following the procedure described in example 65 starting with the suitable methansulfonate or halide. The ESI/MS data, yields and purity are summarised in table 11.

TABLE 11

Examples 66–67

| Example | ESI/MS m/e [(M + 1)$^+$] | Yield % (mg obtained) | Purity % |
|---|---|---|---|
| 66 | 463 | 17 (15 mg) | 67 |
| 67 | 463 | 15 (13 mg) | 76 |

EXAMPLE 68

Preparation of 2-methoxy-5-{4-[1-(2-thiophen-2-yl-ethyl)-1H-indol-3-yl]-piperidin-1-ylmethyl}-benzoic acid A. Preparation of 5-[4-(1H-indol-3-yl)-piperidin-1-ylmethyl]-2-methoxy-benzoic acid ethyl ester This compound was prepared following the procedure described in example 1 (part D) starting with 0.5 g (2.5 mmol) of 6-fluoro-3-piperidin-4-yl-1H-indole and 0.88 g (3.2 mmol) of 5-bromomethyl-2-methoxy-benzoic acid ethyl ester. After standard purification, 0.83 g (91% of yield) of 5-[4-(1H-indol-3-yl)-piperidin-1-ylmethyl]-2-methoxy-benzoic acid ethyl ester were obtained.

B. Preparation of 2-methoxy-5-{4-[1-(2-thiophen-2-yl-ethyl)-1H-indol-3-yl]-piperidin-1-ylmethyl}-benzoic acid This compound was prepared following the procedure described in example 1 (part E) starting with 0.07 g (0.18 mmol) of 5-[4-(1H-indol-3-yl)-piperidin-1-ylmethyl]-2-methoxy-benzoic acid ethyl ester and 0.05 g (0.25 mmol) of 2-thiophen-2-yl-ethyl methansulfonate. After the standard purification, 0.009 g (10% of yield) of the expected acid was obtained.

EXAMPLES 69 AND 70

A. Preparation of 5-[4-(6-fluoro-1H-indol-3-yl)-piperidin-1-ylmethyl]-2-methoxy-benzoic acid ethyl ester This compound was prepared following the procedure described in example 1 (part D) starting with 0.5 g (2.2 mmol) of 6-fluoro-3-piperidin-4-yl-1H-indole and 0.8 g (2.9 mmol) of 5-bromomethyl-2-methoxy-benzoic acid ethyl ester. After standard purification, 0.91 g (100% of yield) of 5-[4-(6-fluoro-1H-indol-3-yl)-piperidin-1-ylmethyl]-2-methoxy-benzoic acid ethyl ester were obtained.

B. Preparation of 5-{4-[6-fluoro-1-(2-thiophen-2-yl-ethyl)-1H-indol-3-yl]-piperidin-1-ylmethyl}-2-methoxy-benzoic acid and 5-{4-[6-fluoro-1-(2-morpholin-4-yl-ethyl)-1H-indol-3-yl]-piperidin-1-ylmethyl}-2-methoxy-benzoic acid These compounds were prepared following the procedure described in example 1 (part E) starting with 0.07 g (0.17 mmol) of 5-[4-(6-fluoro-1H-indol-3-yl)-piperidin-1-ylmethyl]-2-methoxy-benzoic acid ethyl ester.

| Example | ESI/MS m/e [(M + 1)$^+$] | Yield % (mg obtained) | Purity % |
|---|---|---|---|
| 69 | 493 | 17 (13 mg) | 91 |
| 70 | 496 | 14 (12 mg) | 75 |

EXAMPLE 71

Preparation of 5-{4-[1-(2-[1,4]dioxan-2-yl-ethyl)-1H-indol-3-yl]-piperidin-1-ylmethyl}-2-methoxy-benzoic acid A. Preparation of 4-[1-(2-[1,4]dioxan-2-yl-ethyl)-1H-indol-3-yl]-piperidine-1-carboxylic acid ethyl ester This compound was prepared following the procedure described in example 13 (part B) starting with 0.47 g (1.2 mmol) of 4-(1H-indol-3-yl)-piperidine-1-carboxylic acid ethyl ester and 0.62 g (2.9 mmol) of 2-[1,4]dioxan-2-ylethyl methansulfonate. The reaction mixture was stirred at 40° C. for 24 hours. After standard work-up and purification, 0.47 g (51% of yield) of 4-[1-(2-[1,4]dioxan-2-yl-ethyl)-1H-indol-3-yl]-piperidine-1-carboxylic acid ethyl ester were obtained.

B. Preparation of 1-(2-[1,4]dioxan-2-yl-ethyl)-3-piperidin-4-yl-1H-indole

This compound was prepared following the procedure described in example 13 (part C) starting with 0.47 g (1.2 mmol) of 4-[1-(2-[1,4]dioxan-2-yl-ethyl)-1H-indol-3-yl]-piperidine-1-carboxylic acid ethyl ester. After standard work-up, 0.2 g (53% of yield) of 1-(2-[1,4]dioxan-2-yl-ethyl)-3-piperidin-4-yl-1H-indole were obtained.

C. Preparation of 5-{4-[1-(2-[1,4]dioxan-2-yl-ethyl)-1H-indol-3-yl]-piperidin-1-ylmethyl}-2-methoxy-benzoic acid This compound was prepared following the procedure described in example 13 (part D) starting with 0.06 g (0.19 mmol) of 1-(2-[1,4]dioxan-2-yl-ethyl)-3-piperidin-4-yl-1H-indole and 0.071 g (0.26 mmol) of 5-bromomethyl-2-methoxy-benzoic acid ethyl ester. After standard purification, 0.019 g (65% of yield) were obtained.

NMR (300 MHz, CDCl$_3$) δ=1.73–1.80 (m, 2H), 2.15–2.30 (m, 4H), 2.55–2.80 (m, 2H), 2.99–3.10 (m, 1H), 3.20–3.45 (m, 3H), 3.52–3.67 (m, 3H), 3.52–3.67 (m, 5H), 3.78–3.82 (m, 1H), 3.98 (s, 3H), 4.03–4.10 (m, 2H), 4.18–4.23 (t, 2H), 6.91 (s, 1H), 6.99–7.10 (m, 2H), 7.17–7.22 (t, 1H), 7.30–7.35 (m, 1H), 7.56–7.58 (m, 3H), 8.03–8.08 (m, 1H).

EXAMPLE 72

Preparation of 3-{4-[1-(2-[1,4]dioxan-2-yl-ethyl)-1H-indol-3-yl]-piperidin-1-ylmethyl}-benzoic acid This compound was prepared following the procedure described in example 71 (part C) starting with 0.06 g (0.19 mmol) of 1-(2-[1,4]dioxan-2-yl-ethyl)-3-piperidin-4-yl-1H-indole and 0.060 g (0.26 mmol) of 3-bromomethyl-benzoic acid methyl ester. After standard purification, 0.037 g (75% of yield) were obtained.

NMR (300 MHz, CDCl$_3$) δ=1.65–1.80 (m, 2H), 2.10–2.24 (m, 2H), 2.35–2.52 (m, 2H), 2.81–3.09 (m, 3H), 3.18–3.33 (m, 3H), 3.51–3.66 (m, 5H), 3.77–3.80 (m, 1H), 4.15–4.27 (m, 4H), 6.93 (s, 1H), 7.02–7.07 (t, 1H), 7.15–7.20 (t, 1H), 7.25–7.33 (m, 1H), 7.40–7.56 (m, 2H), 7.62–7.85 (m, 1H), 8.08–8.10 (d, 1H), 8.34 (s, 1H).

EXAMPLE 73

Preparation of 2-methoxy-5-[4-(1-thiophen-2-ylmethyl-1H-indol-3-yl)-piperidin-1-ylmethyl]-benzoic acid This compound was prepared following the procedure described in example 25 (part C) starting with 1.90 g (0.065 mol) of 3-piperidin-4-yl-1-thiophen-2-ylmethyl-1H-indole and 1.92 (0.071 mol) of 5-bromomethyl-2-methoxy-benzoic acid ethyl ester. After standard purification and recrystallization with ethanol, 1.2 g (40% of yield) of the expected acid.

Melting point 242–243° C.

NMR (300 MHz, DMSO) δ=1.6–1.73 (m, 2H), 1.91–1.95 (d, 2H), 2.09–2.17 (t, 2H), 2.32–2.82 (m, 1H), 2.88–2.92 (d, 2H), 3.49 (s, 2H), 3.80 (s, 3H), 5.52 (s, 2H), 6.92–6.96 (m, 1H), 6.93–7.00 (m, 1H), 7.06–7.12 (m, 3H), 7.23 (s, 1H), 7.36–7.38 (dd, 1H), 7.42–7.46 (dd, 1H), 7.46–7.48 (m, 1H), 7.49–7.51 (m, 1H), 7.53–7.55 (m, 1H), 7.56–7.59 (m, 2H).

EXAMPLE 74

Preparation of 4-bromo-3-[4-(1-pyridin-4-ylmethyl-1H-indol-3-yl)-piperidin-1-ylmethyl]-benzoic acid A. Preparation of 4-(1-pyridin-4-ylmethyl-1H-indol-3-yl)-piperidine-1-carboxylic acid ethyl ester This compound was prepared following the procedure described in example 13 (part B) at room temperature for 15 hours, starting with 11 g (40 mmol) of 4-(1H-indol-3-yl)-piperidine-1-carboxylic acid ethyl ester and 8 g (48 mmol) of 4-chloromethyl-pyridine hydrochloride, stirring at room temperature for 18 hours. After standard work-up, 11.8 g (81% of the yield) of 4-(1-pyridin-4-ylmethyl-1H-indol-3-yl)-piperidine-1-carboxylic acid ethyl ester were obtained.

B. Preparation of 3-piperidin-4-yl-1-pyridin-4-ylmethyl-1H-indole

This compound was prepared following the procedure described in example 13 (part C) starting with 11.8 (0.032 mol) of 4-(1-pyridin-4-ylmethyl-1H-indol-3-yl)-piperidine-1-carboxylic acid ethyl ester. After purification through the fumarate derivative as described in example 26 (part B), 6 g (64% of yield) of 3-piperidin-4-yl-1-pyridin-4-ylmethyl-1H-indole were obtained.

C. Preparation of 4-bromo-3-[4-(1-pyridin-4-ylmethyl-1H-indol-3-yl)-piperidin-1-ylmethyl]-benzoic acid This compound was prepared following the procedure described in example 13 (part D) starting with 1.5 g (50 mmol) of 3-piperidin-4-yl-1-pyridin-4-ylmethyl-1H-indole and 1.7 g (55 mmol) of 4-bromo-3-bromomethyl-benzoic acid methyl ester. After standard work-up and recrystallisation with ethyl ether, 1.7 g (68% of yield) of the expected acid were obtained.

Melting point 167–168° C.

NMR (300 MHz, DMSO) δ=1.66–1.77 (m, 2H), 1.91–2.02 (m, 2H), 2.25–2.33 (t, 2H), 2.80–2.97 (m, 3H), 3.65 (s, 2H), 5.42 (s, 2H), 6.98–7.10 (m, 4H), 7.31–7.33 (m, 2H), 7.59–7.62 (d, 1H), 7.68–7.81 (m, 2H), 8.09 (s, 1H), 8.45–8.48 (m, 2H).

EXAMPLE 75

Preparation of 2-methoxy-5-{4-[1-(2-thiophen-3-yl-ethyl)-1H-indol-3-yl]-piperidin-1-ylmethyl}-benzoic acid This compound was prepared following the procedure described in example 13 (part D) starting with 1 g (3.2 mmol) of 3-piperidin-4-yl-1-(2-thiophen-3-yl-ethyl)-1H-indole and 1.15 g (4.2 mmol) of 5-bromomethyl-2-methoxy-benzoic acid ethyl ester. After standard work-up and purification, 1.16 g (76% of yield) of the expected acid were obtained.

Melting point 219–220° C.

NMR (300 MHz, DMSO) δ=1.58–1.70 (m, 2H), 1.89–1.93 (d, 2H), 2.11–2.19 (t, 2H), 2.70–2.78 (m, 2H), 2.89–2.93 (d, 1H), 3.02–3.07 (m, 2H), 3.50 (s, 2H), 3.80 (s, 3H), 4.30–4.35 (m, 2H), 6.95–7.12 (m, 5H), 7.18 (s, 1H), 7.43–7.46 (m, 3H), 7.53–7.55 (d, 1H), 7.59 (s, 1H).

EXAMPLE 76

Preparation of 3-{4-[1-(2-morpholin-4-yl-ethyl)-1H-indol-3-yl]-piperidin-1-ylmethyl}-benzoic acid A. Preparation of 4-[1-(2-morpholin-4-yl-ethyl)-1H-indol-3-yl]-piperidine-1-carboxylic acid ethyl ester This compound was prepared following the procedure described in example 13 (part B), starting with 11 g (40 mmol) of 4-(1H-indol-3-yl)-piperidine-1-carboxylic acid ethyl ester and 9 g (48 mmol) of 4-(2-chloro-ethyl)-morpholine hydrochloride. The reaction mixture was stirred at room temperature for 18 hours. After standard work-up and purification, 13.5 g (88% of yield) of 4-[1-(2-morpholin-4-yl-ethyl)-1H-indol-3-yl]-piperidine-1-carboxylic acid ethyl ester were obtained.

B. Preparation of 1-(2-morpholin-4-yl-ethyl)-3-piperidin-4-yl-1H-indole

This compound was prepared following the procedure described in example 13 (part C) starting with 13.5 g (35 mmol) of 4-[1-(2-morpholin-4-yl-ethyl)-1H-indol-3-yl]-piperidine-1-carboxylic acid ethyl ester. After standard work-up, 9.5 g (87% of yield) of 1-(2-morpholin-4-yl-ethyl)-3-piperidin-4-yl-1H-indole were obtained.

C. Preparation of 3-{4-[1-(2-morpholin-4-yl-ethyl)-1H-indol-3-yl]-piperidin-1-ylmethyl}-benzoic acid This compound was prepared following the procedure described in example 13 (part D) starting with 2.4 g (7.5 mmol) of 1-(2-morpholin-4-yl-ethyl)-3-piperidin-4-yl-1H-indole and 1.8 g (7.8 mmol) of 3-bromomethyl-benzoic acid methyl ester. After standard work-up and purification, 0.75 g (22% of yield) of the expected acid were obtained.

Melting point 186–191° C.

NMR (300 MHz, DMSO) δ=1.91–2.10 (m, 4H), 2.42–2.51 (m, 4H), 2.66–2.82 (m, 4H), 3.16–3.26 (m, 3H), 3.54–3.58 (m, 4H), 4.15–4.26 (m, 4H), 6.96–7.00 (t, 1H), 7.09–7.14 (t, 1H), 7.18 (s, 1H), 7.42–7.45 (m, 2H), 7.54–7.64 (m, 2H), 7.84–7.86 (m, 1H), 7.95–7.98 (d, 1H), 8.11 (s, 1H).

EXAMPLE 77

Preparation of 2-[2-(4-{1-[2-benzo[1,3]dioxol-5-yloxy)-ethyl]-1H-indol-3-yl}-piperidin-1-yl)-ethoxy]-benzoic acid A. Preparation of 4-{1-[2-(benzo[1,3]dioxol-5-yloxy)-ethyl]-1H-indol-3-yl}-piperidine-1-carboxylic acid ethyl ester This compound was prepared following the procedure described in example 13 (part B) starting with 11 g (40 mmol) of 4-(1H-indol-3-yl)-piperidine-1-carboxylic acid ethyl ester and 9.6 g (48 mmol) of 5-(2-chloro-ethoxy)-benzo[1,3]dioxole. The mixture was stirred at room temperature for 18 hours. After standard work-up and purification, 10.5 g (60% of yield) of 4-{1-[2-(benzo[1,3]dioxol-5-yloxy)-ethyl]-1H-indol-3-yl}-piperidine-1-carboxylic acid ethyl ester were obtained.

B. Preparation of 1-[2-(benzo[1,3]dioxol-5-yloxy)-ethyl]-3-piperidin-4-yl-1H-indole This compound was prepared following the procedure described in example 13 (part C) starting with 12.5 g (0.028 mmol) of 4-{1-[2-(benzo[1,3]dioxol-5-yloxy)-1H-indol-3-yl}-piperidine-1-carboxylic acid ethyl ester. After standard work-up, 9 g (87% of yield) of 1-[2-(benzo[1,3]dioxol-5-yloxy)-ethyl]-3-piperidin-4-yl-1H-indole were obtained.

C. Preparation of 2-[2-(4-{1-[2-(benzo[1,3]dioxol-5-yloxy)-ethyl]-1H-indol-3-yl}-piperidin-1-yl)-ethoxy]-benzoic acid This compound was prepared following the procedure described in example 13 (part D) starting with 2.3 g (6.2 mmol) of 1-[2-(benzo[1,3]dioxol-5-yloxy)-ethyl]-3-piperidin-4-yl-1H-indole and 1.5 g (7.1 mmol) of 2-(2-chloroethoxy)-benzoic acid methyl ester. After standard work-up and recrystallisation with methanol, 1.6 g (49% of yield) of the expected acid were obtained.

Melting point 123–125° C.

NMR (300 MHz, DMSO) δ=1.85–2.06 (m, 4H), 2.61–2.69 (m, 2H), 2.89–2.98 (m, 3H), 3.16–3.24 (m, 2H), 4.17–4.21 (m, 2H), 4.42–4.49 (m, 4H), 5.93 (s, 2H), 6.30–6.33 (dd, 1H), 6.56–6.57 (m, 1H), 6.76–6.78 (d, 1H), 6.97–7.04 (m, 2H), 7.11–7.16 (t, 1H), 7.20–7.24 (m, 2H), 7.36–7.41 (m, 1H), 7.48–7.55 (m, 2H), 7.64–7.66 (d, 1H).

EXAMPLE 78

Preparation of 5-{4-[6-fluoro-1-(2-thiophen-3-yl-ethyl)-1H-indol-3-yl]-piperidin-1-ylmethyl}-2-methoxy-benzoic acid A. Preparation of 4-[6-fluoro-1-(2-thiophen-3-yl-ethyl)-1H-indol-3-yl]-piperidine-1-carboxylic acid ethyl ester This compound was prepared following the procedure described in example 13 (part B) starting with 4 g (13.8 mmol) of 4-(6-fluoro-1H-indol-3-yl)-piperidine-1-carboxylic acid ethyl ester (example 24, part A) and 3.3 g (16 mmol) of 2-thiophen-3-yl-ethyl methansulfonate. The reaction mixture was stirred at 60° C. for 3 hours. After standard work-up, 5.6 g (100% of yield) of 4-[6-fluoro-1-(2-thiophen-3-yl-ethyl)-1H-indol-3-yl]-piperidine-1-carboxylic acid ethyl ester were obtained.

B. Preparation of 6-fluoro-3-piperidin-4-yl-1-(2-thiophen-3-yl-ethyl)-1H-indole

This compound was prepared following the procedure described in example 13 (part C) starting with 5.6 g (13.8 mmol) of 4-[6-fluoro-1-(2-thiophen-3-yl-ethyl)-1H-indol-3-yl]-piperidine-1-carboxylic acid ethyl ester. After standard work-up, 4.5 g (99% of yield) of 6-fluoro-3-piperidin-4-yl-1-(2-thiophen-3-yl-ethyl)-1H-indole were obtained.

C. Preparation of 5-{4-[6-fluoro-1-(2-thiophen-3-yl-ethyl)-1H-indol-3-yl]-piperidin-1-ylmethyl}-2-methoxy-benzoic acid This compound was prepared following the procedure described in example 13 (part D) starting with 2.3 g (6.9 mmol) of 6-fluoro-3-piperidin-4-yl-1-(2-thiophen-3-yl-ethyl)-1H-indole and 2 g (7.5 mmol) of 3-bromomethyl-4-methoxy-benzoic acid ethyl ester. After standard work-up and recrystallisation with methanol, 1 g (29% of yield) of the expected acid were obtained.

Melting point 228–229° C.

NMR (300 MHz, DMSO) δ=1.56–1.67 (m, 2H), 1.87–1.91 (m, 2H), 2.10–2.17 (t, 2H), 2.68–2.76 (m, 1H), 2.88–2.92 (d, 2H), 2.99–3.05 (t, 2H), 3.50 (s, 2H), 3.80 (s, 3H), 4.29–4.31 (m, 2H), 6.78–6.85 (m, 1H), 6.99–7.02 (dd, 1H), 7.07–7.10 (m, 2H), 7.16–7.19 (m, 1H), 7.28–7.32 (m, 2H), 7.38–7.49 (m, 2H), 7.51–7.54 (m, 1H), 7.58–7.59 (m, 1H).

EXAMPLE 79

Preparation of 5-{4-[1-(5-chloro-thiophen-2-ylmethyl-6-fluoro-1H-indol-3-yl]-piperidin-1-ylmethyl}-2-methoxy-benzoic acid A. Preparation of 4-[1-(5-chloro-thiophen-2-ylmethyl)-6-fluoro-1H-indol-3-yl]-piperidine-1-carboxylic acid ethyl ester This compound was prepared following the procedure described in example 13 (part B) starting with 2.2 g (7.5 mmol) of 4-(6-fluoro-1H-indol-3-yl)-piperidine-1-carboxylic acid ethyl ester (example 24, part A) and 1.1 mL (8.8 mmol) of 2-chloro-5-chloromethyl-thiophene. The reaction mixture was stirred at room temperature for 18 hours. After standard work-up, 2.2 g (68% of yield) of 4-[1-(5-chloro-thiophen-2-ylmethyl)-6-fluoro-1H-indol-3-yl]-piperidine-1-carboxylic acid ethyl ester were obtained.

B. Preparation of 1-(5-chloro-thiophen-2-ylmethyl)-6-fluoro-3-piperidin-4-yl-1H-indole This compound was prepared following the procedure described in example 13 (part C) starting with 4.4 g (10.4 mmol) 4-[1-(5-chloro-thiophen-2-ylmethyl)-6-fluoro-1H-indol-3-yl]-piperidine-1-carboxylic acid ethyl ester. After standard work-up, 2.4 g (67% of yield) of 1-(5-chloro-thiophen-2-ylmethyl)-6-fluoro-3-piperidin-4-yl-1H-indole were obtained.

C. Preparation of 5-{4-[1-(5-chloro-thiophen-2-ylmethyl)-6-fluoro-1H-indol-3-yl]-piperidin-1-ylmethyl}-2-methoxy-benzoic acid This compound was prepared following the procedure described in example 13 (part D) starting with 2.4 g (6.9 mmol) of 1-(5-chloro-thiophen-2-ylmethyl)-6-fluoro-3-piperidin-4-yl-1H-indole and 2 g (7.5 mmol) of 3-bromomethyl-4-methoxy-benzoic acid ethyl ester. After standard work-up, 0.7 g (20% of yield) of the expected acid were obtained.

Melting point 232–236° C.

NMR (300 MHz, DMSO) δ=1.65–1.73 (m, 2H), 1.90–1.94 (d, 2H), 2.15–2.22 (t, 2H), 2.70–2.78 (m, 1H), 2.91–2.95 (m, 2H), 3.53 (s, 2H), 3.80 (s, 3H), 5.45 (s, 2H), 6.83–6.89 (t, 1H), 6.95–7.08 (m, 3H), 7.23 (s, 1H), 7.40–7.44 (m, 2H), 7.54–7.59 (m, 2H).

EXAMPLE 80

Preparation of 5-[4-(6-fluoro-1-furan-3-ylmethyl-1H-indol-3-yl)-piperidin-1-ylmethyl]-2-methoxy-benzoic acid A. Preparation of 4-(6-fluoro-1-furan-3-ylmethyl-1H-indol-3-yl)-piperidine-1-carboxylic acid ethyl ester This compound was prepared following the procedure described in example 13 (part B) starting with 4 g (13.8 mmol) of 4-(6-fluoro-1H-indol-3-yl)-piperidine-1-carboxylic acid ethyl ester (example 24, part A) and 17 mL (16 mmol) of a freshly prepared solution 0.94 M in ethyl ether of 3-bromomethyl-furan. The reaction mixture was stirred at room temperature for 18 hours. After standard work-up, 5.3 g (99% of yield) of 4-(6-fluoro-1-furan-3-ylmethyl-1H-indol-3-yl)-piperidine-1-carboxylic acid ethyl ester were obtained.

B. Preparation of 6-fluoro-1-furan-3-ylmethyl-3-piperidin-4-yl-1H-indole

This compound was prepared following the procedure described in example 13 (part C) starting with 5.3 g (13.7 mmol) of 4-(6-fluoro-1-furan-3-ylmethyl-1H-indol-3-yl)-piperidine-1-carboxylic acid ethyl ester. After standard work-up, 3.5 g (86% of yield) of 6-fluoro-1-furan-3-ylmethyl-3-piperidin-4-yl-1H-indole were obtained.

C. Preparation of 5-[4-(6-fluoro-1-furan-3-ylmethyl-1H-indol-3-yl)-piperidin-1-ylmethyl]-2-methoxy-benzoic acid This compound was prepared following the procedure described in example 13 (part D) starting with 2.1 g (6.9 mmol) of 6-fluoro-1-furan-3-ylmethyl-3-piperidin-4-yl-1H-indole and 2 g (7.5 mmol) of 3-bromomethyl-4-methoxy-benzoic acid ethyl ester. After standard work-up, 0.9 g (28% of yield) of the expected acid were obtained.

Melting point 228–229° C.

NMR (300 MHz, DMSO) δ=1.56–1.73 (m, 2H), 1.76–1.89 (m, 2H), 2.11–2.18 (m, 2H), 2.62–2.82 (m, 1H), 2.90–2.93 (m, 2H), 3.51 (s, 2H), 3.81 (s, 3H), 5.11 (s, 2H), 6.40 (s, 1H), 6.76–6.92 (m, 1H), 7.07–7.10 (d, 1H), 7.22 (s, 1H), 7.36–7.43 (m, 2H), 7.46–7.59 (m, 3H), 7.72 (s, 1H).

EXAMPLE 81

Preparation of 3-{4-[1-(2-pyridin-2-yl-ethyl)-1H-indol-3-yl]-piperidin-1-ylmethyl}-benzoic acid A. Preparation of 4-[1-(2-pyridin-2-yl-ethyl)-1H-indol-3-yl]-piperidine-1-carboxylic acid ethyl ester This compound was prepared following the procedure described in example 13 (part B) starting with 11 g (40 mmol) 4-(1H-indol-3-yl)-piperidine-1-carboxylic acid ethyl and 8.6 g (48 mmol) of a freshly prepared 2-pyridin-2-yl-ethyl methansulfonate. The reaction mixture was stirred at 60° C. for 18 hours. After standard work-up, 3.2 g (21% of yield) 4-[1-(2-pyridin-2-yl-ethyl)-1H-indol-3-yl]-piperidine-1-carboxylic acid ethyl ester were obtained.

B. Preparation of 3-piperidin-4-yl-1-(2-pyridin-2-yl-ethyl)-1H-indole

This compound was prepared following the procedure described in example 13 (part C) starting with 8.8 g (12.9 mmol) of 4-[1-(2-pyridin-2-yl-ethyl)-1H-indol-3-yl]-piperidine-1-carboxylic acid ethyl ester. After standard work-up, 3.4 g (87% of yield) of 3-piperidin-4-yl-1-(2-pyridin-2-yl-ethyl)-1H-indole were obtained.

C. Preparation of 3-{4-[1-(2-pyridin-2-yl-ethyl)-1H-indol-3-yl]-piperidin-1-ylmethyl}-benzoic acid This compound was prepared following the procedure described in example 13 (part D) starting with 3.4 g (11 mmol) of 3-piperidin-4-yl-1-(2-pyridin-2-yl-ethyl)-1H-indole and 2.7 g (11.5 mmol) of 3-bromomethyl-benzoic acid methyl ester. After standard work-up and recrystallisation with dichloromethane/methanol, 1.4 g (29% of yield) of the expected acid were obtained.

Melting point 141–142° C.

NMR (300 MHz, DMSO) δ=1.55–1.72 (m, 2H), 1.86–1.90 (m, 2H), 2.11–2.19 (t, 2H), 2.69–2.74 (m, 1H), 2.88–2.92 (m, 2H), 3.15–3.20 (t, 2H), 3.59 (s, 2H), 4.45–4.50 (t, 2H), 6.94–7.24 (m, 5H), 7.37–7.67 (m, 5H), 7.83–7.86 (m, 1H), 7.94 (s, 1H), 8.51–8.54 (m, 1H).

EXAMPLE 82

Preparation of 5-[4-(6-fluoro-1-thiophen-2-ylmethyl-1H-indol-3-yl)-piperidin-1-ylmethyl]-2-methoxy-benzoic acid A. Preparation of 4-(6-fluoro-1-thiophen-2-ylmethyl-1H-indol-3-yl)-piperidine-1-carboxylic acid ethyl ester This compound was prepared following the procedure described in example 13 (part B) starting with 4 g (13.8 mmol) of 4-(6-fluoro-1H-indol-3-yl)-piperidine-1-carboxylic acid ethyl ester (example 24, part A) and 16 mL of (16 mmol) of a freshly prepared 1M solution in ethyl ether of 2-bromomethyl-thiophene. The reaction mixture was stirred at room temperature for 18 hours. After standard work-up, 5.42 g (100% of yield) of 4-(6-fluoro-1-thiophen-2-ylmethyl-1H-indol-3-yl)-piperidine-1-carboxylic acid ethyl ester were obtained.

B. Preparation of 6-fluoro-3-piperidin-4-yl-1-thiophen-2-ylmethyl-1H-indole

This compound was prepared following the procedure described in example 13 (part C) starting with 9.4 g (13.8 mmol) of 4-(6-fluoro-1-thiophen-2-ylmethyl-1H-indol-3-yl)-piperidine-1-carboxylic acid ethyl ester. After standard work-up, 2.9 g (69% of yield) of 6-fluoro-3-piperidin-4-yl-1-thiophen-2-ylmethyl-1H-indole were obtained.

C. 5-[4-(6-fluoro-1-thiophen-2-ylmethyl-1H-indol-3-yl)-piperidin-1-ylmethyl]-2-methoxy-benzoic acid This compound was prepared following the procedure described in example 13 (part D) starting with 2.9 g (9.2 mmol) of 6-fluoro-3-piperidin-4-yl-1-thiophen-2-ylmethyl-1H-indole and 2.7 g (11.5 mmol) of 5-bromomethyl-2-methoxy-benzoic acid ethyl ester. After standard work-up, 1.2 g (27% of yield) of the expected acid were obtained.

Melting point 245–246° C.

NMR (300 MHz, DMSO) δ=1.60–1.68 (m, 2H), 1.89–1.93 (m, 2H), 2.10–2.18 (t, 2H), 2.65–2.80 (m, 1H), 2.89–2.93 (d, 2H), 3.50 (s, 2H), 3.80 (s, 3H), 5.50 (s, 2H), 6.81–6.87 (m, 1H), 6.94–6.96 (m, 1H), 7.09–7.13 (m, 2H), 7.23 (s, 1H), 7.36–7.44 (m, 3H), 7.52–7.58 (m, 2H).

EXAMPLE 83

Preparation of 3-[4-(1-furan-2-ylmethyl-1H-indol-3-yl)-piperidin-1-ylmethyl]-benzoic acid A. Preparation of 4-(1-furan-2-ylmethyl-1H-indol-3-yl)-piperidine-1-carboxylic acid ethyl ester This compound was prepared following the procedure described in example 13 (part B) starting with 9.4 g (34.4 mmol) of 4-(1H-indol-3-yl)-piperidine-1-carboxylic acid ethyl ester and 40 mL of (40 mmol) of a freshly prepared 1M solution in ethyl ether of 2-bromomethyl-furan. The reaction mixture was stirred at room temperature for 18 hours. After standard work-up, 13.2 g (100% of yield) of 4-(1-furan-2-ylmethyl-1H-indol-3-yl)-piperidine-1-carboxylic acid ethyl ester were obtained.

B. Preparation of 1-furan-2-ylmethyl-3-piperidin-4-yl-1H-indole

This compound was prepared following the procedure described in example 13 (part C) starting with 13.2 g (37 mmol) of 4-(1-furan-2-ylmethyl-1H-indol-3-yl)-piperidine-1-carboxylic acid ethyl ester. After standard work-up, 10.2 g (98% of yield) of 1-furan-2-ylmethyl-3-piperidin-4-yl-1H-indole were obtained.

C. 3-[4-(1-furan-2-ylmethyl-1H-indol-3-yl)-piperidin-1-ylmethyl]-benzoic acid

This compound was prepared following the procedure described in example 13 (part D) starting with 2.8 g (10 mmol) of 1-furan-2-ylmethyl-3-piperidin-4-yl-1H-indole and 2.5 g (11 mmol) of 3-bromomethyl-benzoic acid methyl ester. After standard work-up, 1.5 g (36% of yield) of the expected acid were obtained.

Melting point 154–155° C.

NMR (300 MHz, DMSO)=1.61–1.76 (m, 2H), 1.90–1.95 (m, 2H), 2.12–2.20 (t, 2H), 2.72–2.80 (m, 1H), 2.89–2.92 (m, 2H), 3.59 (s, 2H), 5.33 (s, 2H), 6.37–6.44 (m, 2H), 6.96–7.01 (m, 1H), 7.08–7.13 (m, 2H), 7.44–7.57 (m, 5H), 7.83–7.85 (m, 1H), 7.93 (s, 1H).

EXAMPLE 84

Preparation of 2-(2-{4-[1-(2-[1,4]dioxan-2-yl-ethyl)-1H-indol-3-yl]-piperidin-1-yl}-ethoxy)-benzoic acid This compound was prepared following the procedure described in example 13 (part D) starting with 0.58 g (1.84 mmol) of 1-(2-[1,4]dioxan-2-yl-ethyl)-3-piperidin-4-yl-1H-indole (example 71, part B) and 0.51 g (2.39 mmol) of 2-(2-chloro-ethoxy)-benzoic acid methyl ester. After standard work-up and purification by flash chromatography over silica gel, 0.18 g (20% of yield) of the expected acid were obtained.

Melting point 139–140° C.

NMR (300 MHz, DMSO)=1.70–1.82 (m, 2H), 1.91–2.08 (m, 4H), 2.66–2.73 (m, 2H), 2.93–3.10 (m, 3H), 3.11–3.27 (m, 4H), 3.44–3.64 (m, 4H), 3.76–3.79 (m, 1H), 4.18–4.22 (m, 2H), 4.42–4.46 (m, 2H), 6.97–7.04 (m, 2H), 7.12–7.15 (m, 2H), 7.22–7.25 (m, 1H), 7.37–7.41 (m, 2H), 7.52–7.54 (d, 1H), 7.64–7.66 (d, 1H).

EXAMPLE 85

Preparation of 5-[4-(1-furan-2-ylmethyl-1H-indol-3-yl)-piperidin-1-ylmethyl]-2-methoxy-benzoic acid This compound was prepared following the procedure described in example 13 (part D) starting with 1.9 g (6.5 mmol) of 1-furan-2-ylmethyl-3-piperidin-4-yl-1H-indole (example 83, part B) and 1.9 g (7.1 mmol) of 5-bromomethyl-2-methoxy-benzoic acid ethyl ester. After standard work-up and recrystallisation with ethanol, 0.5 g (16% of yield) of the expected acid were obtained.

Melting point 237–238° C.

NMR (300 MHz, DMSO)=1.65–1.75 (m, 2H), 1.90–1.95 (m, 2H), 2.11–2.18 (t, 2H), 2.68–2.83 (m, 1H), 2.89–2.93 (m, 2H), 3.50 (s, 2H), 3.81 (s, 3H), 5.33 (m, 2H), 6.37–6.44 (m, 2H), 6.96–7.17 (m, 4H), 7.42–7.59 (m, 5H).

EXAMPLE 86

Preparation of 5-[4-(1-furan-3-ylmethyl-1H-indol-3-yl)-piperidin-1-ylmethyl]-2-methoxy-benzoic acid A. Preparation of 4-(1-furan-3-ylmethyl-1H-indol-3-yl)-piperidine-1-carboxylic acid ethyl ester This compound was prepared following the procedure described in example 13 (part B) starting with 4 g (13.7 mmol) 4-(1H-indol-3-yl)-piperidine-1-carboxylic acid ethyl ester and 16 mL (16 mmol) of a freshly prepared 1M solution in ethyl ether of 3-bromomethyl-furan. The reaction mixture was stirred at room temperature for 18 hours. After standard work-up, 5.3 g (99% of yield) of 4-(1-furan-3-ylmethyl-1H-indol-3-yl)-piperidine-1-carboxylic acid ethyl ester were obtained.

B. Preparation of 1-furan-3-ylmethyl-3-piperidin-4-yl-1H-indole

This compound was prepared following the procedure described in example 13 (part C) starting with 7.3 g (20 mmol) of 4-(1-furan-3-ylmethyl-1H-indol-3-yl)-piperidine-1-carboxylic acid ethyl ester. After standard work-up, 5.6 g (99% of yield) of 1-furan-3-ylmethyl-3-piperidin-4-yl-1H-indole were obtained.

C. 5-[4-(1-furan-3-ylmethyl-1H-indol-3-yl)-piperidin-1-ylmethyl]-2-methoxy-benzoic acid This compound was prepared following the procedure described in example 13 (part D) starting with 1.9 g (6.5 mmol) of 1-furan-3-ylmethyl-3-piperidin-4-yl-1H-indole and 1.9 g (7.1 mmol) 5-bromomethyl-2-methoxy-benzoic acid ethyl ester. After standard work-up, 1.2 g (42% of yield) of the expected acid were obtained.

Melting point 253–255° C.

NMR (300 MHz, DMSO)=1.61–1.78 (m, 2H), 1.91–1.95 (m, 2H), 2.08–2.12 (m, 2H), 2.72–2.82 (m, 1H), 2.91–2.94 (m, 2H), 3.52–3.62 (m, 2H), 3.81 (s, 3H), 5.14 (s, 2H), 6.38 (s, 1H), 6.95–7.00 (t, 1H), 7.08–7.11 (m, 2H), 7.21 (s, 1H), 7.44–7.60 (m, 5H), 7.69 (s, 1H).

EXAMPLE 87

Preparation of 3-{4-[5-methoxy-1-(2-thiophen-3-yl-ethyl)-1H-indol-3-yl]-piperidin-1-ylmethyl}-benzoic acid A. Preparation of 5-methoxy-3-piperidin-4-yl-1H-indole This compound was prepared following the procedure described in example 1 (parts A and B) starting with 5.9 g (40 mmol) of 5-methoxyindol and 15.5 g (100 mmol) of 4-piperidone. In this case the hydrogenation took place for 24 hours at 30 psi and the catalyst used was platinum (IV) oxide. 6.8 g (74% of yield) of 5-methoxy-3-piperidin-4-yl-1H-indole were obtained.

B. Preparation of 4-(5-methoxy-1H-indol-3-yl)-piperidine-1-carboxylic acid ethyl ester This compound was prepared following the procedure described in example 13 (part A) starting with 5.8 g (25 mmol) of 5-methoxy-3-piperidin-4-yl-1H-indole. After standard work-up, 6.9 g (91% of yield) of 4-(5-methoxy-1H-indol-3-yl)-piperidine-1-carboxylic acid ethyl ester were obtained.

C. Preparation of 4-[5-methoxy-1-(2-thiophen-3-yl-ethyl)-1H-indol-3-yl]-piperidine-1-carboxylic acid ethyl ester This compound was prepared following the procedure described in example 13 (part B) starting with 8.7 g (28.6 mmol) of 4-(5-methoxy-1H-indol-3-yl)-piperidine-1-carboxylic acid ethyl ester and 6.9 g (33.4 mmol) of 2-thiophen-3-yl-ethyl methanesulfonate. The reaction mixture was stirred at room temperature for 18 hours. After standard work-up, 6.7 g (57% of yield) of 4-[5-methoxy-1-(2-thiophen-3-yl-ethyl)-1H-indol-3-yl]-piperidine-1-carboxylic acid ethyl ester were obtained.

D. Preparation of 5-methoxy-3-piperidin-4-yl-1-(2-thiophen-3-yl-ethyl)-1H-indole This compound was prepared following the procedure described in example 13 (part C) starting with 6.6 g (16 mmol) of 4-[5-methoxy-1-(2-thiophen-3-yl-ethyl)-1H-indol-3-yl]-piperidine-1-carboxylic acid ethyl ester. After standard work-up, 5.3 g (97% of yield) of 5-methoxy-3-piperidin-4-yl-1-(2-thiophen-3-yl-ethyl)-1H-indole were obtained.

E. Preparation of 3-{4-[5-methoxy-1-(2-thiophen-3-yl-ethyl)-1H-indol-3-yl]-piperidin-1-ylmethyl}-benzoic acid This compound was prepared following the procedure described in example 13 (part D) starting with 1.7 g (5 mmol) of 5-methoxy-3-piperidin-4-yl-1-(2-thiophen-3-yl-ethyl)-1H-indole and 1.3 g (5.5 mmol) of 3-bromomethyl-benzoic acid methyl ester. After standard work-up, 0.8 g (34% of yield) of the expected acid were obtained.

Melting point 217–218° C.

NMR (300 MHz, DMSO)=1.60–1.67 (m, 2H), 1.88–1.91 (m, 2H), 2.12–2.20 (t, 2H), 2.64–2.72 (m, 1H), 2.88–2.92 (m, 2H), 2.99–3.04 (m, 2H), 3.59 (s, 2H), 3.75 (s, 3H), 4.25–4.30 (m, 2H), 6.71–6.75 (m, 1H), 6.96–7.02 (m, 3H), 7.14–7.16 (m, 1H), 7.31–7.34 (d, 1H), 7.42–7.48 (m, 2H), 7.56–7.58 (d, 1H), 7.83–7.85 (d, 1H), 7.93 (s, 1H).

EXAMPLE 88

Preparation of 2-(2-{4-[5-methoxy-1-(2-thiophen-3-yl-ethyl)-1H-indol-3-yl]-piperidin-1-yl}-ethoxy)-benzoic acid This compound was prepared following the procedure described in example 87 (part E) starting with 1.7 g (5 mmol) of 5-methoxy-3-piperidin-4-yl-1-(2-thiophen-3-yl-ethyl)-1H-indole and 1.2 g (5.5 mmol) of 2-(2-chloro-ethoxy)-benzoic acid methyl ester. After standard work-up and purification by flash chromatography, 0.6 g (24% of yield) of the expected acid were obtained.

Melting point 145–148° C.

NMR (300 MHz, DMSO)=1.94–2.03 (m, 4H), 2.64–2.67 (m, 2H), 2.82–2.87 (m, 1H), 2.98–3.05 (m, 4H), 3.21–3.25 (m, 2H), 3.80 (s, 3H), 4.27–4.32 (m, 2H), 4.46 (s, 2H), 6.73–6.77 (dd, 1H), 6.99–7.04 (m, 3H), 7.13 (s, 1H), 7.19–7.22 (m, 2H), 7.33–7.37 (m, 2H), 7.40–7.51 (m, 1H), 7.533–7.58 (m, 1H).

EXAMPLE 89

Preparation of 2-{2-[4-(5-methoxy-1-thiophen-2-ylmethyl-1H-indol-3-yl)-piperidin-1-yl]-ethoxy}-benzoic acid A. Preparation of 4-(5-methoxy-1-thiophen-2-ylmethyl-1H-indol-3-yl)-piperidine-1-carboxylic acid ethyl ester This compound was prepared following the procedure described in example 13 (part B) starting with 9.1 g (30 mmol) of 4-(5-methoxy-1H-indol-3-yl)-piperidine-1-carboxylic acid ethyl ester (example 87, part B) and 50 mL (50 mmol) of a freshly prepared 1M solution in ethyl ether of 2-bromomethyl-thiophene. The reaction mixture was stirred at room temperature for 18 hours. After standard work-up, 7.7 g (65% of yield) of 4-(5-methoxy-1-thiophen-2-ylmethyl-1H-indol-3-yl)-piperidine-1-carboxylic acid ethyl ester were obtained.

B. Preparation of 5-methoxy-3-piperidin-4-yl-1-thiophen-2-ylmethyl-1H-indole

This compound was prepared following the procedure described in example 13 (part C) starting with 7.7 g (19 mmol) of 4-(5-methoxy-1-thiophen-2-ylmethyl-1H-indol-3-yl)-piperidine-1-carboxylic acid ethyl ester. After standard work-up, 5 g (81% of yield) of 5-methoxy-3-piperidin-4-yl-1-thiophen-2-ylmethyl-1H-indole were obtained.

C. Preparation of 2-{2-[4-(5-methoxy-1-thiophen-2-ylmethyl-1H-indol-3-yl)-piperidin-1-yl]-ethoxy}-benzoic acid This compound was prepared following the procedure described in example 13 (part D) starting with 2.4 g (7.4 mmol) of 5-methoxy-3-piperidin-4-yl-1-thiophen-2-ylmethyl-1H-indole and 1.8 g (8 mmol) of 2-(2-chloro-ethoxy)-benzoic acid methyl ester. After standard work-up, 1.3 g (36% of yield) of the expected acid were obtained.

Melting point 150–151° C.

NMR (300 MHz, DMSO)=1.94–2.10 (m, 4H), 2.63–2.70 (m, 2H), 2.86–2.98 (m, 3H), 3.22–3.26 (m, 2H), 3.79 (s, 3H), 4.44–4.47 (m, 2H), 4.80–5.25 (m, 1H), 5.50 (s, 2H), 6.74–6.77 (dd, 1H), 6.93–7.24 (m, 6H), 7.35–7.41 (m, 2H), 7.50–7.53 (dd, 1H).

EXAMPLE 90

Preparation of 3-[4-(5-methoxy-1-thiophen-2-ylmethyl-1H-indol-3-yl)-piperidin-1-ylmethyl]-benzoic acid This compound was prepared following the procedure described in example 13 (part D) starting with 2.4 g (7.4 mmol) of 5-methoxy-3-piperidin-4-yl-1-thiophen-2-ylmethyl-1H-indole (example 89, part C) and 1.9 g (8 mmol) 3-bromomethyl-benzoic acid methyl ester. After standard work-up, 1.4 g (41% of yield) of the expected acid were obtained.

Melting point 185–186° C.

NMR (300 MHz, DMSO)=1.60–1.76 (m, 2H), 1.91–1.95 (m, 2H), 2.16–2.23 (m, 2H), 2.70–2.78 (m, 1H), 2.91–2.94 (m, 2H), 3.56 (s, 2H), 3.74 (s, 3H), 5.47 (s, 2H), 6.72–6.76 (dd, 1H), 6.92–6.95 (m, 1H), 7.01–7.02 (m, 1H), 7.06–7.07 (m, 1H), 7.20 (s, 1H), 7.33–7.60 (m, 4H), 7.84–7.86 (d, 1H), 7.94 (s, 1H).

EXAMPLE 91

Preparation of 2-methoxy-5-{4-[5-methoxy-1-(2-thiophen-3-yl-ethyl-1H-indol-3-yl]-piperidin-1-ylmethyl}-benzoic acid This compound was prepared following the procedure described in example 13 (part D) starting with 1.95 g (5.7 mmol) of 5-methoxy-3-piperidin-4-yl-1-thiophen-2-ylmethyl-1H-indole (example 87, part E) and 1.7 g (6.2 mmol) of 5-bromomethyl-2-methoxy-benzoic acid ethyl ester. After standard work-up, 1 g (35% of yield) of the expected acid were obtained.

Melting point 229–230° C.

NMR (300 MHz, DMSO)=1.55–1.66 (m, 2H), 1.87–1.92 (m, 2H), 2.08–2.16 (m, 2H), 2.53–2.74 (m, 1H), 2.87–2.91 (m, 2H), 2.99–3.04 (m, 2H), 3.48 (s, 2H), 3.75 (s, 3H), 3.81 (s, 3H), 4.25–4.30 (t, 2H), 6.72–6.75 (d, 1H), 6.96–7.01 (m, 3H), 7.07–7.10 (d, 1H), 7.16 (s, 1H), 7.32–7.34 (d, 1H), 7.42–7.45 (m, 3H), 7.58 (s, 1H).

EXAMPLE 92

Preparation of 2-{2-[4-(1-furan-3-ylmethyl-5-methoxy-1H-indol-3-yl)-piperidin-1-yl]-ethoxy}-benzoic acid A. Preparation of 4-(1-furan-3-ylmethyl-5-methoxy-1H-indol-3-yl)-piperidine-1-carboxylic acid ethyl ester This compound was prepared following the procedure described in example 13 (part B) starting with 8 g (26.4 mmol) of 4-(5-methoxy-1H-indol-3-yl)-piperidine-1-carboxylic acid ethyl ester (example 87, part B) and 30 mL (30 mmol) of a freshly prepared 1M solution in ethyl ether of 3-bromomethyl-furan. The reaction mixture was stirred at room temperature for 18 hours. After standard work-up, 9.9 g (99% of yield) of 4-(1-furan-3-ylmethyl-5-methoxy-1H-indol-3-yl)-piperidine-1-carboxylic acid ethyl ester were obtained.

B. Preparation of 1-furan-3-ylmethyl-5-methoxy-3-piperidin-4-yl-1H-indole

This compound was prepared following the procedure described in example 13 (part C) starting with 9.9 g (25.8 mmol) of 4-(1-furan-3-ylmethyl-5-methoxy-1H-indol-3-yl)-piperidine-1-carboxylic acid ethyl ester. After standard work-up, 7.5 g (94% of yield) of 1-furan-3-ylmethyl-5-methoxy-3-piperidin-4-yl-1H-indole were obtained.

C. Preparation of 2-{2-[4-(1-furan-3-ylmethyl-5-methoxy-1H-indol-3-yl)-piperidin-1-yl]-ethoxy}-benzoic acid This compound was prepared following the procedure described in example 13 (part D) starting with 3.7 g (11.9 mmol) of 1-furan-3-ylmethyl-5-methoxy-3-piperidin-4-yl-1H-indole and 3 g (13.9 mmol) of 2-(2-chloro-ethoxy)-benzoic acid methyl ester. After standard work-up, 3.2 g (57% of yield) of the expected acid were obtained.

Melting point 153–154° C.

NMR (300 MHz, DMSO)=1.86–2.02 (m, 4H), 2.63–2.69 (m, 2H), 2.79–2.99 (m, 3H), 3.21–3.26 (m, 2H), 3.79 (s, 3H), 4.43–4.47 (m, 2H), 5.12 (s, 2H), 6.38 (s, 1H), 6.73–6.76 (dd, 1H), 6.99–7.04 (t, 1H), 7.15–7.16 (m, 2H), 7.22–7.25 (d, 1H), 7.35–7.40 (m, 2H), 7.50–7.52 (d, 1H), 7.56 (s, 1H), 7.69 (s, 1H).

EXAMPLE 93

Preparation of 3-[4-(1-furan-3-ylmethyl-5-methoxy-1H-indol-3-yl)-piperidin-1-ylmethyl]-benzoic acid This compound was prepared following the procedure described in example 13 (part D) starting with 3.7 g (11.9 mmol) of 1-furan-3-ylmethyl-5-methoxy-3-piperidin-4-yl-1H-indole (example 92, part B) and 3 g (13 mmol) of 3-bromomethyl-benzoic acid methyl ester. After standard work-up, 2.4 g (45% of yield) of the expected acid were obtained. In this case a p-tolensulfonate derivative salt was prepared affording 2.9 g of white solid.

Melting point 214–215° C.

NMR (300 MHz, DMSO)=1.78–1.91 (m, 2H), 2.13–2.18 (m, 2H), 2.28 (s, 3H), 2.94–3.12 (m, 3H), 3.46–3.49 (d, 2H), 3.75 (s, 3H), 4.45 (s, 2H), 5.12 (s, 2H), 6.34 (s, 1H), 6.76–6.79 (dd, 1H), 7.10–7.18 (s, 4H), 7.39–7.66 (m, 6H), 7.79–7.81 (d, 1H), 8.04–8.06 (d, 1H), 8.20 (s, 1H).

EXAMPLE 94

Preparation of 2-[4-(1-furan-2-ylmethyl-1H-indol-3-yl)-piperidin-1-ylmethyl]-benzoic acid This compound was prepared following the procedure described in example 13 (part D) starting with 0.05 g (0.18 mmol) of 1-furan-2-ylmethyl-3-piperidin-4-yl-1H-indole (example 83, part B) and 0.056 g (0.23 mmol) of 2-bromomethyl-benzoic acid ethyl ester. After standard work-up and purification using a C18 chromatography column, 0.014 g (19% of yield) of the expected acid were obtained.

NMR (300 MHz, CDCl$_3$)=1.91–2.03 (m, 2H), 2.13–2.18 (m, 2H), 2.55–2.68 (m, 2H), 2.95–3.30 (m, 1H), 3.26–3.30

(m, 2H), 3.98 (s, 2H), 5.18 (m, 2H), 6.24–6.25 (d, 1H), 6.30–6.31 (m, 1H), 6.90 (s, 1H), 7.08–7.13 (t, 1H), 7.20–7.50 (m, 6H), 7.54–7.56 (d, 1H), 8.19–8.22 (dd, 1H).

EXAMPLE 95

Preparation of 2-[4-(6-fluoro-1-furan-2-ylmethyl-1H-indol-3-yl)-piperidin-1-ylmethyl]-benzoic acid This compound was prepared following the procedure described in example 13 (part B) at room temperature for 15 hours, starting with 0.3 g (1.0 mmol) of 4-(6-fluoro-1H-indol-3-yl)-piperidine-1-carboxylic acid ethyl ester and 2.7 mL (1.6 mmol) of a freshly prepared 0.61 M solution of 2-bromomethylfuran in ethyl ether. After standard work-up, 0.38 g (100% of yield) of 4-(6-fluoro-1-furan-2-ylmethyl-1H-indol-3-yl)-piperidine-1-carboxylic acid ethyl ester were obtained.

B. Preparation of 6-fluoro-1-furan-2-ylmethyl-3-piperidin-4-yl-1H-indole

This compound was prepared following the procedure described in example 13 (part C) starting with 0.38 g (1.1 mmol) of 4-(6-fluoro-1-furan-2-ylmethyl-1H-indol-3-yl)-piperidine-1-carboxylic acid ethyl ester. After standard work-up, 0.27 g (89% of yield) of 6-fluoro-1-furan-2-ylmethyl-3-piperidin-4-yl-1H-indole were obtained.

C. Preparation of 2-[4-(6-fluoro-1-furan-2-ylmethyl-1H-indol-3-yl)-piperidin-1-ylmethyl]-benzoic acid This compound was prepared following the procedure described in example 13 (part D) starting with 0.05 g (0.17 mmol) and 0.054 g (0.22 mmol) of 2-bromomethyl-benzoic acid ethyl ester. After standard work-up and purification using a C18 chromatography column, 0.021 g (29% of yield) of the expected acid were obtained.

NMR (300 MHz, CDCl$_3$)=1.95–2.04 (m, 2H), 2.18–2.22 (m, 2H), 2.72–2.88 (m, 3H), 3.37–3.41 (m, 2H), 4.10 (s, 2H), 5.14 (s, 2H), 6.27–6.28 (d, 1H), 6.31–6.33 (dd, 1H), 6.83–6.90 (td, 1H), 6.93 (s, 1H), 7.07–7.11 (dd, 1H), 7.23–7.26 (d, 1H), 7.36–7.53 (m, 4H), 8.11–8.14 (dd, 1H).

EXAMPLES 96 AND 97

These compounds were prepared following the procedure described in example 95. The ESI/MS data, yields and purity are summarised in table 13.

TABLE 13

Examples 96–97

| Example | ESI/MS m/e [(M + 1)$^+$] | Yield % (mg obtained) | Purity % |
|---|---|---|---|
| 96 | 433 | 10% (6 mg) | 98 |
| 97 | 463 | 16% (13 mg) | 100 |

EXAMPLE 98

Preparation of 4-methoxy-2-[4-(5-methoxy-1-thiophen-2-ylmethyl-1H-indol-3-yl)-piperidin-1-ylmethyl]-benzoic acid This compound was prepared following the procedure described in example 13 (part D) starting with 0.06 g (0.19 mmol) of 5-methoxy-3-piperidin-4-yl-1-thiophen-2-ylmethyl-1H-indole (example 89, part B) and 0.064 g (0.23 mmol) of 2-bromomethyl-4-methoxy-benzoic acid methyl ester. After standard work-up and purification by chromatography using a C18 column, 0.018 g (19% of yield) of the expected acid were obtained.

NMR (300 MHz, DMSO)=1.58–1.72 (m, 2H), 2.07–2.11 (m, 2H), 2.69–2.77 (t, 2H), 2.82–3.11 (m, 3H), 3.76 (s, 3H), 3.81 (s, 3H), 4.02 (s, 2H), 5.49 (s, 2H), 6.76–6.79 (dd, 1H), 6.92–6.99 (m, 3H), 7.06 (s, 1H), 7.35–7.05 (m, 2H), 7.88–7.91 (d, 1H).

EXAMPLES 99–100

These compounds were prepared following the procedure described in example 98. The ESI/MS data, yields and purity are summarised in table 14.

TABLE 14

Examples 99–100

| Example | ESI/MS m/e [(M + 1)$^+$] | Yield % (mg obtained) | Purity % |
|---|---|---|---|
| 99 | 461 | 47% (28 mg) | 67 |
| 100 | 491 | 15% (14 mg) | 77 |

EXAMPLE 101

Preparation of 2-[4-(1-furan-2-ylmethyl-5-methoxy-1H-indol-3-yl)-piperidin-1-ylmethyl]-4-methoxy-benzoic acid A. Preparation of 4-(1-furan-2-ylmethyl-5-methoxy-1H-indol-3-yl)-piperidine-1-carboxylic acid ethyl ester This compound was prepared following the procedure described in example 13 (part B) at room temperature for 15 hours, starting with 0.3 g (1.0 mmol) of 4-(5-methoxy-1H-indol-3-yl)-piperidine-1-carboxylic acid ethyl ester and 2.11 mL (1.3 mmol) of a freshly prepared 0.61 M solution of 2-bromomethylfuran in ethyl ether. After standard work-up, 0.38 g (100% of yield) of 4-(1-furan-2-ylmethyl-5-methoxy-1H-indol-3-yl)-piperidine-1-carboxylic acid ethyl ester were obtained.

B. Preparation of 1-furan-2-ylmethyl-5-methoxy-3-piperidin-4-yl-1H-indole

This compound was prepared following the procedure described in example 13 (part C) starting with 0.38 g (1.1 mmol) of 4-(1-furan-2-ylmethyl-5-methoxy-1H-indol-3-yl)-piperidine-1-carboxylic acid ethyl ester. After standard work-up, 0.27 g (86% of yield) 1-furan-2-ylmethyl-5-methoxy-3-piperidin-4-yl-1H-indole were obtained.

C. Preparation of 2-[4-(1-furan-2-ylmethyl-5-methoxy-1H-indol-3-yl)-piperidin-1-ylmethyl]-4-methoxy-benzoic acid This compound was prepared following the procedure described in example 13 (part D) starting with 0.05 g (0.17 mmol) of 1-furan-2-ylmethyl-5-methoxy-3-piperidin-4-yl-1H-indole and 0.057 g (0.22 mmol) of 2-bromomethyl-4-methoxy-benzoic acid methyl ester. After standard work-up and purification by chromatography using a C18 column, 0.029 g (36% of yield) of the expected acid were obtained.

NMR (300 MHz, DMSO)=1.64–1.75 (m, 2H), 2.07–2.12 (m, 2H), 2.75–2.83 (m, 2H), 2.88–3.00 (m, 1H), 3.12–3.16 (d, 2H), 3.76 (s, 3H), 3.82 (s, 3H), 4.08 (s, 2H), 5.29 (s, 2H), 6.37–6.43 (m, 2H), 6.76–6.80 (dd, 1H), 6.99–7.07 (m, 2H), 7.18 (s, 1H), 7.40–7.43 (d, 1H), 7.55 (s, 1H), 7.90–7.93 (s, 1H).

EXAMPLES 102–105

These compounds were prepared following the procedure described in example 101. The ESI/MS data, yields and purity are summarised in table 15.

TABLE 15

Examples 102–105

| Example | ESI/MS m/e [(M + 1)⁺] | Yield % (mg obtained) | Purity % |
|---|---|---|---|
| 102 | 445 | 24% (18 mg) | 85 |
| 103 | 445 | 38% (24 mg) | 64 |
| 104 | 475 | 23% (18 mg) | 98 |
| 105 | 475 | 18% (14 mg) | 74 |

EXAMPLE 106

Preparation of 4-methoxy-2-{4-[5-methoxy-1-(2-thiophen-3-yl-ethyl)-1H-indol-3-yl]-piperidin-1-ylmethyl}-benzoic acid This compound was prepared following the procedure described in example 13 (part D) starting with 0.05 g (0.16 mmol) of 5-methoxy-3-piperidin-4-yl-1-(2-thiophen-3-yl-ethyl)-1H-indole (example 87, part D) and 0.054 g (0.21 mmol) of 2-bromomethyl-4-methoxy-benzoic acid methyl ester. After standard work-up and purification by chromatography using a C18 column, 0.019 g (24% of yield) of the expected acid were obtained.

NMR (300 MHz, DMSO)=1.59–1.71 (m, 2H), 2.04–2.08 (m, 2H), 2.69–2.77 (m, 2H), 2.89–3.10 (m, 5H), 3.77 (s, 3H), 3.81 (s, 3H), 4.02 (s, 2H), 4.26–4.31 (t, 2H), 6.74–6.77 (dd, 1H), 6.97–7.01 (m, 3H), 7.04–7.05 (d, 1H), 7.08 (s, 1H), 7.15–7.18 (m, 1H), 7.34–7.37 (d, 1H), 7.43–7.45 (dd, 1H), 7.88–7.91 (d, 1H).

EXAMPLE 107

Preparation of 2-{2-[4-(6-fluoro-1-thiophen-2-ylmethyl-1H-indol-3-yl)-piperidin-1-yl]-ethoxy}-benzoic acid This compound was prepared following the procedure described in example 13 (part D) starting with 0.1 g (0.33 mmol) of 6-fluoro-3-piperidin-4-yl-1-thiophen-2-ylmethyl-1H-indole (example 82, part B) and 0.092 g (0.42 mmol) 2-(2-chloro-ethoxy)-benzoic acid acid methyl ester. The crude mixture was purified by HPLC-MS using a C-18 column.

NMR (300 MHz, DMSO)=1.86–2.10 (m, 4H), 2.73–2.80 (m, 2H), 2.90–2.99 (m, 1H), 3.05–3.12 (m, 2H), 3.30–3.34 (m, 2H), 4.40–4.48 (m, 2H), 5.53 (s, 2H), 6.83–6.90 (td, 1H), 6.95–6.98 (td, 1H), 7.00–7.05 (t, 1H), 7.14–7.15 (m, 1H), 7.21–7.26 (m, 2H), 7.39–7.44 (m, 3H), 7.55–7.58 (m, 1H), 7.64–7.69 (dd, 1H).

EXAMPLE 108

Preparation of 5-[4-(6-fluoro-1-thiophen-3-ylmethyl-1H-indol-3-yl)-piperidin-1-ylmethyl]-2-methoxy-benzoic acid A. Preparation of 4-(6-fluoro-1-thiophen-3-ylmethyl-1H-indol-3-yl)-piperidine-1-carboxylic acid ethyl ester This compound was prepared following the procedure described in example 13 (part B) at room temperature for 15 hours, starting with 0.1 g (0.34 mmol) of 4-(6-fluoro-1H-indol-3-yl)-piperidine-1-carboxylic acid ethyl ester and 0.77 mL (0.45 mmol) of a freshly prepared 0.58 M solution of 3-bromomethylthiophene in ethyl ether. After standard work-up, 0.13 g (100% of yield) 4-(6-fluoro-1-thiophen-3-ylmethyl-1H-indol-3-yl)-piperidine-1-carboxylic acid ethyl ester were obtained.

B. Preparation of 6-fluoro-3-piperidin-4-yl-1-thiophen-3-yl-methyl-1H-indole

This compound was prepared following the procedure described in example 13 (part C) starting with 0.13 g (0.34 mmol) of 4-(6-fluoro-1-thiophen-3-ylmethyl-1H-indol-3-yl)-piperidine-1-carboxylic acid ethyl ester. After standard work-up, 0.12 g (99% of yield) 6-fluoro-3-piperidin-4-yl-1-thiophen-3-ylmethyl-1H-indole were obtained.

C. 5-[4-(6-fluoro-1-thiophen-3-ylmethyl-1H-indol-3-yl)-piperidin-1-ylmethyl]-2-methoxy-benzoic acid This compound was prepared following the procedure described in example 13 (part D) starting with 0.12 g (0.34 mmol) of 6-fluoro-3-piperidin-4-yl-1-thiophen-3-ylmethyl-1H-indole and 0.11 g (0.44 mmol) of 5-bromomethyl-2-methoxy-benzoic acid ethyl ester. The crude mixture was purified by HPLC-MS using a C-18 column.

NMR (300 MHz, DMSO)=1.03–1.15 (m, 2H), 1.25–1.31 (m, 2H), 1.78–2.10 (m, 2H), 2.69–2.81 (m, 1H), 3.00–3.16 (m, 2H), 3.79–3.83 (m, 5H), 5.29 (s, 2H), 6.79–6.86 (t, 1H), 6.99–7.01 (d, 1H), 7.09–7.15 (m, 2H), 7.38–7.46 (m, 3H), 7.59–7.64 (m, 2H), 7.72 (s, 1H).

EXAMPLE 109

Preparation of 2-{2-[4-(6-fluoro-1-thiophen-3-ylm-ethyl-1H-indol-3-yl)-piperidin-1-yl]-ethoxy}-benzoic acid This compound was prepared following the procedure described in example 13 (part D) starting with 0.98 g (0.31 mmol) of 6-fluoro-3-piperidin-4-yl-1-thiophen-3-ylmethyl-1H-indole (example 108, part B) and 0.09 g (0.40 mmol) 2-(2-chloro-ethoxy)-benzoic acid methyl ester. The crude mixture was purified by HPLC-MS using a C-18 column.

NMR (300 MHz, DMSO)=1.90–2.10 (m, 4H), 2.62–2.71 (m, 2H), 2.78–3.10 (m, 3H), 3.22–3.26 (d, 2H), 4.34–4.39 (m, 2H), 5.30 (s, 2H), 6.82–6.88 (t, 1H), 6.99–7.04 (m, 2H), 7.22–7.28 (m, 2H), 7.37–7.47 (m, 4H), 7.53–7.55 (d, 1H), 7.64–7.69 (dd, 1H).

EXAMPLE 110

Preparation of 2-(2-{4-[6-fluoro-1-(2-thiophen-3-yl-ethyl)-1H-indol-3-yl]-piperidin-1-yl}-ethoxy)-benzoic acid This compound was prepared following the procedure described in example 13 (part D) starting with 0.1 g (0.31 mmol) of 6-fluoro-3-piperidin-4-yl-1-(2-thiophen-3-yl-ethyl)-1H-indole (example 78, part B) and 0.09 g (0.42 mmol) of 2-(2-chloro-ethoxy)-benzoic acid ethyl ester. After purification by HPLC-MS using a C-18 column, 0.01 g (99% of purity) of 2-(2-{4-[6-fluoro-1-(2-thiophen-3-yl-ethyl)-1H-indol-3-yl]-piperidin-1-yl}-ethoxy)-benzoic acid were obtained.

NMR (300 MHz, DMSO)=1.84–2.02 (m, 4H), 2.77–2.87 (m, 3H), 3.01–3.06 (t, 2H), 3.10–3.18 (m, 2H), 4.29–4.34 (t, 2H), 4.42–4.46 (m, 2H), 6.79–6.88 (td, 1H), 7.01–7.07 (m, 2H), 7.10 (s, 1H), 7.20–7.25 (m, 2H), 7.32–7.35 (dd, 1H), 7.41–7.47 (m, 2H), 7.57–7.65 (m, 2H).

EXAMPLES 111–112

These compounds were prepared following the procedure described in example 110 using the suitable halides. The ESI/MS data and purity are summarised in table 16.

TABLE 16

Example 111–112

| Example | ESI/MS m/e [(M + 1)⁺] | mg obtained | Purity % |
|---|---|---|---|
| 111 | 514 | 6 | 99 |
| 112 | 463 | 10 | 97 |

EXAMPLE 113

Preparation of 2-{2-[4-(5-methoxy-1-thiophen-3-ylmethyl-1H-indol-3-yl)-piperidin-1-yl]-ethoxy}-benzoic acid A. Preparation of 4-(5-methoxy-1-thiophen-3-ylmethyl-1H-indol-3-yl)-piperidine-1-carboxylic acid ethyl ester This compound was prepared following the procedure described in example 13 (part B) at room temperature for 15 hours, starting with 4 g (13.2 mmol) of 4-(5-methoxy-1H-indol-3-yl)-piperidine-1-carboxylic acid ethyl ester and 2.65 g (15 mmol) of 3-bromomethylthiophene. After standard work-up, 4.5 g (87% of yield) of 4-(5-methoxy-1-thiophen-3-ylmethyl-1H-indol-3-yl)-piperidine-1-carboxylic acid ethyl ester were obtained.

B. Preparation of 5-methoxy-3-piperidin-4-yl-1-thiophen-3-ylmethyl-1H-indole

This compound was prepared following the procedure described in example 13 (part C) starting with 4.5 g (11.2 mmol) of 4-(5-methoxy-1-thiophen-3-ylmethyl-1H-indol-3-yl)-piperidine-1-carboxylic acid ethyl ester. After standard work-up, 3.4 g (93% of yield) of 5-methoxy-3-piperidin-4-yl-1-thiophen-3-ylmethyl-1H-indole were obtained.

C. Preparation of 2-{2-[4-(5-methoxy-1-thiophen-3-ylmethyl-1H-indol-3-yl)-piperidin-1-yl]-ethoxy}-benzoic acid This compound was prepared following the procedure described in example 13 (part D) starting with 3.3 g (10 mmol) of 5-methoxy-3-piperidin-4-yl-1-thiophen-3-ylmethyl-1H-indole and 2.6 g (12 mmol) of 2-(2-chloroethoxy)-benzoic acid ethyl ester. After standard work-up and recrystallisation with ethanol, 1.8 g (37% of yield) of the expected acid were obtained.

NMR (300 MHz, DMSO)=1.82–2.02 (m, 4H), 2.62–2.69 (t, 2H), 2.79–2.98 (m, 3H), 3.21–3.25 (d, 2H), 3.79 (s, 3H), 4.43–4.47 (s, 2H), 5.38 (s, 2H), 6.72–6.75 (dd, 1H), 6.97–7.04 (m, 2H), 7.15 (s, 1H), 7.22–7.25 (m, 2H), 7.37–7.38 (m, 3H), 7.40–7.46 (m, 1H), 7.50–7.53 (dd, 1H).

EXAMPLES 114–116

These compounds were prepared following the procedure described in example 113 using 0.3 mmol of the suitable indols and halides. The crude mixtures were purified by HPLC-MS using a C-18 column. The ESI/MS data and purity are summarised in table 17.

TABLE 17

Examples 114–116

| Example | ESI/MS m/e [(M + 1)⁺] | mg obtained | Purity % |
|---|---|---|---|
| 114 | 461 | 3 | 100 |
| 115 | 526 | 7 | 98 |
| 116 | 496 | 3 | 100 |

EXAMPLE 117

Preparation of 2-methoxy-5-[4-(1-thiophen-3-ylmethyl-1H-indol-3-yl)-piperidin-1-ylmethyl]-benzoic acid A. Preparation of 4-(1-thiophen-3-ylmethyl-1H-indol-3-yl)-piperidine-1-carboxylic acid ethyl ester This compound was prepared following the procedure described in example 13 (part B) at room temperature for 15 hours, starting with 0.2 g (0.73 mmol) of 4-(1H-indol-3-yl)-piperidine-1-carboxylic acid ethyl ester and 1.64 mL (0.95 mmol) of a freshly prepared 0.6 M solution of 3-bromomethylthiophene in ethyl ether. After standard work-up, 0.27 g (100% of yield) of 4-(1-thiophen-3-ylmethyl-1H-indol-3-yl)-piperidine-1-carboxylic acid ethyl ester were obtained.

B. Preparation of 3-piperidin-4-yl-1-thiophen-3-ylmethyl-1H-indole

This compound was prepared following the procedure described in example 13 (part C) starting with 0.27 g (0.73 mmol) of 4-(1-thiophen-3-ylmethyl-1H-indol-3-yl)-piperidine-1-carboxylic acid ethyl ester. After standard work-up, 0.22 g (100% of yield) of 3-piperidin-4-yl-1-thiophen-3-ylmethyl-1H-indole were obtained.

C. Preparation of 2-methoxy-5-[4-(1-thiophen-3-ylmethyl-1H-indol-3-yl)-piperidin-1-ylmethyl]-benzoic acid This compound was prepared following the procedure described in example 13 (part D) starting with 0.1 g (0.38 mmol) of 3-piperidin-4-yl-1-thiophen-3-ylmethyl-1H-indole and 0.13 g (0.48 mmol) of 5-bromomethyl-2-methoxy-benzoic acid ethyl ester. The crude mixture was purified by HPLC-MS using a C-18 column, and 0.002 g (94% of purity) of the expected acid were isolated.

NMR (300 MHz, DMSO)=1.06–1.31 (m, 4H), 1.98–2.18 (m, 2H), 2.60–2.78 (m, 1H), 2.85–2.99 (m, 2H), 3.84 (s, 3H), 3.89–4.05 (m, 2H), 5.32 (s, 2H), 6.96–7.00 (m, 2H), 7.05–7.18 (m, 3H), 7.37 (s, 1H), 7.43–7.49 (m, 2H), 7.63–7.78 (m, 3H).

EXAMPLE 118

Preparation of 3-[4-(1-thiophen-3-ylmethyl-1H-indol-3-yl)-piperidin-1-ylmethyl]-benzoic acid This compound was prepared following the procedure described in example 117 (part C) starting with 0.1 g (0.38 mmol) of 3-piperidin-4-yl-1-thiophen-3-ylmethyl-1H-indole and 0.1 g (0.48 mmol) of 3-bromomethyl-benzoic acid methyl ester. The crude mixture was purified by HPLC-MS using a C-18 column, and 0.005 g (98% of purity) of the expected acid were isolated.

EXAMPLE 119

Preparation of 5-{4-[1-(5-chloro-thiophen-2-ylmethyl)-5-methoxy-1H-indol-3-yl]-piperidin-1-ylmethyl}-2-methoxy-benzoic acid A. Preparation of 4-[1-(5-chloro-thiophen-2-ylmethyl)-5-methoxy-1H-indol-3-yl]-piperidine-1-carboxylic acid ethyl ester This compound was prepared following the procedure described in example 13 (part B) at room temperature for 15 hours, starting with 0.1 g (0.33 mmol) of 4-(5-methoxy-1H-indol-3-yl)-piperidine-1-carboxylic acid ethyl ester and 0.052 mL (0.43 mmol) of 2-chloro-5-chloromethyl-thiophene. After standard work-up, 0.06 g (44% of yield) of 4-[1-(5-chloro-thiophen-2-ylmethyl)-5-methoxy-1H-indol-3-yl]-piperidine-1-carboxylic acid ethyl ester were obtained.

B. Preparation of 1-(5-chloro-thiophen-2-ylmethyl)-5-methoxy-3-piperidin-4-yl-1H-indole This compound was prepared following the procedure described in example 13 (part C) starting with 0.06 g (0.15 mmol) of 4-[1-(5-chloro-thiophen-2-ylmethyl)-5-methoxy-1H-indol-3-yl]-piperidine-1-carboxylic acid ethyl ester. After standard work-up, 0.05 g (89% of yield) 1-(5-chloro-thiophen-2-ylmethyl)-5-methoxy-3-piperidin-4-yl-1H-indole were obtained.

C. Preparation of 5-{4-[1-(5-chloro-thiophen-2-ylmethyl)-5-methoxy-1H-indol-3-yl]-piperidin-1-ylmethyl}-2-methoxy-benzoic acid This compound was prepared following the procedure described in example 13 (part D) starting with 0.05 g (0.13 mmol) 1-(5-chloro-thiophen-2-ylmethyl)-5-methoxy-3-piperidin-4-yl-1H-indole and 0.05 g (0.18 mmol) of 5-bromomethyl-2-methoxy-benzoic acid ethyl ester. The crude mixture was purified by HPLC-MS using a C-18 column, and 0.002 g (99% of purity) of the expected acid were isolated.

NMR (300 MHz, DMSO)=1.78–1.85 (m, 2H), 1.92–1.99 (m, 2H), 2.31–2.48 (m, 2H), 2.72–2.85 (m, 1H), 3.03–3.06 (m, 2H), 3.70–3.74 (m, 5H), 3.81 (s, 3H), 5.44 (s, 2H), 6.67–6.77 (m, 1H), 6.93–6.96 (m, 1H), 7.05–7.11 (m, 3H), 7.20 (s, 1H), 7.37–7.40 (d, 1H), 7.51–7.54 (d, 1H), 7.64 (s, 1H).

EXAMPLES 120–121

These compounds were prepared following the procedure described in example 119 with the corresponding halides. The crude mixtures were purified by flash chromatography using a C-18 column. The ESI/MS data and purity are summarised in table 18.

TABLE 18

Examples 120–121

| Example | ESI/MS m/e [(M + 1)+] | mg obtained | Purity % |
|---|---|---|---|
| 120 | 475 | 4 (12%) | 80 |
| 121 | 505 | 5 (14%) | 73 |

EXAMPLE 122

Preparation of a pharmaceutical composition: Syrup 1000 bottles (150 ml volume) each containing a solution of 750 mg of 2-(2-{4-[1-(2-[1,3]dioxolan-2-yl-ethyl)-6-fluoro-1H-indol-3-yl]-piperidin-1-yl}-ethoxy)-benzoic acid were prepared as follows:

| | |
|---|---|
| 2-(2-{4-[1-(2-[1,3]dioxolan-2-yl-ethyl)-6-fluoro-1H-indol-3-yl]-piperidin-1-yl}-ethoxy)-benzoic acid | 750 g |
| glycerin | 15,000 g |
| hydrogenated castor oil-ethylene oxide | 1,500 g |
| sodium methyl p-hydroxybenzoate | 240 g |
| sodium propyl p-hydroxybenzoate | 60 g |
| sodium saccharin | 300 g |
| flavouring | q.s. |
| sodium hydroxide q.s. | pH = 4 |
| demineralised water q.s. | 30 litres |

Procedure:

To a solution of the sodium methyl (and propyl) p-hydroxybenzoates and sodium saccharin in 30 liters of demineralised water, an aqueous glycerin solution and hydrogenated castor oil-ethylene oxide was added. After stirring, the 2-(2-{4-[1-(2-[1,3]dioxolan-2-yl-ethyl)-6-fluoro-1H-indol-3-yl]-piperidin-1-yl}-ethoxy)-benzoic acid was added and homogenized to reach complete dissolution. After this, the flavouring agent was mixed into the solution with vigorous stirring, and the mixture was made up to final volume with demineralised water.

The resultant solution was filled into 150 ml bottles using an appropriate filling machine.

EXAMPLE 123

Preparation of a pharmaceutical composition: capsules 50,000 capsules each containing 50 mg of 2-{2-[4-(1-thiophen-2-ylmethyl-1H-indol-3-yl)-piperidin-1-yl]-ethoxy}-benzoic acid were prepared from the following formulation:

| | |
|---|---|
| 2-{2-[4-(1-thiophen-2-ylmethyl-1H-indol-3-yl)-piperidin-1-yl]-ethoxy}-benzoic acid | 2,500 g |
| magnesium stearate | 225 g |
| lactose spray dried | 18,350 g |
| cross-linked sodium carboxymethylcellulose | 900 g |
| sodium lauryl sulphate | 450 g |

Procedure:

The 2-{2-[4-(1-thiophen-2-ylmethyl-1H-indol-3-yl)-piperidin-1-yl]-ethoxy}-benzoic acid, sodium lauryl sulphate, lactose and cross-linked sodium carboxymethylcellulose were mixed together and passed through a screen with an opening of 0.6 mm. The magnesium stearate was added and the mixture encapsulated into gelatine capsules of appropriate size.

EXAMPLE 124

Preparation of a pharmaceutical composition: tablets 100,000 tablets each containing 25 mg of 2-{2-[4-(1-pyridin-4-ylmethyl-1H-indol-3-yl)-piperidin-1-yl]-ethoxy}-benzoic acid were prepared from the following formulation:

| | |
|---|---|
| 2-(2-[4-(1-pyridin-4-ylmethyl-1H-indol-3yl)-piperidin-1-yl]-ethoxy}-benzoic acid | 2,500 g |
| microcrystalline cellulose | 1,650 g |
| lactose spray dried | 9,620 g |
| carboximethyl starch | 570 g |
| sodium stearyl fumarate | 80 g |
| colloidal silicon dioxide | 80 g |

Procedure:

All the powders were passed through a screen with apertures of 0.6 mm. They were then all mixture in a suitable mixer for 30 minutes and compressed into 145 mg tablets using 6 mm discs and flat bevelled punches. The desintegration time of the tablets was about 60 seconds.

The invention claimed is:
1. A compound of formula (I):

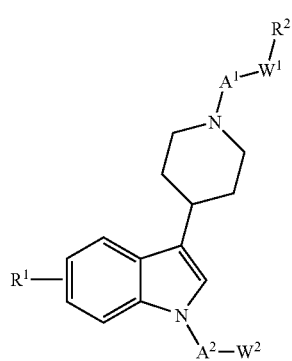

wherein:
$A^1$ represents an alkylene, alkyleneoxy, alkylenethio, alkanoylene or hydroxyalkylene group;
$A^2$ represents an alkylene, alkyleneoxy, alkylenethio, alkanoylene or an alkyleneoxyalkylene group;
$W^1$ represents a phenylene, furanylene or pyridinylene group which is unsubstituted or substituted by one or more halogen atoms, alkoxy groups and/or alkyl groups;
$W^2$ represents a 3–10 membered monocyclic or bicyclic group containing from 1 to 3 heteroatoms said group being unsubstituted or substituted by one or more halogen atoms, alkyl groups, alkoxy groups and/or oxo groups;
$R^1$ represents a hydrogen or halogen atom or an alkyl, alkoxy or methylamino group; and
$R^2$ represents a carboxyl group;
and pharmaceutically acceptable salts thereof.

2. A compound according to claim 1 wherein $A^1$ represents a $C_{1-3}$ alkylene, or $C_{1-5}$ alkyleneoxy group.

3. A compound according to claim 1 wherein $A^2$ represents a $C_{1-5}$ alkylene, $C_{1-5}$ alkanoylene, $C_{2-5}$ alkyleneoxy, $C_{2-5}$ alkylenethio or $C_{2-5}$ alkyleneoxy-$C_{1-5}$ alkylene group.

4. A compound according to claim 1 wherein $W^1$ represents an unsubstituted phenylene, furanylene or pyridinylene group or a phenylene group substituted by one or two substituents selected from fluorine atoms, chlorine atoms, bromine atoms, methyl groups and methoxy groups.

5. A compound according to claim 1 wherein the heteroatom(s) contained in the substituent $W^2$ are selected from oxygen, sulphur and nitrogen.

6. A compound according to claim 5 wherein $W^2$ represents a dioxolanyl, dioxanyl, pyrazolidinyl, isoindolinyl benzodioxolanyl, tetrahydropyranyl, tetrahydrofuranyl, oxetanyl, furanyl, thienyl, pyrrolyl, pyridinyl, imidazolyl, dihydrothiazolyl, benzothiazolyl, pyrrolidinyl, benzooxazolyl, benzothienyl, pyranyl, benzofuranyl, isobenzylfuranyl, chromenyl, pyrazolyl, oxazolyl, isooxazolyl, furazanyl, isochromanyl, chromanyl, pyrrolinyl, imidazolidinyl, imidazolinyl, pyrazolinyl, piperidyl, piperazinyl, indolinyl, morpholinyl, pyrazinyl, pyrimidinyl, pyridazinyl, indolizinyl, isoindolyl, indolyl, indazolyl, quinazolinyl, isoquinazolinyl, quinolyl, phthalazinyl, naphthyridinyl, quinoxalinyl, quinazolinyl or cinnolinyl group which is unsubstituted or substituted by one or more halogen atoms, $C_{1-7}$ alkyl groups, $C_{1-7}$ alkoxy groups and/or oxo groups.

7. A compound according to claim 6 wherein $W^2$ represents a dioxolanyl, dioxanyl, pyrazolidinyl, benzodioxolanyl, tetrahydropyranyl, tetrahydrofuranyl, oxetanyl, furanyl, thienyl, pyrrolyl, pyridinyl, pyrrolidinyl or benzooxazolyl group which is unsubstituted or substituted by one or more fluorine atoms, chlorine atoms, bromine atoms, $C_{1-4}$ alkyl groups, $C_{1-4}$ alkoxy groups and/or oxo groups.

8. A compound according to claim 1 wherein $R^1$ represents a hydrogen, fluorine, chlorine or bromine atom or a methyl, methoxy or methylamino group.

9. A compound of formula (I) according to claim 1 which is:
2-{2-[4-(1-[1,3]dioxolan-2-ylmethyl-1H-indol-3-yl)-piperidin-1-yl]-ethoxy}-benzoic acid;
2-(2-{4-[1-(tetrahydro-pyran-2-ylmethyl)-1H-indol-3-yl]-piperidin-1-yl}-ethoxy)-benzoic acid;
2-{2-[4-(1-pyridin-4-ylmethyl-1H-indol-3-yl)-piperidin-1-yl]-ethoxy}-benzoic acid;
2-(2-{4-[1-(3-pyrrol-1-yl-propyl)-1H-indol-3-yl]-piperidin-1-yl}-ethoxy)-benzoic acid;
2-(2-{4-[1-(3-thiophen-2-yl-propyl)-1H-indol-3-yl]-piperidin-1-yl}-ethoxy)-benzoic acid;
2-[2-(4-{1-[3-(1-methyl-1H-imidazol-2-ylsulfanyl)-propyl]-1H-indol-3-yl}-piperidin-1-yl)-ethoxy]-benzoic acid;
2-[2-(4-{1-[2-(2,5,5-trimethyl-[1,3]dioxan-2-yl)-ethyl]-1H-indol-3-yl}-piperidin-1-yl)-ethoxy]-benzoic acid;
2-{2-[4-(1-thiophen-2-ylmethyl-1H-indol-3-yl)-piperidin-1-yl]ethoxy}-benzoic acid;
2-{2-[4-(1-furan-2-ylmethyl-1H-indol-3-yl)-piperidin-1-yl]-ethoxy}-benzoic acid;
2-(2-{4-[1-(2-oxo-2-pyrrolidin-1-yl-ethyl)-1H-indol-3-yl]-piperidin-1-yl}-ethoxy)-benzoic acid;
2-{2-[4-(1-thiophen-3-ylmethyl-1H-indol-3-yl)-piperidin-1-yl]-ethoxy}-benzoic acid;
2-(2-{4-[1-(2-thiophen-2-yl-ethyl)-1H-indol-3-yl]-piperidin-1-yl}-ethoxy)-benzoic acid;
2-(2-{4-[1-(2-thiophen-3-yl-ethyl)-1H-indol-3-yl]-piperidin-1-yl}-ethoxy)-benzoic acid;
2-[2-(4-{1-[3-(tetrahydro-furan-2-yl)-propyl]-1H-indol-3-yl}-piperidin-1-yl)-ethoxy]-benzoic acid;
2-(2-{4-[1-(4-[1,3]dioxolan-2-yl-butyl)-1H-indol-3-yl]-piperidin-1-yl}-ethoxy)-benzoic acid;

2-[2-(4-{1-[3-(benzo[1,3]dioxol-5-yloxy)propyl]-1H-indol-3-yl}piperidin-1-yl)ethoxy]benzoic acid;
2-[2-(4-{1-[3-(1,3-dioxo-1,3-dihydro-isoindol-2-yl)-propyl]-1H-indol-3-yl}-piperidin-1-yl)-ethoxy]-benzoic acid;
2-{2-[4-(1-benzo[1,3]dioxol-5-ylmethyl-1H-indol-3-yl)-piperidin-1-yl]-ethoxy}-benzoic acid;
2-(2-{4-[1-(5-chloro-thiophen-2-ylmethyl)-1H-indol-3-yl]-piperidin-1-yl}-ethoxy)-benzoic acid;
2-[2-(4-{1-[4-(5-methyl-2-oxo-benzooxazol-3-yl)-butyl]-1H-indol-3-yl}-piperidin-1-yl)-ethoxy]-benzoic acid;
2-(2-{4-[1-(3-[1,3]dioxolan-2-yl-propyl)-1H-indol-3-yl]-piperidin-1-yl}-ethoxy)-benzoic acid;
2-{2-[4-(6-fluoro-1-furan-2-ylmethyl-1H-indol-3-yl)-piperidin-1-yl]-ethoxy}-benzoic acid;
2-(2-{4-[1-(2-[1,3]dioxolan-2-yl-ethyl)-1H-indol-3-yl]-piperidin-1-yl}-ethoxy)-benzoic acid;
2-(2-{4-[1-(2-[1,3]dioxolan-2-yl-ethyl)-6-fluoro-1H-indol-3-yl]-piperidin-1-yl}-ethoxy)-benzoic acid;
3-[4-(1-thiophen-2-ylmethyl-1H-indol-3-yl)-piperidin-1-ylmethyl]-benzoic acid;
3-[4-(1-pyridin-3-ylmethyl-1H-indol-3-yl)-piperidin-1-ylmethyl]-benzoic acid;
3-{4-[1-(5-chloro-thiophen-2-ylmethyl)-1H-indol-3-yl]-piperidin-1-ylmethyl}-benzoic acid;
3-{4-[1-(2-[1,3]dioxolan-2-yl-ethyl)-1H-indol-3-yl]-piperidin-1-ylmethyl}-benzoic acid;
3-{4-[1-(3-[1,3]dioxolan-2-yl-propyl)-1H-indol-3-yl]-piperidin-1-ylmethyl}-benzoic acid;
3-[4-(1-pyridin-4-ylmethyl-1H-indol-3-yl)-piperidin-1-ylmethyl]-benzoic acid;
3-(4-{1-[3-(benzo[1,3]dioxol-5-yloxy)-propyl]-1H-indol-3-yl}-piperidin-1-ylmethyl)-benzoic acid;
3-[4-(1-[1,3]dioxolan-2-ylmethyl-1H-indol-3-yl)-piperidin-1-ylmethyl]-benzoic acid;
3-[4-(1-pyridin-2-ylmethyl-1H-indol-3-yl)-piperidin-1-ylmethyl]-benzoic acid;
2-methoxy-5-[4-(1-pyridin-3-ylmethyl-1H-indol-3-yl)-piperidin-1-ylmethyl]-benzoic acid;
5-{4-[1-(2-[1,3]dioxolan-2-yl-ethyl)-1H-indol-3-yl]-piperidin-1-ylmethyl}-2-methoxy-benzoic acid;
5-{4-[1-(3-[1,3]dioxolan-2-yl-propyl)-1H-indol-3-yl]-piperidin-1-ylmethyl}-2-methoxy-benzoic acid;
2-methoxy-5-[4-(1-thiophen-2-ylmethyl-1H-indol-3-yl)-piperidin-1-ylmethyl]-benzoic acid;
2-methoxy-5-[4-(1-pyridin-4-ylmethyl-1H-indol-3-yl)-piperidin-1-ylmethyl]-benzoic acid;
4-bromo-3-[4-(1-[1,3]dioxolan-2-ylmethyl-1H-indol-3-yl)-piperidin-1-ylmethyl]-benzoic acid;
4-bromo-3-[4-(1-pyridin-3-ylmethyl-1H-indol-3-yl)-piperidin-1-ylmethyl]-benzoic acid;
4-bromo-3-{4-[1-(2-[1,3]dioxolan-2-yl-ethyl)-1H-indol-3-yl]-piperidin-1-ylmethyl}-benzoic acid;
4-bromo-3-{4-[1-(3-[1,3]dioxolan-2-yl-propyl)-1H-indol-3-yl]-piperidin-1-ylmethyl}-benzoic acid;
4-bromo-3-[4-(1-thiophen-2-ylmethyl-1H-indol-3-yl)-piperidin-1-ylmethyl]-benzoic acid;
2-{4-[5-methoxy-1-(2-thiophen-3-yl-ethyl)-1H-indol-3-yl]-piperidin-1-ylmethyl}-benzoic acid;
3-(4-{1-[3-(benzo[1,3]dioxol-5-yloxy)-propyl]-1H-indol-3-yl}-piperidin-1-ylmethyl)-4-bromo-benzoic acid;
2-fluoro-5-[4-(1-pyridin-3-ylmethyl-1H-indol-3-yl)-piperidin-1-ylmethyl]-benzoic acid;
5-{4-[1-(2-[1,3]dioxolan-2-yl-ethyl)-1H-indol-3-yl]-piperidin-1-ylmethyl}-2-fluoro-benzoic acid;
5-{4-[1-(3-[1,3]dioxolan-2-yl-propyl)-1H-indol-3-yl]-piperidin-1-ylmethyl}-2-fluoro-benzoic acid;
2-fluoro-5-[4-(1-pyridin-4-ylmethyl-1H-indol-3-yl)-piperidin-1-ylmethyl]-benzoic acid;
5-(4-{1-[3-(benzo[1,3]dioxol-5-yloxy)-propyl]-1H-indol-3-yl}-piperidin-1-ylmethyl)-2-fluoro-benzoic acid;
5-[4-(1-[1,3]dioxolan-2-ylmethyl-1H-indol-3-yl)-piperidin-1-ylmethyl]-2-fluoro-benzoic acid;
2-fluoro-5-[4-(1-pyridin-2-ylmethyl-1H-indol-3-yl)-piperidin-1-ylmethyl]-benzoic acid;
2-(2-{4-[1-(tetrahydro-furan-3-ylmethyl)-1H-indol-3-yl]-piperidin-1-yl}-ethoxy)-benzoic acid;
2-(2-{4-[1-(2-morpholin-4-yl-ethyl)-1H-indol-3-yl]-piperidin-1-yl}-ethoxy)-benzoic acid;
2-(2-{4-[1-(3-methyl-oxetan-3-ylmethyl)-1H-indol-3-yl]-piperidin-1-yl}-ethoxy)-benzoic acid;
2-{2-[4-(1-furan-3-ylmethyl-1H-indol-3-yl)-piperidin-1-yl]-ethoxy}-benzoic acid;
2-(2-{4-[1-(2-pyridin-2-yl-ethyl)-1H-indol-3-yl]-piperidin-1-yl}-ethoxy)-benzoic acid;
3-{4-[1-(tetrahydro-furan-3-ylmethyl)-1H-indol-3-yl]-piperidin-1-ylmethyl}-benzoic acid;
3-{4-[1-(3-methyl-oxetan-3-ylmethyl)-1H-indol-3-yl]-piperidin-1-ylmethyl}-benzoic acid;
3-{4-[1-(2-thiophen-3-yl-ethyl)-1H-indol-3-yl]-piperidin-1-ylmethyl}-benzoic acid;
3-[4-(1-furan-3-ylmethyl-1H-indol-3-yl)-piperidin-1-ylmethyl]-benzoic acid;
2-[4-(1-pyridin-3-ylmethyl-1H-indol-3-yl)-piperidin-1-ylmethyl]-nicotinic acid;
2-{4-[1-(2-morpholin-4-yl-ethyl)-1H-indol-3-yl]-piperidin-1-ylmethyl}-nicotinic acid;
2-[4-(1-thiophen-2-ylmethyl-1H-indol-3-yl)-piperidin-1-ylmethyl]-nicotinic acid;
3-{4-[1-(5-chloro-thiophen-2-ylmethyl)-6-fluoro-1H-indol-3-yl]-piperidin-1-ylmethyl}-benzoic acid;
3-{4-[6-fluoro-1-(2-thiophen-3-yl-ethyl)-1H-indol-3-yl]-piperidin-1-ylmethyl}-benzoic acid;
3-{4-[6-fluoro-1-(2-thiophen-2-yl-ethyl)-1H-indol-3-yl]-piperidin-1-ylmethyl}-benzoic acid;
2-methoxy-5-{4-[1-(2-thiophen-2-yl-ethyl)-1H-indol-3-yl]-piperidin-1-ylmethyl}-benzoic acid;
5-{4-[6-fluoro-1-(2-thiophen-2-yl-ethyl)-1H-indol-3-yl]-piperidin-1-ylmethyl}-2-methoxy-benzoic acid;
5-{4-[6-fluoro-1-(2-morpholin-4-yl-ethyl)-1H-indol-3-yl]-piperidin-1-ylmethyl}-2-methoxy-benzoic acid;
5-{4-[1-(2-[1,4]dioxan-2-yl-ethyl)-1H-indol-3-yl]-piperidin-1-ylmethyl}-2-methoxy-benzoic acid;
3-{4-[1-(2-[1,4]dioxan-2-yl-ethyl)-1H-indol-3-yl]-piperidin-1-ylmethyl}-benzoic acid;
2-methoxy-5-[4-(1-thiophen-2-ylmethyl-1H-indol-3-yl)-piperidin-1-ylmethyl]-benzoic acid;
4-bromo-3-[4-(1-pyridin-4-ylmethyl-1H-indol-3-yl)-piperidin-1-ylmethyl]-benzoic acid;
2-methoxy-5-{4-[1-(2-thiophen-3-yl-ethyl)-1H-indol-3-yl]-piperidin-1-ylmethyl}-benzoic acid;
3-{4-[1-(2-morpholin-4-yl-ethyl)-1H-indol-3-yl]-piperidin-1-ylmethyl}-benzoic acid;
2-[2-(4-{1-[2-(benzo[1,3]dioxol-5-yloxy)-ethyl]-1H-indol-3-yl}-piperidin-1-yl)-ethoxy]-benzoic acid;
5-{4-[6-fluoro-1-(2-thiophen-3-yl-ethyl)-1H-indol-3-yl]-piperidin-1-ylmethyl}-2-methoxy-benzoic acid;
5-{4-[1-(5-chloro-thiophen-2-ylmethyl)-6-fluoro-1H-indol-3-yl]-piperidin-1-ylmethyl}-2-methoxy-benzoic acid;
5-[4-(6-fluoro-1-furan-3-ylmethyl-1H-indol-3-yl)-piperidin-1-ylmethyl]-2-methoxy-benzoic acid;
3-{4-[1-(2-pyridin-2-yl-ethyl)-1H-indol-3-yl]-piperidin-1-ylmethyl}-benzoic acid;

5-[4-(6-fluoro-1-thiophen-2-ylmethyl-1H-indol-3-yl)-piperidin-1-ylmethyl]-2-methoxy-benzoic acid;
3-[4-(1-furan-2-ylmethyl-1H-indol-3-yl)-piperidin-1-ylmethyl]-benzoic acid;
2-(2-{4-[1-(2-[1,4]dioxan-2-yl-ethyl)-1H-indol-3-yl]-piperidin-1-yl}-ethoxy)-benzoic acid;
5-[4-(1-furan-2-ylmethyl-1H-indol-3-yl)-piperidin-1-ylmethyl]-2-methoxy-benzoic acid;
5-[4-(1-furan-3-ylmethyl-1H-indol-3-yl)-piperidin-1-ylmethyl]-2-methoxy-benzoic acid;
3-{4-[5-methoxy-1-(2-thiophen-3-yl-ethyl)-1H-indol-3-yl]-piperidin-1-ylmethyl}-benzoic acid;
2-(2-{4-[5-methoxy-1-(2-thiophen-3-yl-ethyl)-1H-indol-3-yl]-piperidin-1-yl}-ethoxy)-benzoic acid;
2-{2-[4-(5-methoxy-1-thiophen-2-ylmethyl-1H-indol-3-yl)-piperidin-1-yl]-ethoxy}-benzoic acid;
3-[4-(5-methoxy-1-thiophen-2-ylmethyl-1H-indol-3-yl)-piperidin-1-ylmethyl]-benzoic acid;
2-methoxy-5-{4-[5-methoxy-1-(2-thiophen-3-yl-ethyl)-1H-indol-3-yl]-piperidin-1-ylmethyl}-benzoic acid;
2-{2-[4-(1-furan-3-ylmethyl-5-methoxy-1H-indol-3-yl)-piperidin-1-yl]-ethoxy}-benzoic acid;
3-[4-(1-furan-3-ylmethyl-5-methoxy-1H-indol-3-yl)-piperidin-1-ylmethyl]-benzoic acid;
2-[4-(1-furan-2-ylmethyl-1H-indol-3-yl)-piperidin-1-ylmethyl]-benzoic acid;
2-[4-(6-fluoro-1-furan-2-ylmethyl-1H-indol-3-yl)-piperidin-1-ylmethyl]-benzoic acid;
3-[4-(6-fluoro-1-furan-2-ylmethyl-1H-indol-3-yl)-piperidin-1-ylmethyl]-benzoic acid;
5-[4-(6-fluoro-1-furan-2-ylmethyl-1H-indol-3-yl)-piperidin-1-ylmethyl]-2-methoxy-benzoic acid;
4-methoxy-2-[4-(5-methoxy-1-thiophen-2-ylmethyl-1H-indol-3-yl)-piperidin-1-ylmethyl]-benzoic acid;
2-[4-(5-methoxy-1-thiophen-2-ylmethyl-1H-indol-3-yl)-piperidin-1-ylmethyl]-benzoic acid;
2-methoxy-5-[4-(5-methoxy-1-thiophen-2-ylmethyl-1H-indol-3-yl)-piperidin-1-ylmethyl]-benzoic acid;
2-[4-(1-furan-2-ylmethyl-5-methoxy-1H-indol-3-yl)-piperidin-1-ylmethyl]-4-methoxy-benzoic acid;
3-[4-(1-furan-2-ylmethyl-5-methoxy-1H-indol-3-yl)-piperidin-1-ylmethyl]-benzoic acid;
2-[4-(1-furan-2-ylmethyl-5-methoxy-1H-indol-3-yl)-piperidin-1-ylmethyl]-benzoic acid;
5-[4-(1-furan-2-ylmethyl-5-methoxy-1H-indol-3-yl)-piperidin-1-ylmethyl]-2-methoxy-benzoic acid;
2-{2-[4-(1-furan-2-ylmethyl-5-methoxy-1H-indol-3-yl)-piperidin-1-yl]-ethoxy}-benzoic acid;
4-methoxy-2-{4-[5-methoxy-1-(2-thiophen-3-yl-ethyl)-1H-indol-3-yl]-piperidin-1-ylmethyl}-benzoic acid;
2-{2-[4-(6-fluoro-1-thiophen-2-ylmethyl-1H-indol-3-yl)-piperidin-1-yl]-ethoxy}-benzoic acid;
5-[4-(6-fluoro-1-thiophen-3-ylmethyl-1H-indol-3-yl)-piperidin-1-ylmethyl]-2-methoxy-benzoic acid;
2-{2-[4-(6-fluoro-1-thiophen-3-ylmethyl-1H-indol-3-yl)-piperidin-1-yl]-ethoxy}-benzoic acid;
2-(2-{4-[6-fluoro-1-(2-thiophen-3-yl-ethyl)-1H-indol-3-yl]-piperidin-1-yl}-ethoxy)-benzoic acid;
2-(2-{4-[1-(5-chloro-thiophen-2-ylmethyl)-6-fluoro-1H-indol-3-yl]-piperidin-1-yl}-ethoxy)-benzoic acid;
2-{2-[4-(6-fluoro-1-furan-3-ylmethyl-1H-indol-3-yl)-piperidin-1-yl]-ethoxy}-benzoic acid;
2-{2-[4-(5-methoxy-1-thiophen-3-ylmethyl-1H-indol-3-yl)-piperidin-1-yl]-ethoxy}-benzoic acid;
3-[4-(5-methoxy-1-thiophen-3-ylmethyl-1H-indol-3-yl)-piperidin-1-ylmethyl]-benzoic acid;
2-(2-{4-[1-(5-chloro-thiophen-2-ylmethyl)-5-methoxy-1H-indol-3-yl]-piperidin-1-yl}-ethoxy)-benzoic acid;
3-{4-[1-(5-chloro-thiophen-2-ylmethyl)-5-methoxy-1H-indol-3-yl]-piperidin-1-ylmethyl}-benzoic acid;
2-methoxy-5-[4-(1-thiophen-3-ylmethyl-1H-indol-3-yl)-piperidin-1-ylmethyl]-benzoic acid;
3-[4-(1-thiophen-3-ylmethyl-1H-indol-3-yl)-piperidin-1-ylmethyl]-benzoic acid;
5-{4-[1-(5-chloro-thiophen-2-ylmethyl)-5-methoxy-1H-indol-3-yl]-piperidin-1-ylmethyl}-2-methoxy-benzoic acid;
3-{4-[5-methoxy-1-(2-thiophen-2-yl-ethyl)-1H-indol-3-yl]-piperidin-1-ylmethyl}-benzoic acid;
2-methoxy-5-{4-[5-methoxy-1-(2-thiophen-2-yl-ethyl)-1H-indol-3-yl]-piperidin-1-ylmethyl}-benzoic acid;
or a pharmaceutically acceptable salt thereof.

10. A process for producing a compound of claim 1, which process comprises for compounds of formula (I) wherein R2 is a carboxyl group, the hydrolysis of a compound of formula (VI)

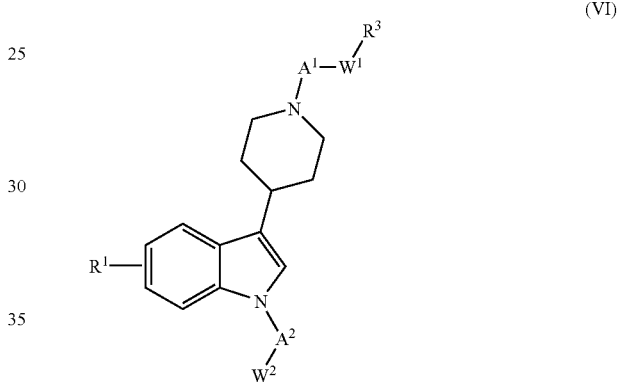

(VI)

wherein in formula (VI) $A^1$, $A^2$, $W^1$, $W^2$ and $R^1$ are as defined in claim 1 and $R^3$ is a —COOR$^4$ group wherein $R^4$ represents a $C_1$–$C_4$ alkyl group.

11. A compound according to claim 1 wherein the alkyl, alkylene, alkyleneoxy, alkylenethio, alkanoylene, hydroxyalkylene and alkoxy groups mentioned in relation to the groups $A^1$, $A^2$, $W^1$, $W^2$, and $R^1$ contain up to seven carbon atoms.

12. A compound according to claim 11, wherein the alkyl, alkylene, alkyleneoxy, alkyenethio, alkanoylene, hydroxyalkylene and alkoxy groups mentioned in relation to the groups $A^1$, $A^2$, $W^1$, $W^2$, and $R^1$ contain up to five carbon atoms.

13. A pharmaceutical composition comprising an antihistaminically effective amount or an antiallergically effective amount of a compound according to claim 1 and a pharmaceutically acceptable diluent or carrier, wherein the allergic disorder or disease is bronchial asthma, rhinitis, conjunctivitis, dermatitis or urticaria.

14. A method for treating an allergic disorder or disease which comprises administering to a human or animal patient in need of such treatment an antihistaminically effective amount or an antiallergically effective amount of a compound according to claim 1 or a composition according to claim 13 wherein the allergic disorder or disease is bronchial asthma, rhinitis, conjunctivitis, dermatitis or urticaria.

* * * * *